US006930193B2

(12) United States Patent
Yaghi et al.

(10) Patent No.: US 6,930,193 B2
(45) Date of Patent: Aug. 16, 2005

(54) ISORETICULAR METAL-ORGANIC FRAMEWORKS, PROCESS FOR FORMING THE SAME, AND SYSTEMATIC DESIGN OF PORE SIZE AND FUNCTIONALITY THEREIN, WITH APPLICATION FOR GAS STORAGE

(75) Inventors: Omar M. Yaghi, Ann Arbor, MI (US); Mohamed Eddaoudi, Ann Arbor, MI (US); Hailian Li, Ann Arbor, MI (US); Jaheon Kim, Ann Arbor, MI (US); Nathaniel Rosi, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 65 days.

(21) Appl. No.: 10/137,043

(22) Filed: Apr. 30, 2002

(65) Prior Publication Data

US 2003/0004364 A1 Jan. 2, 2003

Related U.S. Application Data

(60) Provisional application No. 60/287,489, filed on Apr. 30, 2001, and provisional application No. 60/340,623, filed on Dec. 14, 2001.

(51) Int. Cl.[7] .......................... C07F 13/00; C07F 15/00; C07F 11/00
(52) U.S. Cl. ............................ 556/46; 556/43; 556/51; 556/58; 556/72; 556/89; 556/112; 556/113; 556/136; 556/141; 534/15
(58) Field of Search .............................. 556/43, 46, 51, 556/58, 72, 89, 112, 113, 136, 141; 534/15

(56) References Cited

U.S. PATENT DOCUMENTS 5,648,508 A 7/1997 Yaghi ............................ 556/9

5,862,796 A 1/1999 Seki et al. ............... 123/527

OTHER PUBLICATIONS

Li et al., Nature, vol. 402, pp. 276–279 (1999).*
Bondi, A., *van der Waals Volumes and Radii,* Journal of Phys. Chem., Mar. 16, 1964, vol. 68, No. 3: pp. 441–451.
Bennett, J. M. and J. V. Smith, *Positions of Cations and Molecules in Zeolites with the Faujasite–Type Framework I. Dehydrated Ca–Exchanged Faujasite,* Mat. Res. Bull., 1968, vol. 3, No. 8: pp. 633–642.
Hoskins, B. F. and R. Robson, *Infinite Polymeric Frameworks Consisting of Three Dimensionally Linked Rod–like Segments,* J. Am. Chem. Soc., 1989, vol. 111: pp. 5962–5964.
Fagan, P. J. and M. D. Ward, *Building Molecular Crystals,* Sci. Am., Jul. 1992, pp. 48–54.
Stein, A., S. W. Keller and T. E. Mallouk, *Turning Down the Heat: Design and Mechanism in Solid–State Synthesis,* Science, Mar. 12, 1993, vol. 259: pp. 1558–1564.
Russell, V. A., C. C. Evans, W. Li and M. D. Ward, *Nanoporous Molecular Sandwiches: Pillared Two–Dimensional Hydrogen–Bonded Networks with Adjustable Porosity,* Science, Apr. 25, 1997, vol. 276: pp. 575–579.

(Continued)

*Primary Examiner*—Porfirio Nazario-Gonzalez
(74) *Attorney, Agent, or Firm*—Dierker & Associates, P.C.

(57) ABSTRACT

An isoreticular metal-organic framework (IRMOF) and method for systematically forming the same. The method comprises the steps of dissolving at least one source of metal cations and at least one organic linking compound in a solvent to form a solution; and crystallizing the solution under predetermined conditions to form a predetermined IRMOF. At least one of functionality, dimension, pore size and free volume of the IRMOF is substantially determined by the organic linking compound.

62 Claims, 55 Drawing Sheets

(10 of 55 Drawing Sheet(s) Filed in Color)

OTHER PUBLICATIONS

Hüsing, N. and U. Schubert, *Aerogels–Airy Materials: Chemistry, Structure, and Properties*, Angew. Chem. Int. Ed., 1998, vol. 37: pp. 22–45.

Menon, V. C. and S. Komameni, *Porous Adsorbents for Vehicular Natural Gas Storage: A Review*, J. of Porous Materials, 1998, vol. 5: pp. 43–58.

Jones, C. W., K. Tsuji and M. E. Davis, *Organic–functionalized–molecular sieves as shape–selective catalysts*, Nature, May 7, 1998, vol. 393: pp. 52–54.

Makoto, F., *Self–Assembly of [2]Catenenes Containing Metals in Their Backbones*, Accounts of Chemical Research, 1999, vol. 32, No. 1: pp. 53–61.

Li, H., M. Eddaoudi, M. O'Keeffe and O. M. Yaghi, *Design and synthesis of an exceptionally stable and highly porous metal–organic framework*, Nature, Nov. 18, 1999, vol. 402: pp. 276–279.

Li, H.., C. E. Davis, T. L. Groy, D. G. Kelley and O. M. Yaghi, *Coordinately Unsaturated Metal Centers in the Extended Porous Framework of $Zn_3(BDC)_3 6CH_3OH$ (BDC = 1,4–Benzenedicarboxylate)*, J. Am. Chem. Soc., 1998, vol. 120: pp. 2186–2187.

Klang, Y.-H, G. B. Gardner, S. Lee, Z. Xu and E. B. Lobkovsky, *Variable Pore Size, Variable Chemical Functionality, and an Example of Reactivity within Porous Phenylacetylene Silver Salts*, J. Am. Chem. Soc., 1999, vol. 121: pp. 8204–8215.

Eddaoudi, M., H. Li and O .M. Yaghi, *Highly Porous and Stable Metal—Organic Frameworks: Structure Design and Sorption Properties*, J. Am. Chem. Soc., 2000, vol. 122: pp. 1391–1397.

Noro; S., S. Kitagawa, M. Kondo and K. Seki, *A New, Methane Adsorbant, Porous Coordination Polymer $[(CuSIF_6 (4,4^{3-bipyridine})_2)_n]_1$* Angew. Chem. Int. Ed., 2000, vol., 39, No. 12: pp. 2081–2084.

Yaghi, O.M., M. O'Keeffe and M. Kanatzidis, *Design of Solids from Molecular Building Blocks: Golden Opportunities for Solid State Chemistry*, J. Solid State Chem., 2000, vol. 152: pp. 1–2.

Reineke, T. M., M. Eddaoudi, D. Moler, M. O'Keeffe and O. M. Yaghi, *Large Free Volume in Maximally Interpenetrating Networks: The Role of Secondary Building Units Exemplified by $Tb_2(ADB)_3[CH_3)_2 SO]_4 16[(CH_3)_2 SO]^1$*, J. Am. Chem. Soc., 2000, vol. 122: pp. 4843–4844.

Eddaoudl, M., D. B. Moler, H. Li, B. Chen, T. M. Reineke, M. O'Keeffe and O. M. Yaghi, *Modular Chemistry: Secondary Building Units as a Basis for the Design of Highly Porous and Robust Metal—Organic Carboxylate Frameworks*, Acc. Chem. Res. 2001, vol. 34: pp. 319–330.

Seki, K., *Design of an adsorbent with an ideal pore structure for methane adsorption using metal complexes*, Chem. Commun., 2001, pp. 1496–1497.

Kim, J., B. Chen, T. M. Reineke, H. Li, M. Eddaoudi, D. B. Moler, M. O'Keeffe and O. M. Yaghi, *Assembly of Metal—Organic Frameworks from Large Organic and Inorganic Secondary Building Units: New Examples and Simplifying Principles for Complex Structures*, J. Am. Chem. Soc., 2001, vol. 123: pp. 8239–8247.

Guillou, N., Q. Gao, P. M. Forster, J. Chang, M. Norguès, S. Park, G. Fèrey and A. K. Cheetham, *Nickel(II) Phosphate VSB–5: A Magnetic Nanoporous Hydrogenation Catalyst with 24–Ring Tunnels*, Angew. Chem. Int. Ed, 2001, vol. 40, No. 15: pp. 2831–2834.

Naumov, P., G. Jovanovski, M. Ristova, I. A. Razak, S. Cakir, S. Chantrapromma, H. Fun and S. Weng Ng. *Coordination of Deprotonated Saccharin in Copper(II) Complexes. Structural Role of the Saccharinate Directed by the Ancillary N–heterocyclic Ligands*, Z. Anorg. Alig. Chem., 2002, vol. 628: pp. 2930–2939.

Wallner, H. and K. Gatterer, *Growth of Pure $Ni(OH)_2$ Single Crystals from Solution—Control of the Crystal Size*, Z. Anorg. Allg. Chem., 2002, vol. 628: pp. 2818–2820.

Patoux, S. and C. Masqueller, *Lithium Insertion Into Titanium Phosphates, Silicates and Sulfates*, Chemistry of Materials, 2002, vol. 14, No. 12: pp. 5057–5068.

* cited by examiner

Crystal Structure for IRMOF-3

Crystal data
Cubic, *Fm-3m*
$a = 25.7465(14)$ Å
$V = 17066.9(16)$ Å$^3$
R1 = 0.1201 [I>2σ(I)]
wR2 = 0.3437 (all data)

Crystal Structure for IRMOF-6

SBU of IRMOF-6

Crystal data
Cubic, $Fm\text{-}3m$
$a = 25.8421(15)$ Å
$V = 17257.7(17)$ Å$^3$
$R1 = 0.1366$ [$I > 2\sigma(I)$]
$wR2 = 0.5067$ (all data)

Crystal Structure for IRMOF-9

Crystal data
Orthorhombic, *Pnnm*
$a = 17.128(4)$ Å
$b = 20.001(4)$ Å
$c = 27.305(6)$ Å
$V = 9354(4)$ Å$^3$
R1 = 0.1625 [I > 2σ(I)]
wR2 = 0.4304 (all data)

Crystal Structure for IRMOF-12

Crystal data
Cubic, *Fm3m*
*a* = 34.2807(18) Å
*V* = 40286(4) Å$^3$
R1 = 0.1080 [I > 2σ(I)]
wR2 = 0.3875 (all data)

Crystal Structure for IRMOF-11

Crystal data
Rhombohedral(H), *R3m*
$a = 24.938(2)$ Å
$c = 54.521(6)$ Å
$V = 29365(4)$ Å$^3$
$R1 = 0.1995\ [I > 2\sigma(I)]$
$wR2 = 0.5602$ (all data)

Crystal Structure for IRMOF-14

Crystal data
Cubic, *Fm3m*
*a* = 34.396 Å
*V* = 40693 Å³

Figure 53A  Figure 53B  Figure 53C  Figure 53D
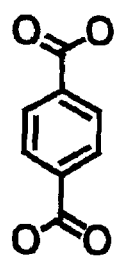 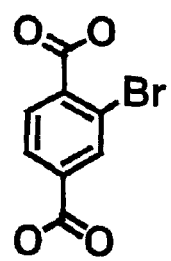 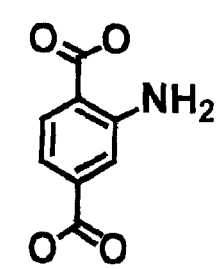 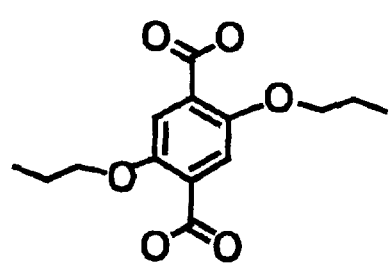
$R_1$-BDC   $R_2$-BDC   $R_3$-BDC   $R_4$-BDC
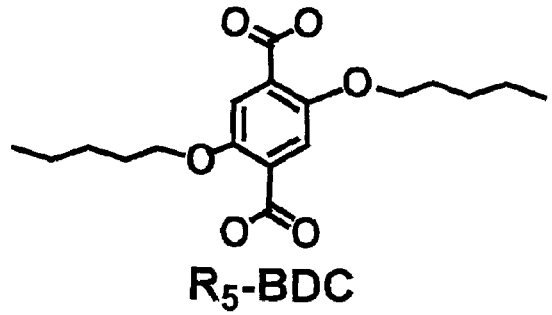 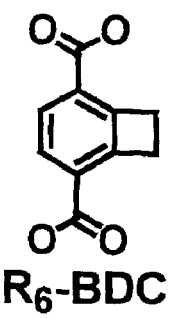 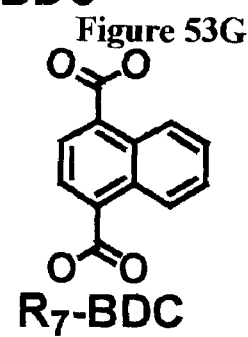
$R_5$-BDC   $R_6$-BDC   $R_7$-BDC
Figure 53E   Figure 53F   Figure 53G
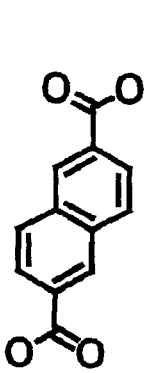 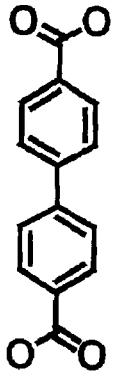 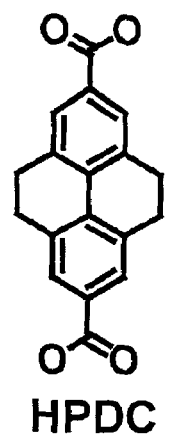 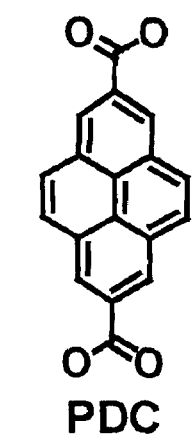 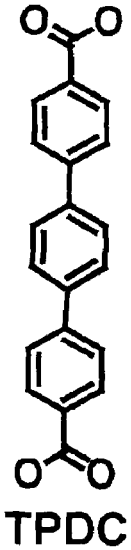
2,6-NDC   BPDC   HPDC   PDC   TPDC
Figure 53H   Figure 53I   Figure 53J   Figure 53K   Figure 53L

ISORETICULAR METAL-ORGANIC FRAMEWORKS, PROCESS FOR FORMING THE SAME, AND SYSTEMATIC DESIGN OF PORE SIZE AND FUNCTIONALITY THEREIN, WITH APPLICATION FOR GAS STORAGE

CROSS-REFERENCE TO RELATED APPLICATIONS

This application claims the benefit of U.S. Provisional Applications Ser. No. 60/287,489, filed Apr. 30, 2001; and Ser. No. 60/340,623, filed Dec. 14, 2001.

STATEMENT REGARDING FEDERALLY SPONSORED RESEARCH OR DEVELOPMENT

This invention was made in the course of research partially supported by a grant from the National Science Foundation (Grant No. DMR-9980469) and a grant from the Department of Energy (Grant No. DE-FG02-99ER15000 and Grant No. DE-FG03-98ER14903). The U.S. government has certain rights in the invention.

BACKGROUND OF THE INVENTION

The present invention relates generally to metal-organic frameworks, and more specifically to such frameworks, which are reticulated into a predetermined porous material with a tailored pore size and/or functionality, and their application as sorbents for storing gases such as methane.

One of the great challenges in porous materials is the design and the achievement of a desired porous material with a tailored pore size and/or functionality. To date, it has not been possible to consistently and efficiently (with a high yield) render porous materials having predetermined characteristics.

A particular goal is to alter chemical composition, functionality, and molecular dimensions without changing the underlying topology. See A. Stein, S. W. Keller and T. E. Mallouk, *Science* 259, 1558 (1993); and P. J. Fagan and M. D. Ward, *Sci. Am.* 267, 48 (1992). Although this has been a dream of scientists and engineers for most of the last century, little progress has been achieved largely due to lack of control over the course of molecular assembly and the inability to predict the orientation of atomic groups in crystals. Unlike the process of building organic molecules, where it is possible to execute the total synthesis of complex ring systems in a step-by-step fashion, the insolubility of extended solids generally necessitates that their assembly be accomplished in a single step. See O. M. Yaghi, M. O'Keeffe, and M. Kanatzidis, *J. Solid State Chem.* 152, 1 (2000).

Porous materials are mainly used for gas/liquid separation, catalysis, luminescence-based sensors, and gas storage. To achieve a specific application, a porous material with a defined pore size and function is needed. To achieve these challenging objectives, many scientists have devoted their knowledge and programs to develop this area.

A stable, porous metal-organic framework was disclosed recently. See Li, Hailian, Mohamed Eddaoudi, M. O'Keeffe and O. M. Yaghi, "Design and synthesis of an exceptionally stable and highly porous metal-organic framework," *Nature*, Vol. 402, pp. 276–279 (18 Nov. 1999). This framework was formed by diffusing triethylamine into a solution of zinc (II) nitrate and $H_2BDC$ (benzenedicarboxylic acid) in N,N'-dimethyl-formamide/chlorobenzene. This resulted in the deprotonation of $H_2BDC$ and its reaction with $Zn^{2+}$ ions. The rendered cubic crystals were designated metal-organic framework (MOF)-5 and were found to comprise an extended, porous network having a three-dimensional intersecting channel system with 12.94 Å spacing between centers of adjacent clusters.

The diffusion of base into the solution is generally accepted in the literature as being an important step in the process of fabricating such MOFs. See, for example, Eddaoudi, Mohamed et al., "Modular Chemistry: Secondary Building Units as a Basis for the Design of Highly Porous and Robust Metal-Organic Carboxylate Frameworks," *Accounts of Chemical Research,* Vol. 34, No. 4, pp. 319–330 (Web publication date 17 Feb. 2001). This article states that a key step to obtaining crystals is to slowly diffuse an organic amine into the reaction mixture.

Although the MOF-5 crystalline structure described in *Nature,* supra, has desirable characteristics, the process for making the structure actually renders a mixture of crystalline structures, the MOF-5 being a relatively low percentage of the mix. Further, the *Nature* MOF-5 structure appears to be limited to a single benzene ring as a linkage between adjacent $Zn_4(O)O_{12}C_6$ clusters.

Others have recently pursued the assembly of extended structures from molecular building blocks. See V. A. Russell, C. C. Evans, W. J. Li and M. D. Ward, *Science* 276, 575 (1997); Y. H. Kiang, G. B. Gardner, S. Lee, Z. T. Xu and E. B. Lobkovsky, *J. Am. Chem. Soc.* 121, 8204 (1999); and B. F. Hoskins and R. Robson, *J. Am. Chem. Soc.* 111, 5962 (1989).

Researchers have attempted to formulate frameworks having longer links between adjacent clusters. Synthesis of open frameworks by assembly of metal ions with di-, tri- and poly-topic N-bound organic linkers such as 4,4'-bipyridine has produced many cationic framework structures. However, attempts to evacuate/exchange guests within the pores usually unfortunately results in the collapse of the host framework.

Further, expanded structures have been formed using long links to increase the spacing between vertices in a net, yielding void space proportional to the length of the linker. However, although such expanded structures provide for large pores (and one would therefore expect a high porosity), in practice they are often found to be highly undesirably interpenetrated and to have low porosity.

Thus, it would be desirable to provide a reproducible metal-organic porous material advantageously having a predetermined pore size and function. It would further be desirable to provide such a porous material which desirably retains its topology even with varied linkage compounds. Yet further, it would be desirable to provide a high yielding method for preparing such porous materials. Still further, it would be desirable to provide such a porous material which may advantageously store gases at desirable pressures such as the predominant natural gas methane.

SUMMARY OF THE INVENTION

The present invention addresses and substantially solves the above-mentioned problems by providing an isoreticular metal-organic framework (IRMOF) and method for systematically forming tbe same. The method comprises the steps of dissolving at least one source of metal cations and at least one organic linking compound in a solvent to form a solution; and crystallizing the solution under predetermined conditions to form a predetermined IRMOF. At least one of functionality, dimension, pore size and free volume of the IRMOF is substantially determined by the organic linking compound.

Further, member(s) of the IRMOFs series have been found to have very high methane storage capacity. Specifically, the inventive IRMOF(s) have been found to have a methane storage capacity of about 155 $cm^3/cm^3$, which is the highest methane storage capacity in any crystalline porous material to date.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Objects, features and advantages of the present invention will become apparent by reference to the following detailed description and drawings, in which:

FIGS. 53A–53L depict various ligands;

SBU: secondary building unit.

IRMOF: Iso-reticular metal-organic framework.

FIG. 55 (A) Thermogravimetrogram for IRMOF-6 including its (B) gas and organic vapor isotherms, and (C) its volulminous uptake of methane gas. The stability of two of themost open IRMOFs (12 and 14) is shown by their (D) X-ray powder diffraction patterns before and after evacuation of guest trapped in the pores.

DETAILED DESCRIPTION OF THE PREFERRED EMBODIMENTS

Figure 1:
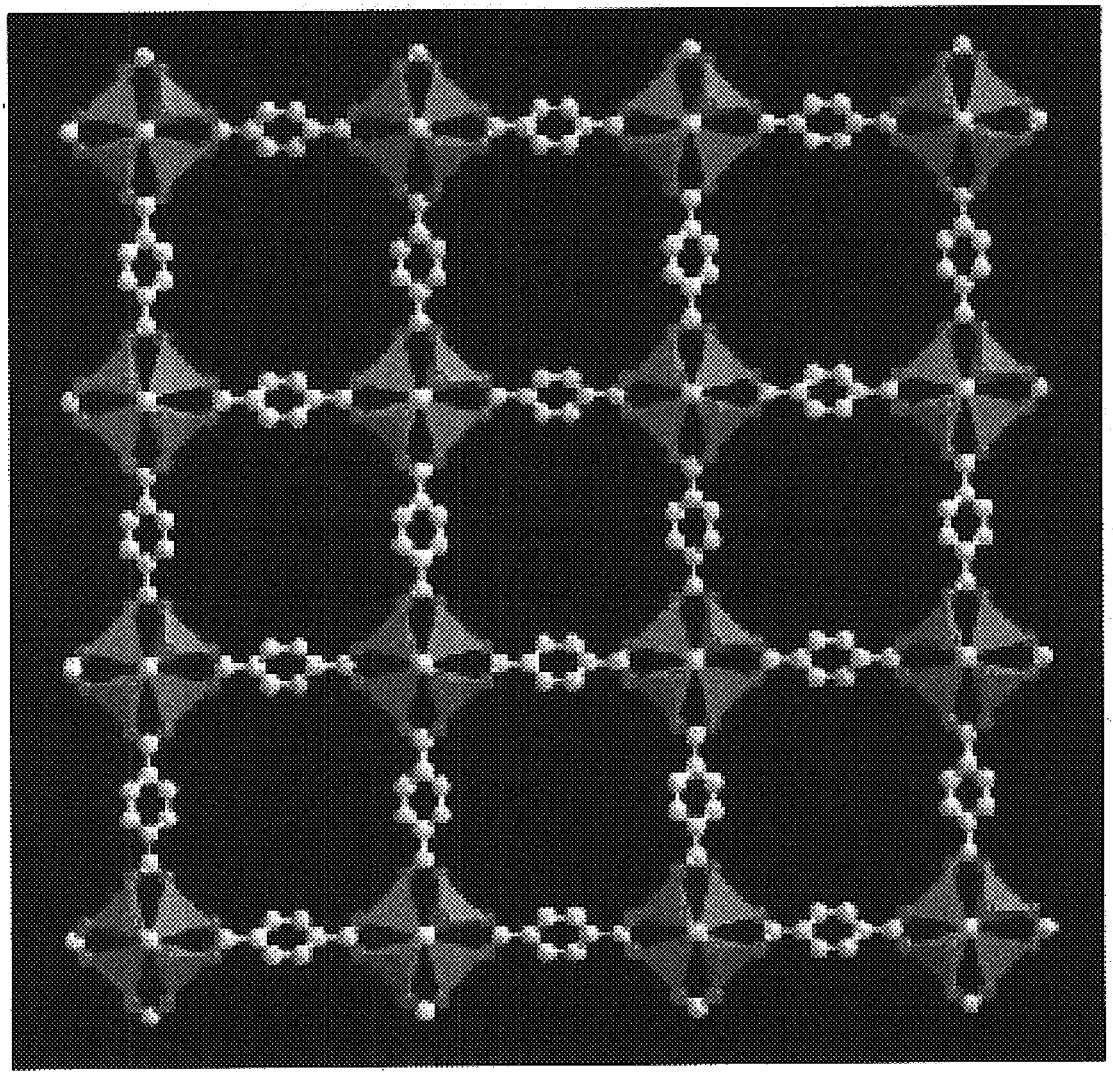
FIG. 1 is a diagrammatic representation of IRMOF 1 of the present invention.

The present invention is predicated upon the unexpected and fortuitous discovery that an extremely stable (with or without the presence of guest molecules within the pores of the framework) and highly (substantially permanently) porous isoreticular metal-organic framework having a topology similar to that shown in FIG. 1 may be formed, even when utilizing linkers other than benzenedicarboxylate. The links in FIG. 1 are single, unsubstituted benzene rings. Contrary to the established literature, it has been fortuitously found that the benzene ring of the dicarboxylate may be substituted with a functional group and/or the link may comprise a plurality of benzene rings (forming a horizontal line, a vertical line, or both, ie. the plurality of rings may be as tall as desired and/or as fat as desired), while retaining a stable network with very high porosity and substantially no undesirable interpenetration.

This fortuitous discovery allows for the fabrication of desired porous materials with predetermined, tailored pore sizes and/or functionalities, depending upon the ligand(s) used.

Some exemplary linking compounds/ligands are depicted immediately below (note that the numbers appearing below the compounds correspond to the number of the IRMOF of which they are part), where X stands for a functional group, such as, for example, hydrogen, amines, halides. X can also be an R group, for example, linear, substituted or cyclo alkanes ($CH_3$—$(CH_2)_n$—$CH_2$—) n=0, 1, 2 . . . , alkenes (double bond), alkynes (triple bond), chains, or ether O—R, where R is the same as mentioned before. More specifically, X may comprise amines (primary, secondary, tertiary); aromatic amines, pyridine, and pyrimidine-like 5 or 6 membered rings; halides including substituted —RX; alcohols: ROH; thiols: RSH; sulfonates —R—$SO_3$; nitro groups —R($NO_2^-$); phosphates —R—$PO_2^-$; epoxides; alkanes $CH_2$($CH_3$)$_n$$CH_2$ n=0, 1 . . . ; alkenes; alkynes; aldehydes (RCOH); ketones (—RCOR); esters $RCO_2R$; carboxylic acids; cycloalkanes; cycloalkenes; cycloalkynes; silyls derivatives; boranes derivatives; and ferrocenes and other metallocenes.

1

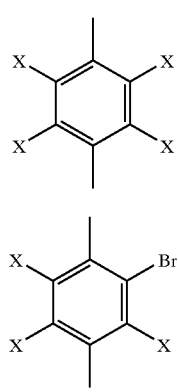

2

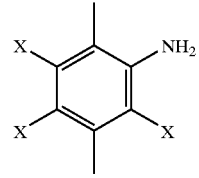

3

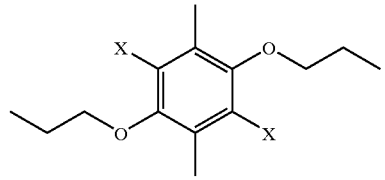

4

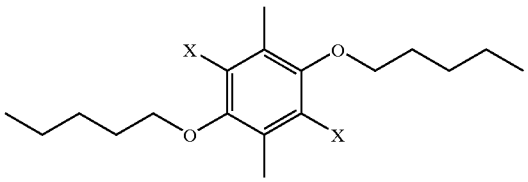

5

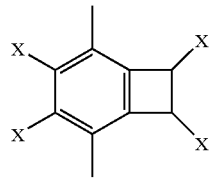

6

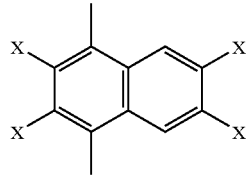

7

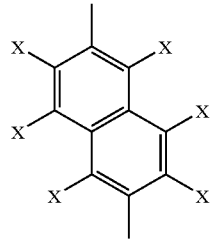

8

9, 10

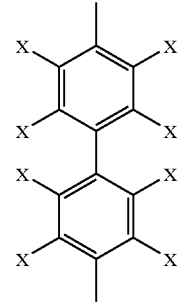

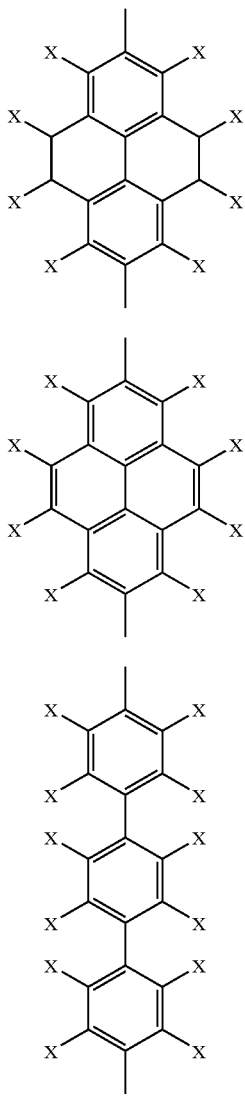

The present invention discloses the first series of tailored porous materials. Iso-reticular Metal-Organic Frameworks (IRMOFs) are important avenues toward consistently and efficiently (with a high yield) rendering stable, substantially permanently porous materials having a predetermined characterization. "Reticular" is an adjective defined in Random House Webster Unabridged Dictionary as "having the form of a net; netlike." Isoreticular can thus be defined as: having the same network topology.

In general, MOFs are formed by a combination of metal cations and polydentate organic linkers. The incorporation of organic linkers as an integral part into the framework is of great advantage due to the ability to apply all the well-established organic chemistry knowledge to functionalize the linker. The present invention shows that it is possible to design porous materials, "IRMOFs," with tailored pores sizes and functionality/ies, an unprecedented achievement to date.

In order to design a target extended structure with the same precision practiced in organic synthesis, it is desirable that (a) the starting building blocks have the relevant attributes necessary to assemble into the skeleton of the desired structure, (b) the synthesis be adaptable to using derivatives of those building blocks to produce structures with the same skeleton but different functionalities and dimensions, and importantly, (c) the products should be highly crystalline to allow the full characterization of their atomic connectivity by X-ray diffraction techniques.

The most notable example of a truly porous metal-organic frameworks (MOF) is MOF-5 in which octahedral Zn—O—C clusters are linked by benzene struts to reticulate into a primitive cubic structure (FIG. 1). The exceptional rigidity and high porosity of MOF-5 led to its use as a target in studies aimed at overcoming the three challenges outlined immediately hereinabove and also to developing the next phase of this chemistry, namely, functionalization of the pores and systematic variation of their size—aspects that are highly sought after in solid-state chemistry and only recently pursued in crystalline zeolite research. See C. W. Jones, K. Tsuji and M. E. Davis, Nature 393, 52 (1998).

In the present invention, we disclose the successful, systematic design and construction of a series of frameworks having structures based on the skeleton of MOF-5, wherein the pore functionality and size have been varied without changing the original cubic topology. Furthermore, the implications and scope of such controlled design are revealed by the properties of several members of this series, where pore sizes in the mesoporous range (>20 Å) have been achieved, the highest methane storage capacity measured, and the lowest crystal density of any material has been attained.

In general, a specific metal salt and a linear ditopic carboxylate were dissolved in a predefined solvent. Depending on the solubility and the acidity of the ligand, the mixture can either be left at room temperature to crystallize, and/or if necessary or desired, a diluted base is added or allowed to diffuse into the mixture to initiate the reaction, and/or transferred to a closed vessel and heated to a predetermined, precise temperature.

The selected conditions are ideal to form the cluster $M_4O(CO_2)_6$ (also called a secondary building unit (SBU)). The SBU in the case of IRMOFs occupy the corners of the cube, and ditopic linkers link them. The resultant dimension, pore size and free volume are related to linkers: Expanded structure results from expanding the linker to a series of linear benzene rings, and reducing the pore volume is generated by introducing functional groups on the benzene rings (those pointing toward the inner cavities).

Some crystalline metal-organic microporous materials are broadly disclosed in U.S. Pat. No. 5,648,508, which is incorporated herein by reference in its entirety.

An isoreticular metal-organic framework (IRMOF) according to a non-limitative embodiment of the present invention consists essentially of a plurality of secondary building units (SBUs), each of the plurality of SBUs comprising an $M_4O(CO_2)_6$ cluster. A compound links adjacent SBUs, the linking compound may comprise a linear ditopic carboxylate having at least one phenyl group and at least one functional group X attached to at least one phenyl group. The IRMOF formed has a substantially permanent porosity and is very stable, with or without the presence of guest molecules.

M in the SBU is a metal cation of a metal selected from the group consisting of beryllium, zinc, cadmium, mercury, and any of the transition metals (in the periodic table, scandium through copper, yttrium through silver, lanthanum through gold, and all known elements from actinium on). X may be any suitable functional group as necessary and/or desired. In the preferred embodiment, X is selected from the group enumerated hereinabove.

A method of forming an isoreticular metal-organic framework (IRMOF) comprises the step of dissolving at least one metal salt and at least one linear ditopic carboxylate in a solvent to form a solution. The solvent may be any suitable solvent, however, in the preferred embodiment, the solvent is any nitrogen containing solvent having a boiling point of less than about 250° C. The solution is then crystallized to form the targeted IRMOF.

The metal salt is formed from a metal cation and an anion, the metal cation being a cation of a metal selected from the group consisting of beryllium, zinc, cadmium, mercury, and any of the transition metals. The anion is selected from the group consisting of $F^-$, $Cl^-$, $Br^-$, $I^-$, $ClO^-$, $ClO_2^-$, $ClO_3^-$, $ClO_4^-$, $OH^-$, $NO_3^-$, $NO_2^-$, $SO_4^{2-}$, $SO_3^{2-}$, $PO_4^{3-}$, $CO_3^{2-}$, and $PF_6^-$ and organic counter ions such as acetate $CH_3CO_2^{2-}$, triphlates $CF_3 SO_3^-$.

In the preferred embodiment, the linear ditopic carboxylate/carboxylic acid has at least one phenyl group. In a further preferred embodiment, at least one functional group X is attached to the at least one phenyl group. X is as defined hereinabove.

The crystallizing step is carried out by: leaving the solution at room temperature; adding a diluted base to the solution to initiate the crystallization; diffusing a diluted base into the solution to initiate the crystallization; and/or transferring the solution to a closed vessel and heating to a predetermined temperature.

It has been unexpectedly and fortuitously discovered in the present invention that, whereas diffusion of base into the solution has been recognized as a key step in the formation of MOFs, the method of the present invention has advantageously formed very high yields (about 93%) of pure IRMOF either without any base at all, or by addition (not diffusion) of base into the solution.

It is to be understood that the linking compounds/ligands possessing multi- and/or poly-dentate functional groups may or may not bring with them one or more corresponding counter cations, such as, for example, $H^+$, $Li^+$, $Na^+$, $K^+$, $Mg^{2+}$, $Ca^{2+}$, $Sr^{2+}$, ammonium ion, alkylsubstituted ammonium ions, and arylsubstituted ammonium ions, or one or more counter anions, such as, for example, $F^-$, $Cl^-$, $Br^-$, $I^-$, $ClO^-$, $ClO_2^-$, $ClO_3^-$, $ClO_4^-$, $OH^-$, $NO_3^-$, $NO_2^-$, $SO_4^{2-}$, $SO_3^{2-}$, $PO_4^{3-}$, $CO_3^{2-}$, and $PF_6^-$ and organic counter ions such as acetate $CH_3CO_2^{2-}$, triphlates $CF_3SO_3^-$.

The crystalline microporous materials of the present invention may be synthesized using metal ions having distinctly different coordination geometries, in combination with a ligand possessing multi- and/or poly-dentate functional groups.

It is to be understood that the metal ions may be in the form of a metal salt formed from the metal ions with anions, such as, for example, $F^-$, $Cl^-$, $Br^-$, $I^-$, $ClO^-$, $ClO_2^-$, $ClO_3^-$, $ClO_4^-$, $OH^-$, $HCO_2^-$, $NO_3^-$, $NO_2^-$, $SO_4^{2-}$, $SO_3^{2-}$, $PO_4^{3-}$, $CO_3^{2-}$, $B_4O_7^{2-}$ and $PF_6^-$ and organic counter ions such as acetate $CH_3CO_2^{2-}$, triphlates $CF_3 SO_3^-$.

Note that in various crystal structure figures, the yellow spheres represent the largest van der Waals spheres that would fit in the cavities without touching the frameworks.

The design of an isoreticular metal-organic framework (IRMOF) series based on MOF-5 was initiated by determining the reaction conditions necessary to produce, in situ, the octahedral cluster with a ditopic linear carboxylate link. In this context, the original low yielding synthesis of MOF-5 (described in Nature 402, supra) was re-examined and developed into a high yielding preparation: an N,N'-diethylformamide (DEF) solution mixture of $Zn(NO_3)_2$.$4H_2O$ and the acid form of 1,4-benzenedicarboxylate (BDC) are heated (85–105° C.) in a closed vessel to give crystalline MOF-5, $Zn_4O(R_1—BDC)_3$ ($R_1$=H), hereafter termed IRMOF-1, in 90% yield. The simplicity of the method and the facility with which IRMOF-1 can be obtained were some of the indications that the use of other ditopic carboxylate links under closely related, if not identical, conditions would yield the same type of frameworks having diverse pore sizes and functionalities.

Indeed, employing each of the links $R_2$—BDC, $R_3$—BDC, $R_4$—BDC, $R_5$—BDC, $R_6$—BDC, $R_7$—BDC, 2,6-NDC, BPDC, HPDC, PDC, and TPDC instead of BDC yielded IRMOF-2–16, including the non-interpenetrating structures of BPDC, HPDC, PDC, and TPDC. See FIGS. 53A–53L. It is preferred that the solvent used to synthesize the IRMOFs be N,N'-diethylformamide (DEF) or combined with other solvents such as alcohols and the like. IRMOFs may also be made using any formamide derivatives, eg. N, N'—$R_2$formamide (R may be an alkane, alkene, and the like) as a predominant solvent or mixed.

Each member of the IRMOF series has been isolated and subsequently formulated by chemical microanalysis and single crystal X-ray diffraction studies. All IRMOFs were formulated as $Zn_4O(Link)_3.(DEF)_x$. All the intensity data were collected on Bruker SMART CCD diffractometer with a graphite monochromated MoK$\alpha$($\lambda$=0.71073 Å) radiation. Structures were solved by direct methods and successive difference Fourier syntheses with SHELXTL software package. Final R1 values were calculated with I>2$\sigma$(I).

Crystal data for:

IRMOF-2: cubic, space group Fm-3m, a=25.772(1) Å, V=17117(1) Å$^3$, Z=8, R1=0.0976.

IRMOF-3: cubic, Fm-3m, a=25.747(1) Å, V=17067(2) Å$^3$, Z=8, R1=0.1160.

IRMOF-4: cubic, Fm-3m, a=25.849(1) Å, V=17272(2) Å$^3$, Z=8, R1=0.0706.

IRMOF-5: cubic, Pm-3m, a=12.882(1) Å, V=2137.6(3) Å$^3$, Z=1, R1=0.1181.

IRMOF-6: cubic, Fm-3m, a=25.842(2) Å, V=17258(2) Å$^3$, Z=8, R1=0.1325.

IRMOF-7: cubic, Pm-3m, a=12.914(3) Å, V=2153.9(7) Å$^3$, Z=1, R1=0.1957.

IRMOF-8: cubic, Fm-3m, a=30.092(2) Å, V=27248(3) Å$^3$, Z=8, R1=0.1691.

IRMOF-9: orthorhombic, a=17.147(1) Å, b=23.322(1) Å, c=25.255(1) Å, V=10099.6(8) Å$^3$, Z=4, R1=0.0802.

IRMOF-10: It was not possible to obtain single crystals of sufficient quality to perform an X-ray single crystal analysis study. However, its observed X-ray powder diffraction pattern was the same as that observed for IRMOF-12 (below), and it was confirmed by a simulated pattern for IRMOF-10 based on IRMOF-12 coordinates: cubic, Fm-3m, a=34.281(2) Å, V=40286(4) Å$^3$, Z=8.

IRMOF-11: trigonal, R-3m, a=24.822(1) Å, c=56.734(3) Å, V=30272(3) Å$^3$, Z=12, R1=0.0963.

IRMOF-12: cubic, Fm-3m, a=34.281(2) Å, V=40286(4) Å$^3$, Z=8, R1=0.1080.

IRMOF-13: Same as treatment for IRMOF-10 but using IRMOF-11: Trigonal, R-3m, a=24.822(1) Å, c=56.734(3) Å, V=30272(3) Å$^3$, Z=12.

IRMOF-14: cubic, Fm-3m, a=34.381(13) Å, V=40642(26) Å$^3$, Z=8, R1=0.1914.

IRMOF-15: cubic, Im-3m, a=21.459(1) Å, V=9882(1) Å$^3$, Z=1, R1=0.1164.

IRMOF-16: cubic, Pm-3m, a=21.490(1) Å, V=9925(1) Å$^3$, Z=1, R1=0.1845.

Figure 37:
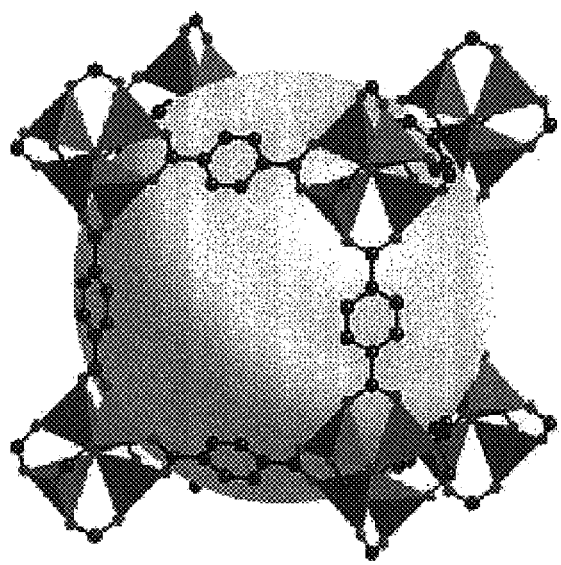
FIGS. 37–52 are single crystal X-ray structures of IRMOF-1 to -16, respectively. Color scheme and drawings conditions: Zn (blue polyhedra), O (red spheres), C (black and gray spheres), Br (green spheres), amino-groups in FIG. 3 (blue spheres). All hydrogen atoms and guests are omitted, and only one orientation of disordered atoms, common to most of the links and in some Zn—O—C units, is shown for clarity.
Figure 38:
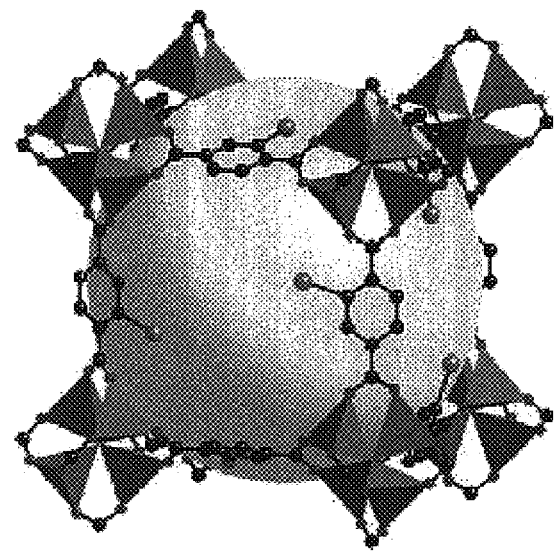
Figure 39:
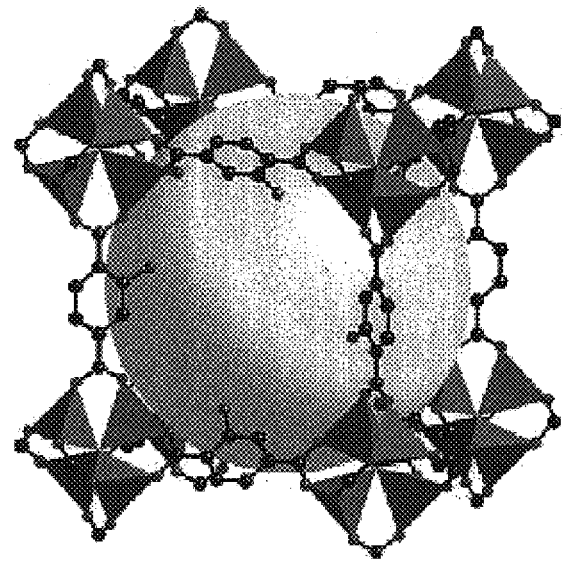
Figure 40:
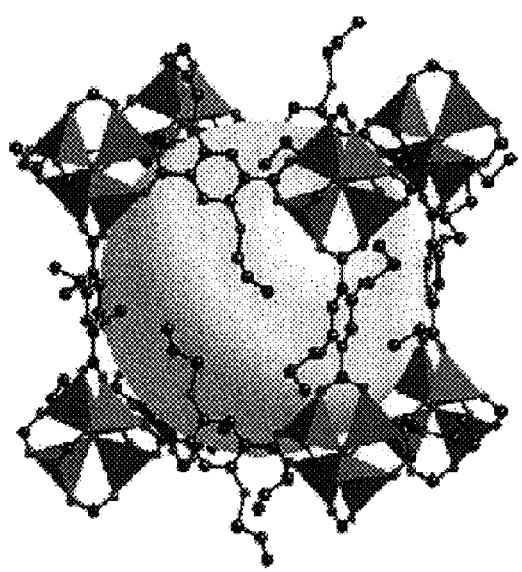
Figure 41:
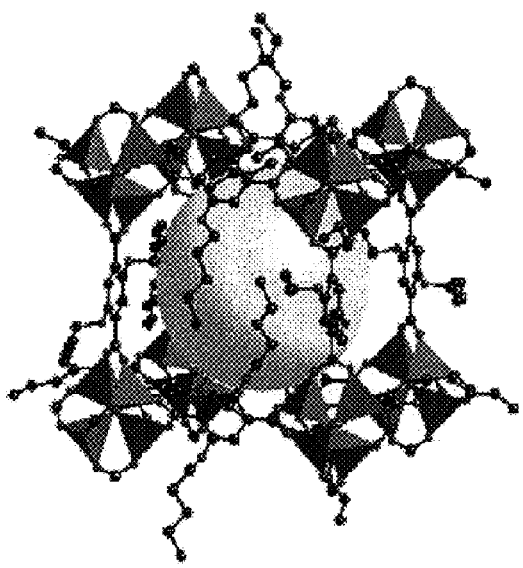
Figure 42:
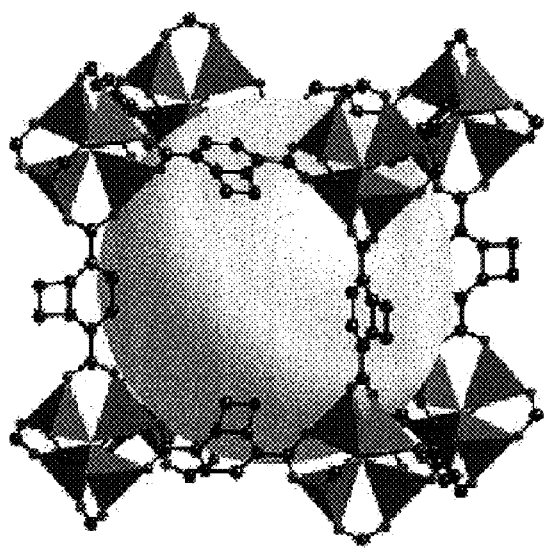
Figure 43:
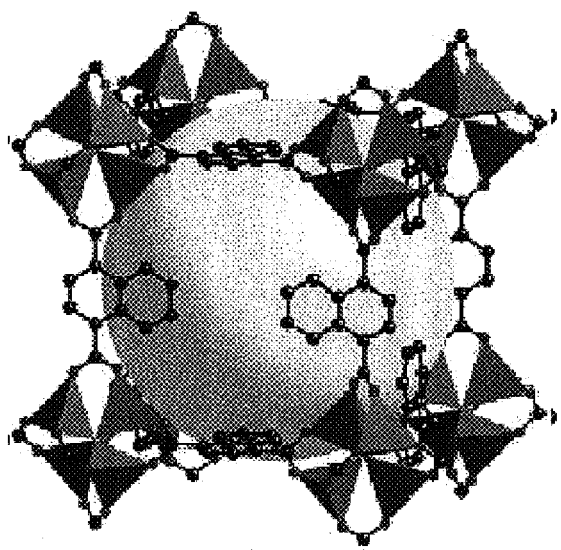

All IRMOFs have the expected topology of $CaB_6$ (see M. O'Keeffe and B. G. Hyde, *Crystal Structures I: Patterns and Symmetry* (Mineralogy Society of America, Washington, D.C., 1996)) adapted by the prototype IRMOF-1 (FIG. 37), in which an oxide-centered $Zn_4O$ tetrahedron is edge-bridged by six carboxylates to give the octahedron-shaped SBU that reticulates into a 3-D cubic porous network. However, the IRMOFs differ in the nature of functional groups decorating the pores and in the metrics of their pore structure.

In IRMOF-2 to 7, BDC links with bromide, amine, n-propoxy, n-pentoxy, cyclobutyl, and fused benzene functional groups reticulate into the desired structure wherein these groups are now pointing into the voids (FIGS. 2 to 7). These results indicate the general nature of the synthetic method and illustrate its amenability to employing a wide variety of carboxylate links having a diversity of functional groups—rare aspects that heretofore remain largely absent in crystalline solid-state and porous materials research. See C. W. Jones, K. Tsuji and M. E. Davis, *Nature* 393, 52 (1998).

Further, the present invention shows that expansion of the pores is also contemplated as being within the purview of the present invention. This is illustrated by the structures of IRMOF-8 to 16 (FIGS. 8 to 16), in which progressively longer links have been successfully employed.

Figure 44:
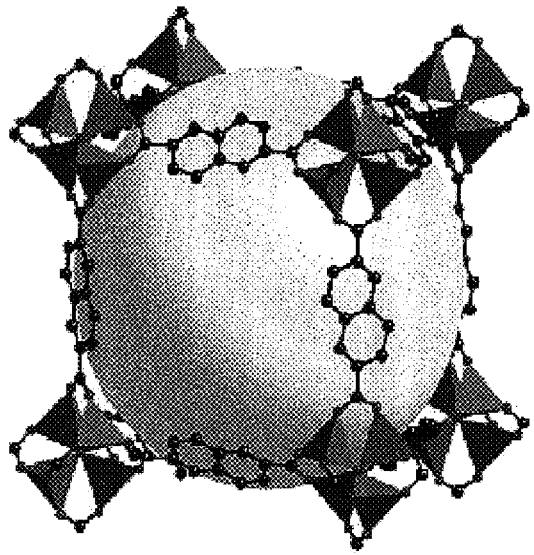
Figure 45:
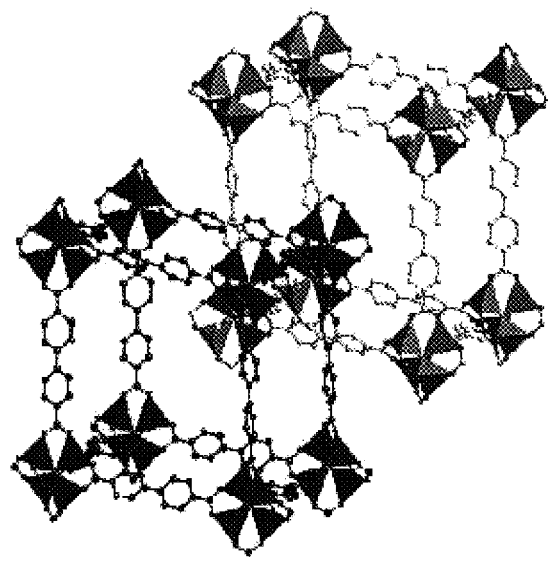
Figure 46:
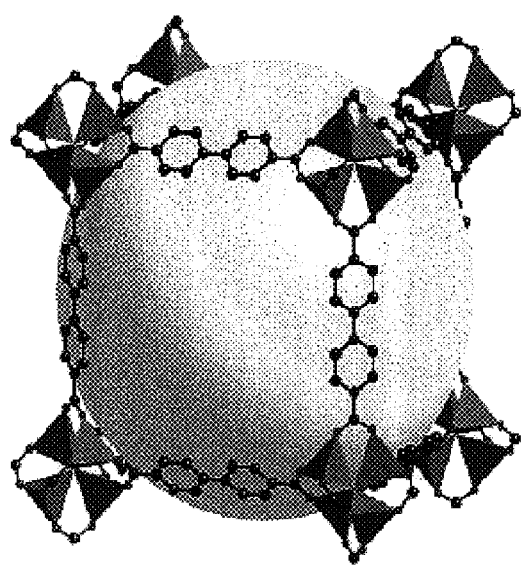
Figure 47:
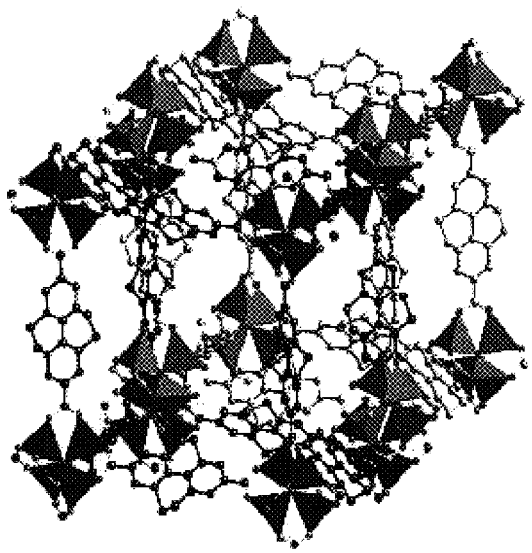
Figure 48:
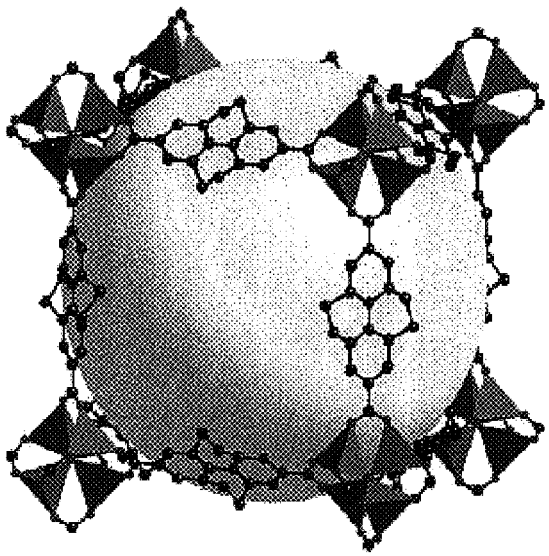
Figure 49:
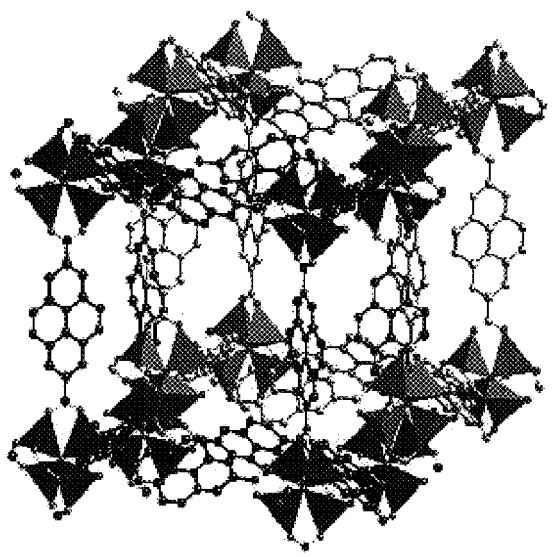
Figure 50:
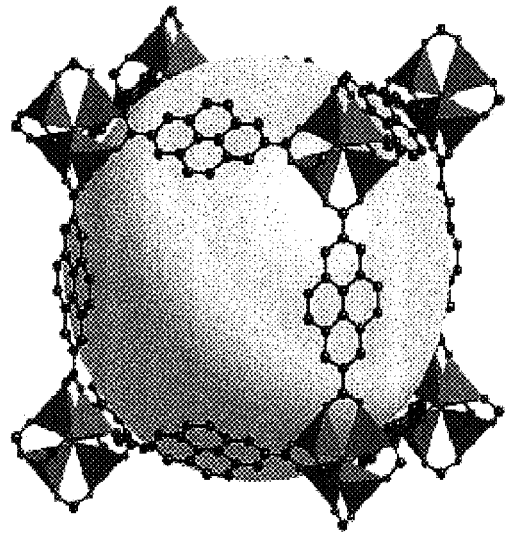
Figure 51:
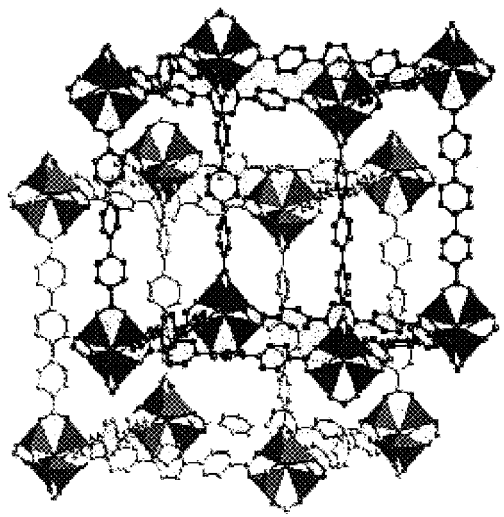
Figure 52:
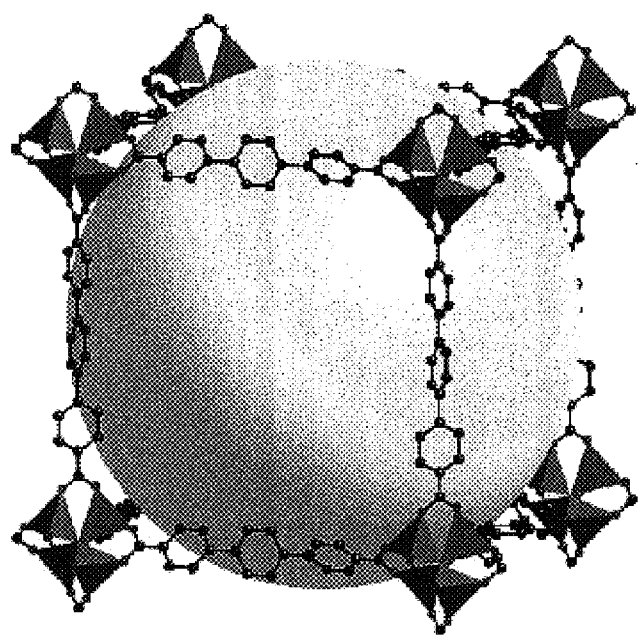

Previous geometric analysis of the primitive cubic system showed that expansion of links results in interpenetrating frameworks, sometimes with optimal porosity. See T. M. Reineke, M. Eddaoudi, D. Moler, M. O'Keeffe and O. M. Yaghi, *J. Am. Chem. Soc.* 122, 4843 (2000). In fact, with the exception of the non-interpenetrating structure involving 2,6-NDC (IRMOF-8) (FIG. 44), each of BPDC, HPDC, PDC and TPDC (respectively, IRMOF-9, 11, 13, and 15; FIGS. 9, 11, 13, and 15) are reticulated as doubly interpenetrating structures. However, by carrying out the original reactions under more dilute conditions, non-interpenetrating counterparts have been successfully achieved for all links including TPDC (IRMOF-10, 12, 14, and 16; FIGS. 10, 12, 14, and 16); a rare achievement in view of the fact that no strategies have thus far been described for the synthesis of both interpenetrating and non-interpenetrating forms of the same extended structure (Similar behavior has been described for catenated discrete molecules: M. Fujita, *Acc. Chem. Res.* 32, 53 (1999)).

Figure 54C:
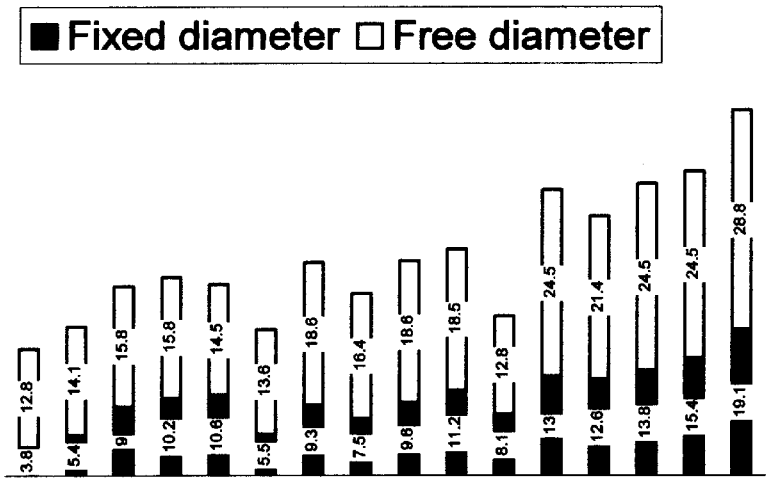
FIG. 54 (Bottom to top): For IRMOF-1-16, A) the calculated (using cerius$^2$ version 4.2) percent free volume (yellow), B) crystal densities (light brown), and C) free diameter (green) and fixed diameter (blue), respectively obtained by measuring the diameter of a sphere that would pass through the aperture and another that would fit inside the pores without overlapping with framework atoms; and Definitions Isoreticular: having the same network topology.

Comparison of the percent free volume in crystals of IRMOF-1–16 (FIG. 54A) shows that it varies in small increments (1 to 5%) from 55.8% in IRMOF-5 to 91.1% in IRMOF-16. Remarkably, the lowest percent free volume obtained in this series exceeds that found in some of the most open zeolites such as faujasite (see M. J. Bennett, J. V. Smith, *Mater. Res. Bull.* 3, 633 (1968)) in which the free space is 45–50% of the crystal volume. In fact, the fraction of free space in crystals of the expanded IRMOF series, especially those of IRMOF-8, 10, 12, 14 and 16 has generally only been achievable in non-crystalline porous systems such as $SiO_2$ xerogels and aerogels. See N. Hüsing, U. Schubert, *Angew. Chem. Int. Ed.* 37, 22 (1998).

Figure 54B:
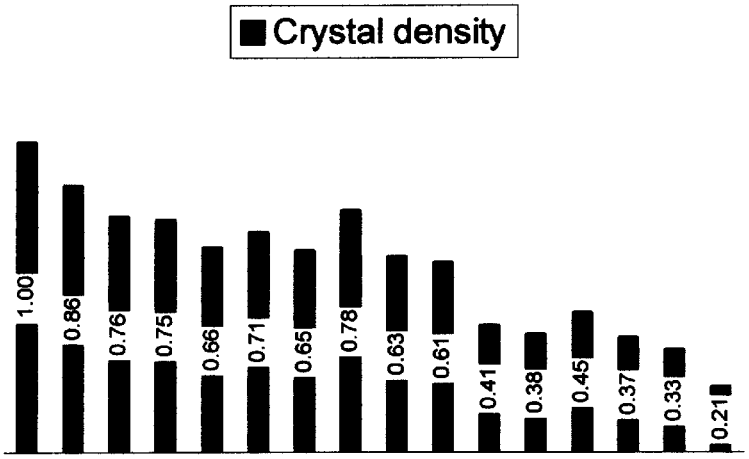
Figure 54A:
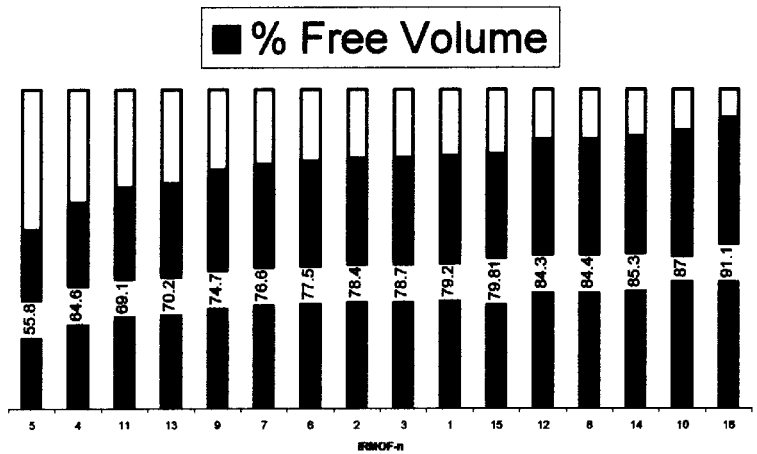

It is worth noting that the calculated crystal densities (in the absence of guests) of these materials also vary in small increments (ca. 0.1) in the range 1.00 g/cm$^3$ for IRMOF-5 to 0.21 g/cm$^3$ for IRMOF-16 (FIG. 54B). Moreover, it is remarkable that the densities of IRMOF-8, 10, 12, 14, 15 and 16 are the lowest recorded for any crystalline material known to date. As far as is known, the next lowest density is that of Li metal (0.56 g/cm$^3$). The ability to design IRMOFs with low densities below 1 ml/g and specifically lower than 0.6 ml/g is a clear consequence of the power of isoreticular chemistry.

Figure 18:
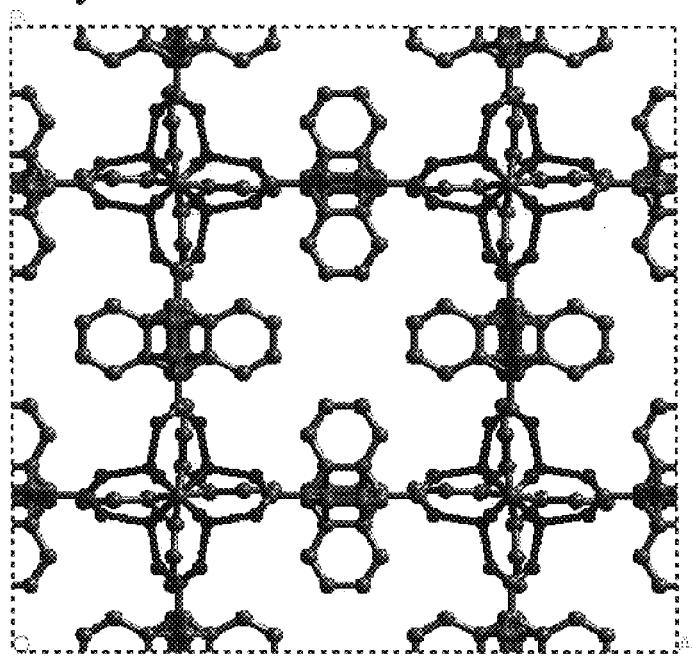
FIG. 18 is a diagrammatic representation of a crystal structure for IRMOF-7.

As expected, the impact of functionalization on pore dimensions is pronounced: relative to IRMOF-1, both the free and fixed diameters of the pores in IRMOF-2 to 7 are modulated downward at approximately 2 Å intervals in the respective ranges, 11.2 to 3.8 Å and 18.6 to 12.8 Å (FIG. 54C). Also, a similar trend is observed for the interpenetrating structures, where pore sizes that fall below those of the IRMOF-1 are obtained. However, all the expanded non-interpenetrating structures have free and fixed diameter values that are much higher, falling within the respective ranges 12.6 to 19.1 Å and 21.4 to 28.8 Å (FIG. 18)—the latter upper limit being in the mesoporous range, indicating the likelihood that such reticular chemistry may be employed more routinely towards the design and synthesis of crystalline and fully-ordered mesoporous crystals.

Given the exceptional attributes of such materials, including their thermal stability, periodicity, the ability to append functional groups in the pores, and the demonstrated systematic variation in pore size and porosity, it is expected that each member of this series would exhibit an unusually rich inclusion chemistry. Results hereinbelow in at least one direction, that of methane storage, provide a glimpse into the vast potential of IRMOFs.

Although methane constitutes one of the most abundant sources of energy on earth, it is the least utilized source of fuel due to the long-standing challenge in its transport and storage at practical temperatures and pressures; conditions believed to be attainable by sorption of methane into porous materials. See V. C. Menon, S. Komaeneni, *J. Porous Mater.* 5, 43 (1998). Given that IRMOF-6 has an aperture (van der Waals dimension of 5.9 Å) (Van der Waals radius of C (1.70 Å) was employed in determination of distance parameters; Bondi, A. *J. Phys. Chem.* 68, 441 (1964)) considered to be suitable for methane uptake, the present inventors sought to examine its viability in methane storage.

Figure 55A:
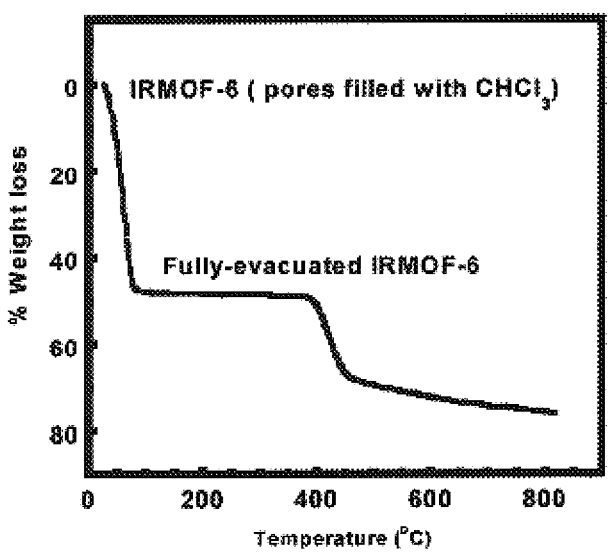

It was necessary first to study IRMOF-6 using thermal gravimetric and gas sorption techniques to show that its framework has the high porosity and rigidity needed to allow maximum uptake of methane. Thus the chloroform exchanged IRMOF-6, $Zn_4O(R_6—BDC)_3(CHCl_3)_7$, was heated gradually to 800° C. under inert atmosphere. A large and sharp weight loss of 50% of the original sample was observed below 100° C., which was attributed to liberation of all chloroform guests from the pores (Calcd: 49%) (FIG. 55A). The evacuated framework has a stability range of 100 to 400° C. as evidenced by the fact that no additional weight loss was observed at those temperatures, after which the framework eventually decomposes.

The gas sorption isotherm was measured for IRMOF-6 to show that it has a rigid framework, and that it can maintain its porosity in the absence of guests. An exact amount of the chloroform-exchanged IRMOF-6 was introduced into a microbalance apparatus, and evacuated at room temperature and 10-5 torr according to already published protocol. See M. Eddaoudi, H. Li and O. M. Yaghi, *J. Am. Chem. Soc.* 122, 1391 (2000). All the chloroform guest molecules were removed from the pores, as confirmed by the fact that no additional weight change was observed upon evacuating the sample overnight and heating it to 150° C.

Figure 55B:
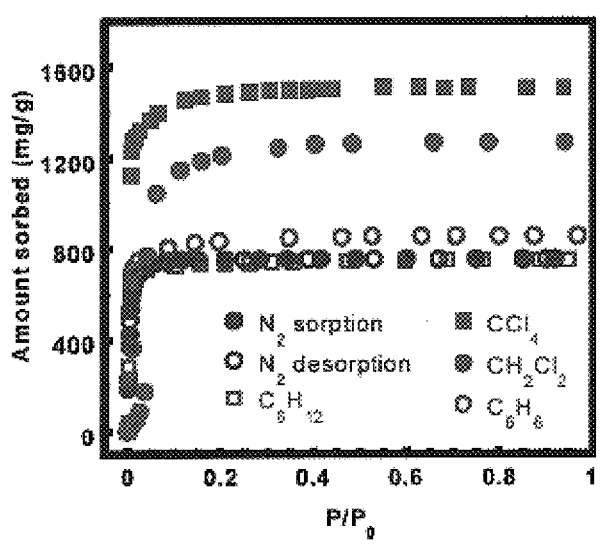
Figure 55C:
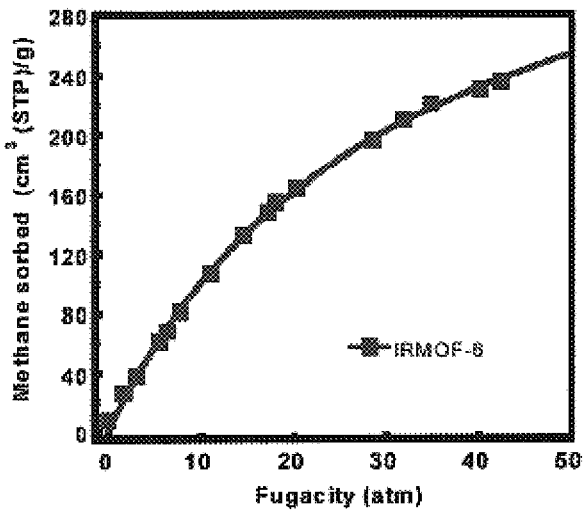

At this point, the X-ray powder diffraction of the evacuated form of IRMOF-6 was found to be identical to that of the as-synthesized form, indicating the architectural stability of the evacuated framework. Thus, increments of nitrogen gas were introduced into the chamber containing the evacuated framework, at 78 K, and the resulting weight changes after each addition were recorded and plotted (FIG. 55B). This revealed a reversible type I isotherm behavior characteristic of a microporous material. The plateau was reached at relatively low pressure with no additional uptake at relatively medium pressures (near condensation pressure $P/P_0 \sim 0.5$), confirming the homogeneity of the pores.

By applying the Langmuir and DR equations, the Langmuir surface area and pore volume, respectively, were estimated to be $S_{langmuir}$=2,630 m$^2$/g and $V_p$=0.60 cm$^3$/cm$^3$. Furthermore, the evacuated sample was also exposed to different organic vapors (CH$_2$Cl$_2$, C$_6$H$_6$, CCl$_4$ and C$_6$H$_{12}$) to also give type I reversible isotherms (FIG. 55B), and pore volumes that converged to the same values (0.57 to 0.60 cm$^3$/cm$^3$) for all sorbents, further confirmation of the homogeneity of the pores. See S. J. Gregg and K. S. W., *Adsorption Surface Area and Porosity*, Academic Press, London, UK, 2nd Ed (1982).

The exceptionally high surface area and pore volumes observed for IRMOF-6 coupled with its appropriately designed aperture made it an ideal candidate for methane storage. Indeed, the methane sorption isotherm was measured in the pressure range 0 to 45 atm and room temperature, and found to have an uptake of 240 cm$^3$/g (155 cm$^3$/cm$^3$) at 36 atm (FIG. 55C), which is the highest methane capacity recorded for any crystalline material including zeolite 5A (87 cm$^3$/cm$^3$) and other coordination frameworks up to (213 cm$^3$/g). See V. C. Menon, S. Komaeneni, *J. Porous Mater.* 5, 43 (1998); K. Seki, *Chem. Commun.* 16, 1496 (2001); and S. Noro, S. Kitagawa, M. Kondo and K. Seki, *Angew. Chem.*, Int. Ed., 39, 2081 (2000).

Based on v/v, the amount of methane sorbed by IRMOF-6 at 36 atm (generally regarded as a substantially safe and cost effective pressure limit), represents 70% of the amount generally stored in laboratory compressed methane cylinders in which significantly higher, less cost effective, and (in certain circumstances) potentially less safe pressure (205 atm) is employed. It is believed that the present invention is an advance which will impact the impending use of these materials in automobile fueling. See U.S. Pat. No. 5,862,796, issued to K. Seki et al. on Jan. 26, 1999.

Methane uptake was also evaluated by testing IRMOF-1 and IRMOF-2 under the same conditions where their uptake was found to be lower (135 and 120 cm$^3$/cm$^3$) than that of IRMOF-6—a significant difference that may be attributable to the hydrophobic nature of H$_4$C$_2$ units in IRMOF-6. Thus, functionalizing the pores with larger hydrocarbons as illustrated in IRMOF-4, 5, and 7, may indeed result in even higher capacities.

Figure 55D:
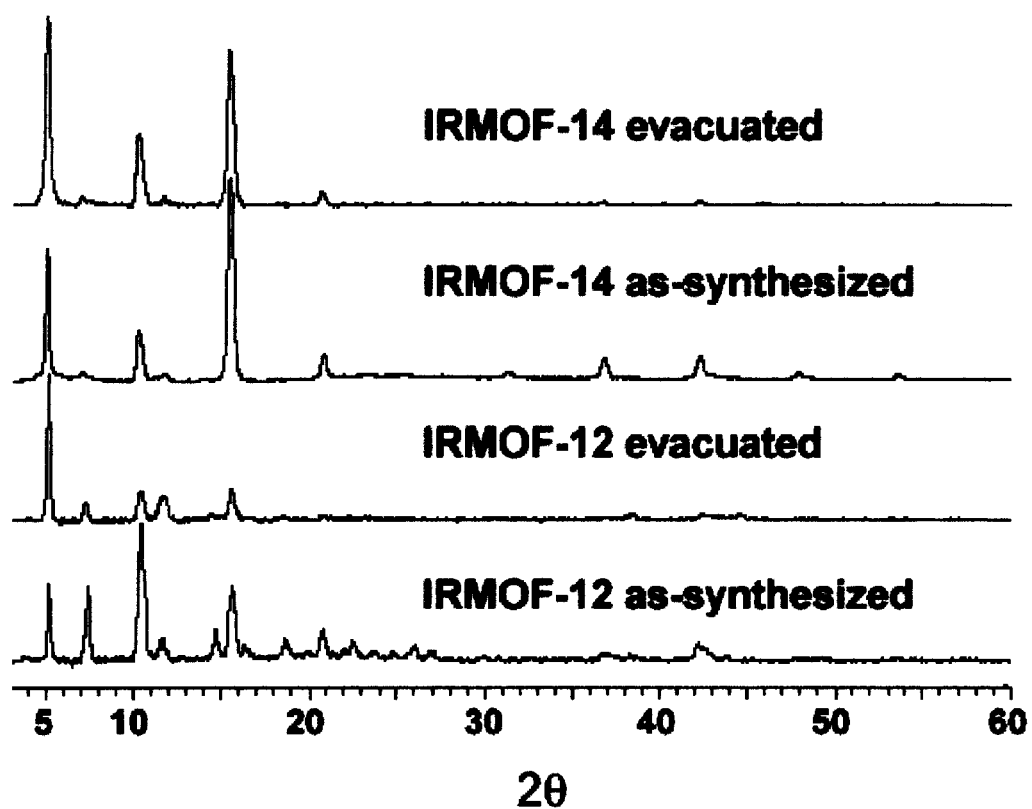

To show that the expanded frameworks, for which high free volume and low densities were calculated, can indeed maintain their permanent porosity in the absence of guests, the present inventors examined some of their sorption isotherms. It was indeed found that some of the most open members of this series (IRMOF-12 and 14) are porous, in that they exhibit behavior similar to that described above for IRMOF-6. In addition, they maintain their crystallinity in the absence of guests as evidenced by coincidence of the X-ray powder diffraction patterns of the as-synthesized material with those measured for the evacuated form of each of IRMOF-12 and 14 (FIG. 55D).

Prior to the present invention, the assembly of extended structures in a deliberate manner has been limited to hydrogen bonded guanidinium-sulfonate networks (V. A. Russell, C. C. Evans, W. J. Li and M. D. Ward, *Science* 276, 575 (1997)), and frameworks based on silver and nitrogen donor links (Y. H. Kiang, G. B. Gardner, S. Lee, Z. T. Xu and E. B. Lobkovsky, *J. Am. Chem. Soc.* 121, 8204 (1999)). In contrast, the present invention provides a unique approach that succeeds in the assembly of pre-designed rigid skeletal backbone structure and in imparting functionality and metric variation onto its pores, ultimately leading to functional materials capable of high uptake of gases and organic vapors. The intrinsic value of this design approach lies in the ability to control and direct the outcome of molecular assembly of extended networks. It is believed that the present invention ushers a new era in solid-state synthesis.

To further illustrate the inventive IRMOFs and methods for making them, the following examples are given. It is to be understood that these examples are provided for illustrative purposes and are not to be construed as limiting the scope of the present invention.

EXAMPLES

Preparation of IRMOF-1:

Method 1: 1,4-benzenedicarboxylic acid, H$_2$BDC, (0.070 g, 0.42 mmol) and zinc nitrate hexahydrate, Zn(NO$_3$)$_2$.6H$_2$O, (0.250 g, 0.84 mmol) were dissolved in 10 mL dimethylformamide, DMF. Then, 0.10 ml of hydrogen peroxide, H$_2$O$_2$, (30% aqueous) was added, followed by the addition of 0.10 mL of 50 times diluted dimethylamine (DMA) (40% aqueous) in DMF. The resultant mixture was diluted again 10 times with DMF. After several days (~7–10 days), a pure phase IRMOF-1 was formed.

In FIG. 1, a representation of a {100} layer of the IRMOF-1 framework is shown along the a-axis (C=grey; O=green). The ZnO$_4$ tetrahedra are indicated in purple. The frameworks interconnect to form a 3-D stable, porous crystalline structure.

Figure 2A:
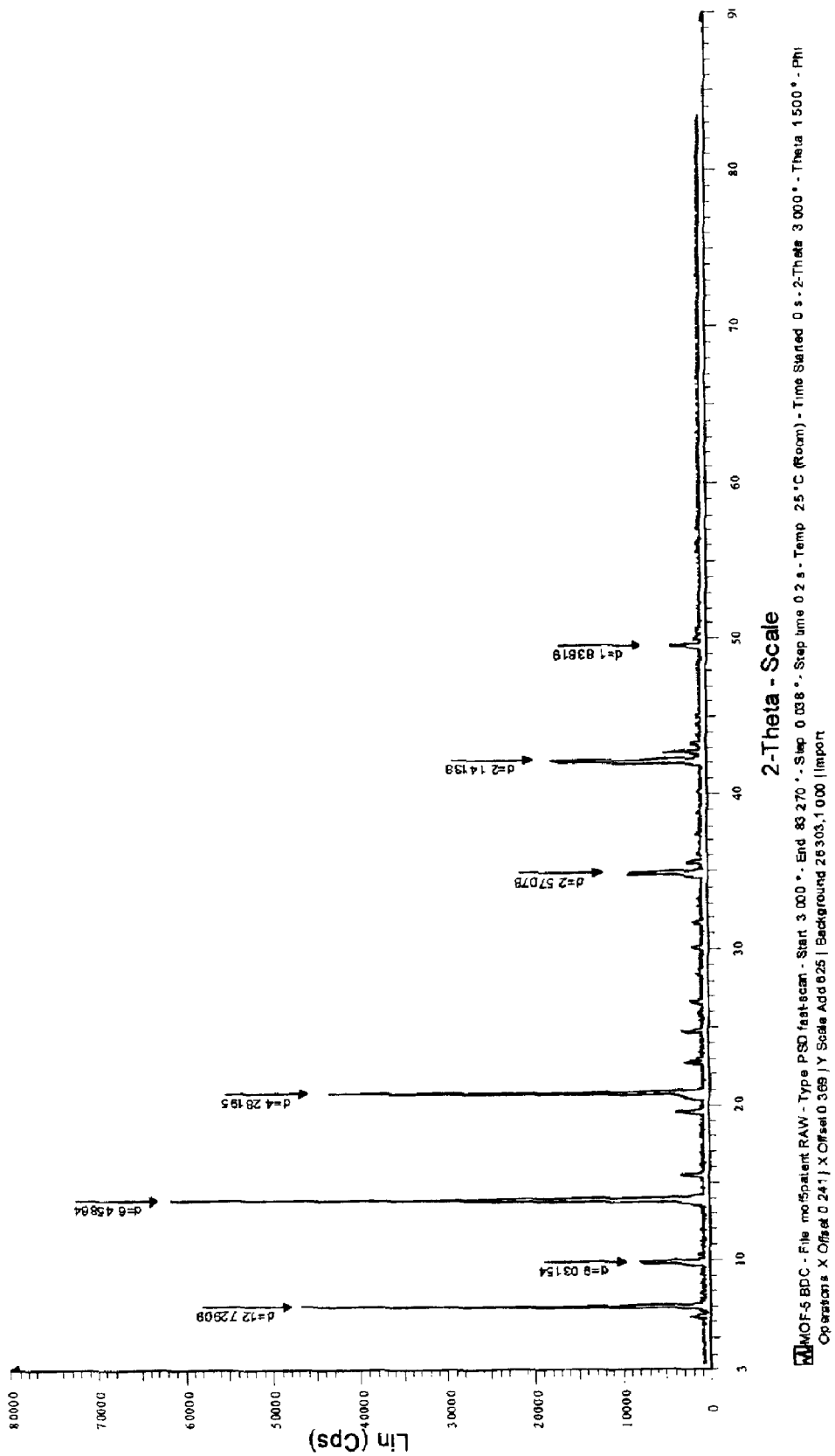
FIG. 2a is a graphic representation of an XRPD of IRMOF-1 for Method 1 of the present invention.

The purity of the as-synthesized compound was confirmed by X-ray powder diffraction (XRPD) pattern as shown in FIG. 2a.

Figure 2B:
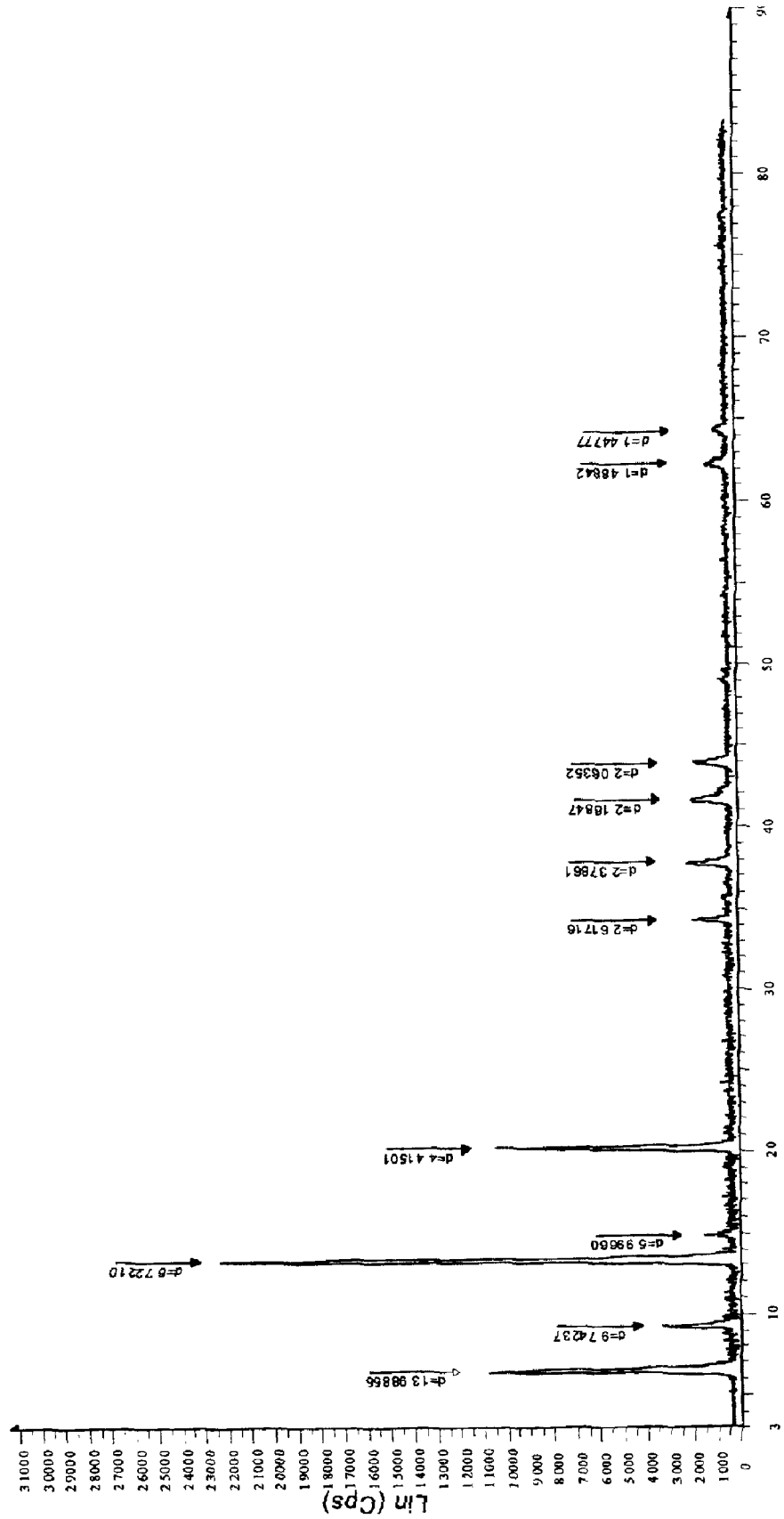
FIG. 2b is graphic representation of an XRPD of IRMOF-1 for Method 2 of the present invention.

Method 2: 1,4-benzenedicarboxylic acid, H$_2$BDC, (0.033 g, 0.20 mmol) and zinc nitrate tetrahydrate, Zn(NO$_3$)$_2$.4H$_2$O, (0.156 g, 0.60 mmol) were dissolved in 5 ml diethylformamide (DEF) and left at room temperature. After one week, the desired compound IRMOF-1 was formed in high yield (~85%). The purity of the as-synthesized compound was confirmed by X-ray powder diffraction (XRPD) pattern as shown in FIG. 2b.

Figure 2C:
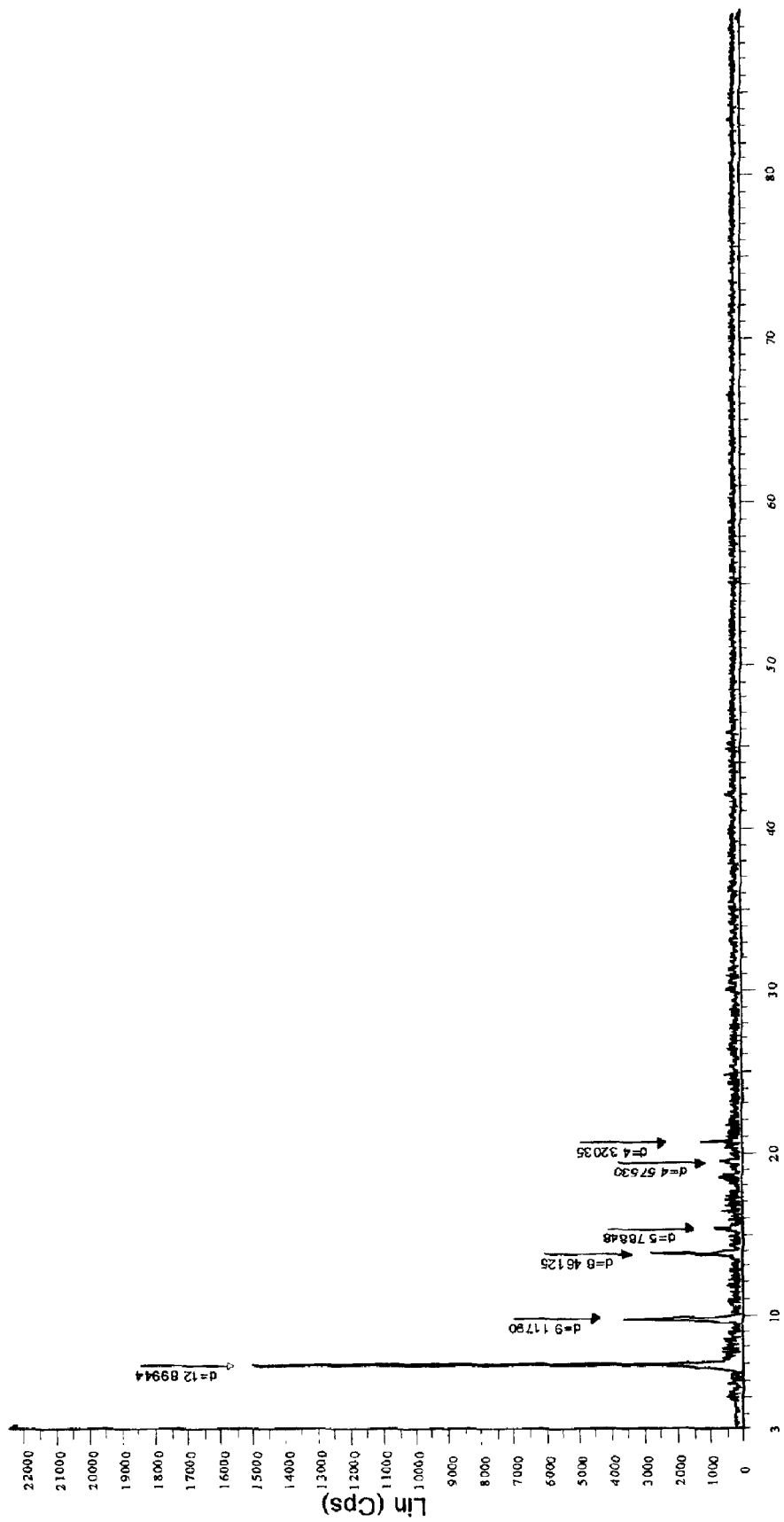
FIG. 2c is a graphic representation of an XRPD of IRMOF-1 for Method 3 of the present invention.
Figure 3:
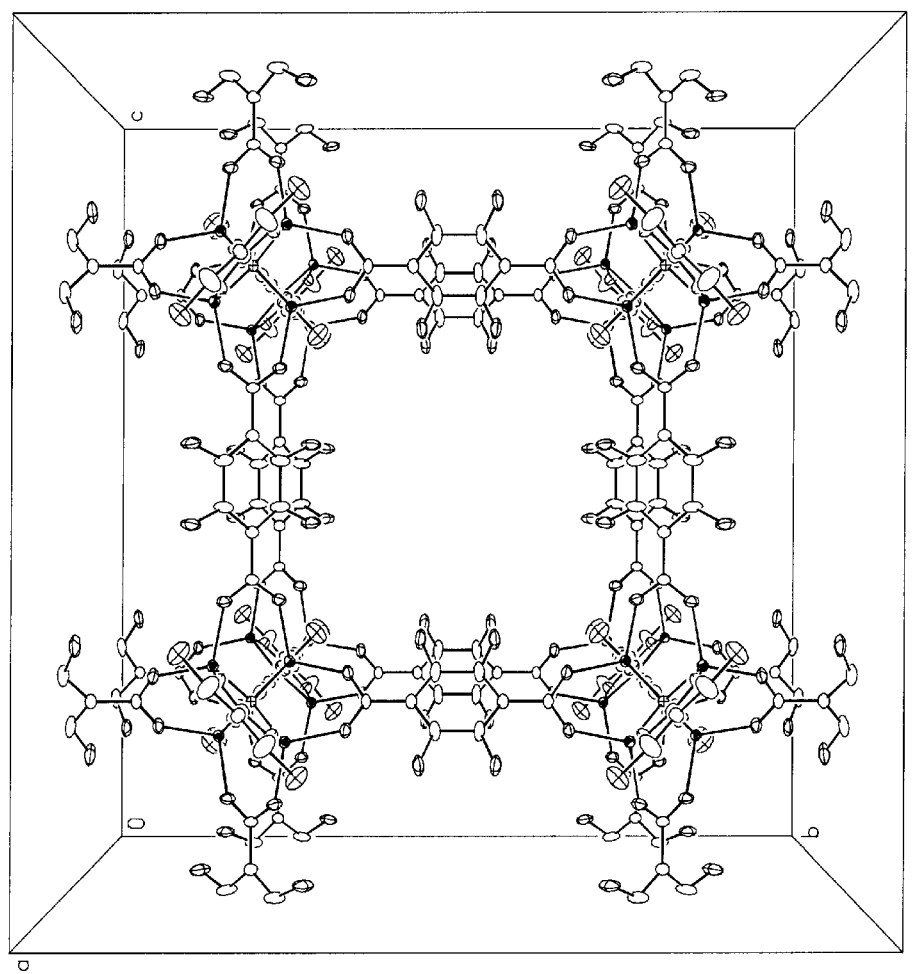
FIG. 3 is a diagrammatic representation of a crystal structure for IRMOF-3 of the present invention.

Method 3: An exact amount of 1,4-benzenedicarboxylic acid, H$_2$BDC, (0.033 g, 0.20 mmol) and zinc nitrate tetrahydrate, Zn(NO$_3$)$_2$.4H$_2$O, (0.156 g, 0.60 mmol) was dissolved in 5 ml diethylformamide, DEF, and placed in a Parr Teflon-lined stainless steel vessel (23 mL). The vessel was sealed and heated at a constant rate 2° C./min to 105° C. for 20 h and then cooled to room temperature at a rate of 1° C./min. The resultant compound was a pure IRMOF-1 as confirmed by X-ray powder diffraction (XRPD) pattern as shown in FIG. 2c.

Preparation of IRMOF-2:

Exact amount of 2-bromobenzenedicaroxylic acid, (o-BrBDCH$_2$) (0.040 g, 0.160 mmol), and zinc nitrate tetrahydrate, Zn(NO$_3$)$_2$.4H$_2$O, (0.156 g, 0.20 mmol), were dissolved in 15 mL diethylformamide, DEF, and placed in a Parr Teflon-lined stainless steel vessel (23 mL). The vessel was sealed and heated at a constant rate (2° C./min) to 95° C. for 20 h and then cooled to room temperature at a rate of 1° C./min. The resultant sample (67%) was filtered and washed with DEF (3×5 mL) yielding IRMOF-2.

Elemental analysis: C$_{59}$H$_{86}$Br$_3$O$_{20}$N$_7$Zn$_4$=Zn$_4$O(o-BrBDC)$_3$.(DEF)$_7$ Calcd C, 41.33; H, 5.06; N, 5.72. Found C, 41.23; H, 5.28; N, 5.59.

FT-IR (KBr, 3500–400 cm$^{-1}$): 3455 (br), 2982 (m), 2940 (w), 2874(w), 1668 (vs), 1647 (s), 1622 (s), 1556(w),

1485(m), 1449 (s), 1387 (vs), 1260 (m), 1214 (m), 1118 (w), 1042 (w), 827 (w), 776 (w), 741 (w), 665 (w), 542(w).

Preparation of IRMOF-3:

$Zn_4O(H_2NBDC)_3.(DEF)_x$ (IRMOF-3): A mixture of diethylformamide and ethanol $DEF/C_2H_5OH$: 9/3 ml containing 2-amino 1,4 benzenedicarboxylic acid, $H_2BDCNH_2$, (0.036 g, 0.20 mmol) and zinc nitrate tetrahydrate, $Zn(NO_3)_2.4H_2O$, (0.156 g, 0.60 mmol) was placed in a Parr Teflon-lined stainless steel vessel (23 mL). The vessel was sealed and heated at a constant rate 2° C./min to 105° C. for 20 h and then cooled to room temperature at a constant rate of 1° C./min. The resultant product, IRMOF-3 (90%) was filtered and washed with DEF/ethanol mixture (3×5 mL).

IRMOF-3 is insoluble in water and all common organic solvents such as ethanol, acetonitrile, tetrahydrofuran, chloroform, dichloromethane, acetone, N,N'-dimethylformamide, and N,N'-diethylformamide.

Figure 4A:
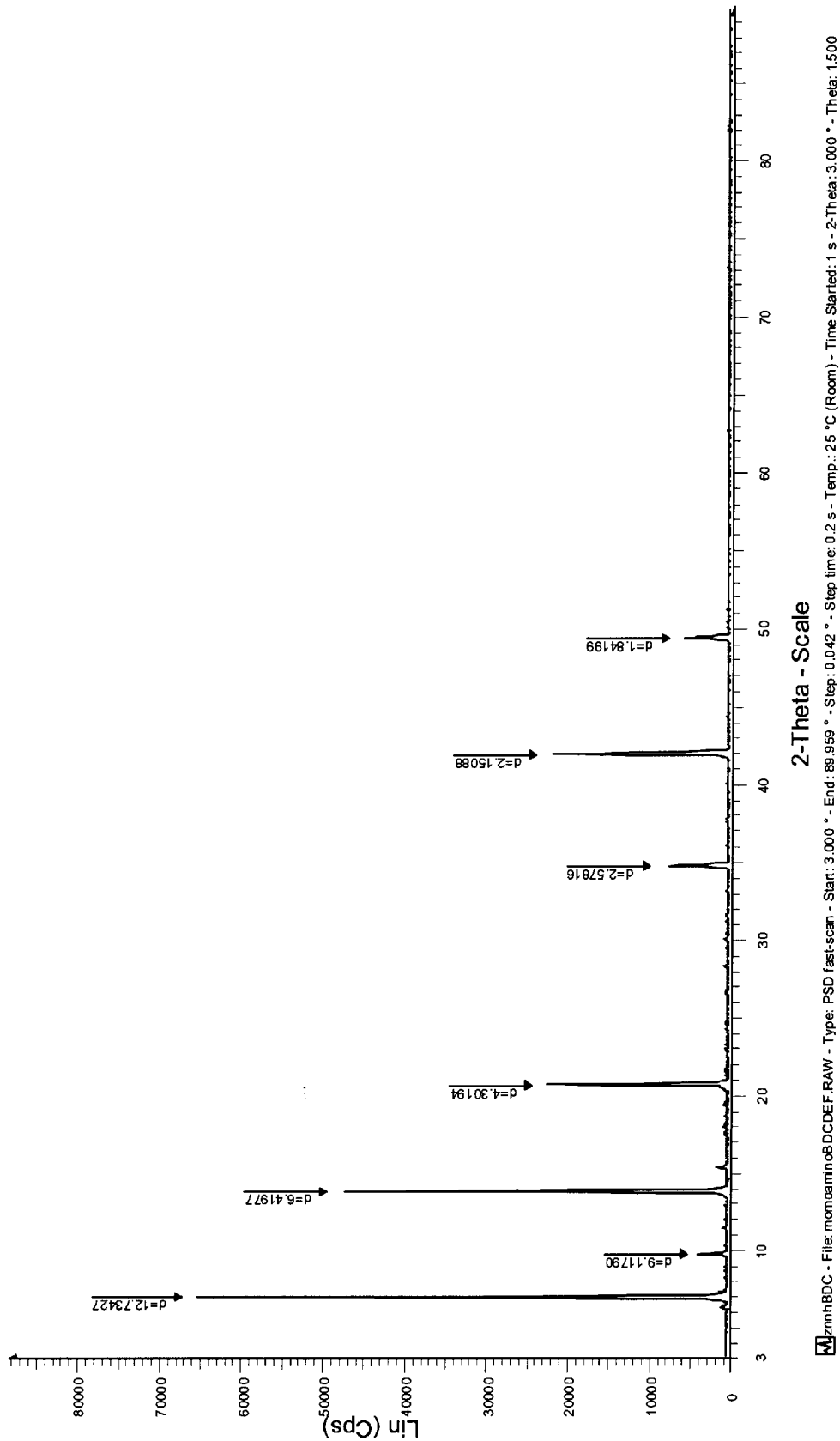
FIG. 4a is a graphic representation of an XRPD of IRMOF-3 of the present invention.
Figure 4B:
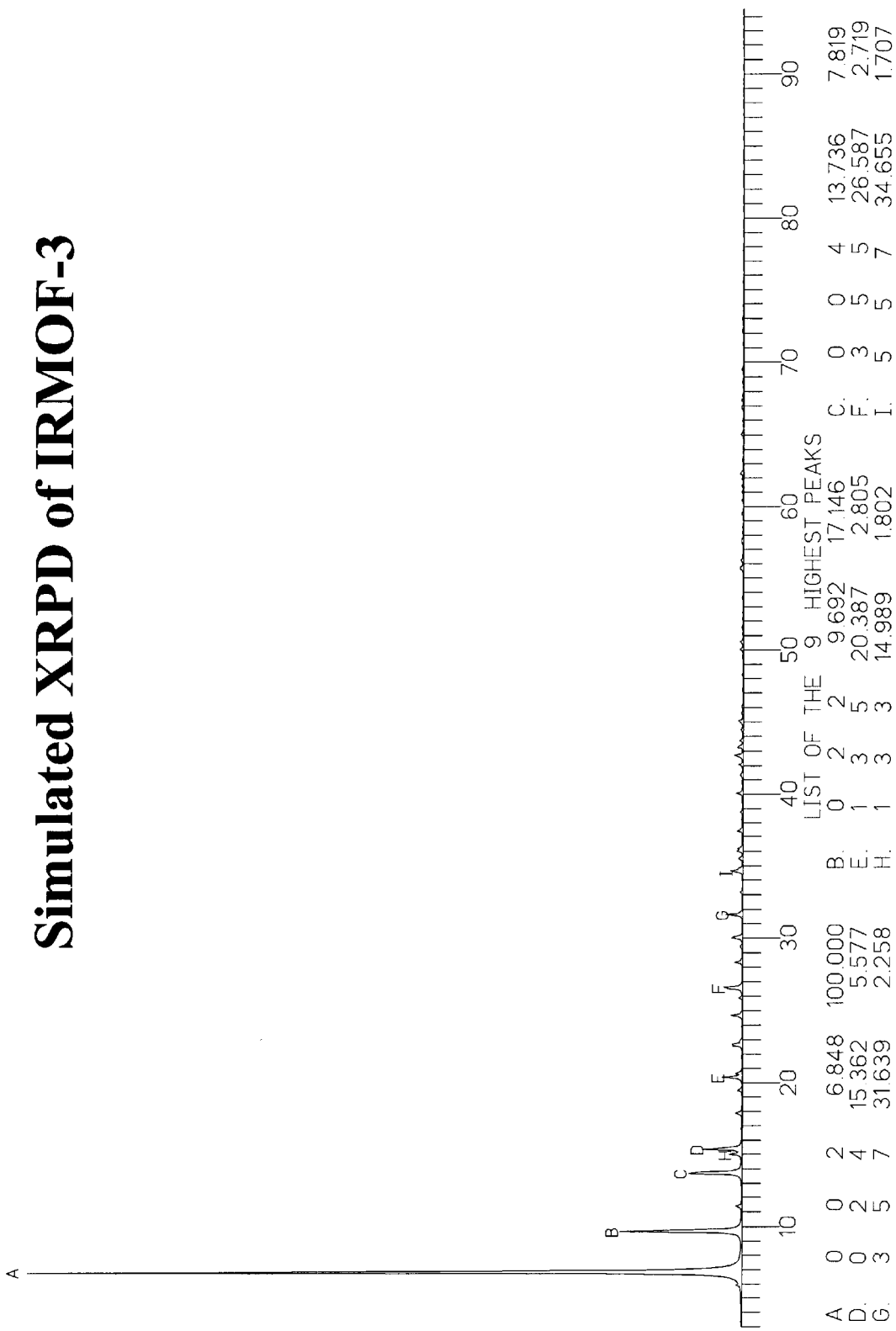
FIG. 4b is a graphic representation of a simulated XRPD of IRMOF-3.
Figure 5:
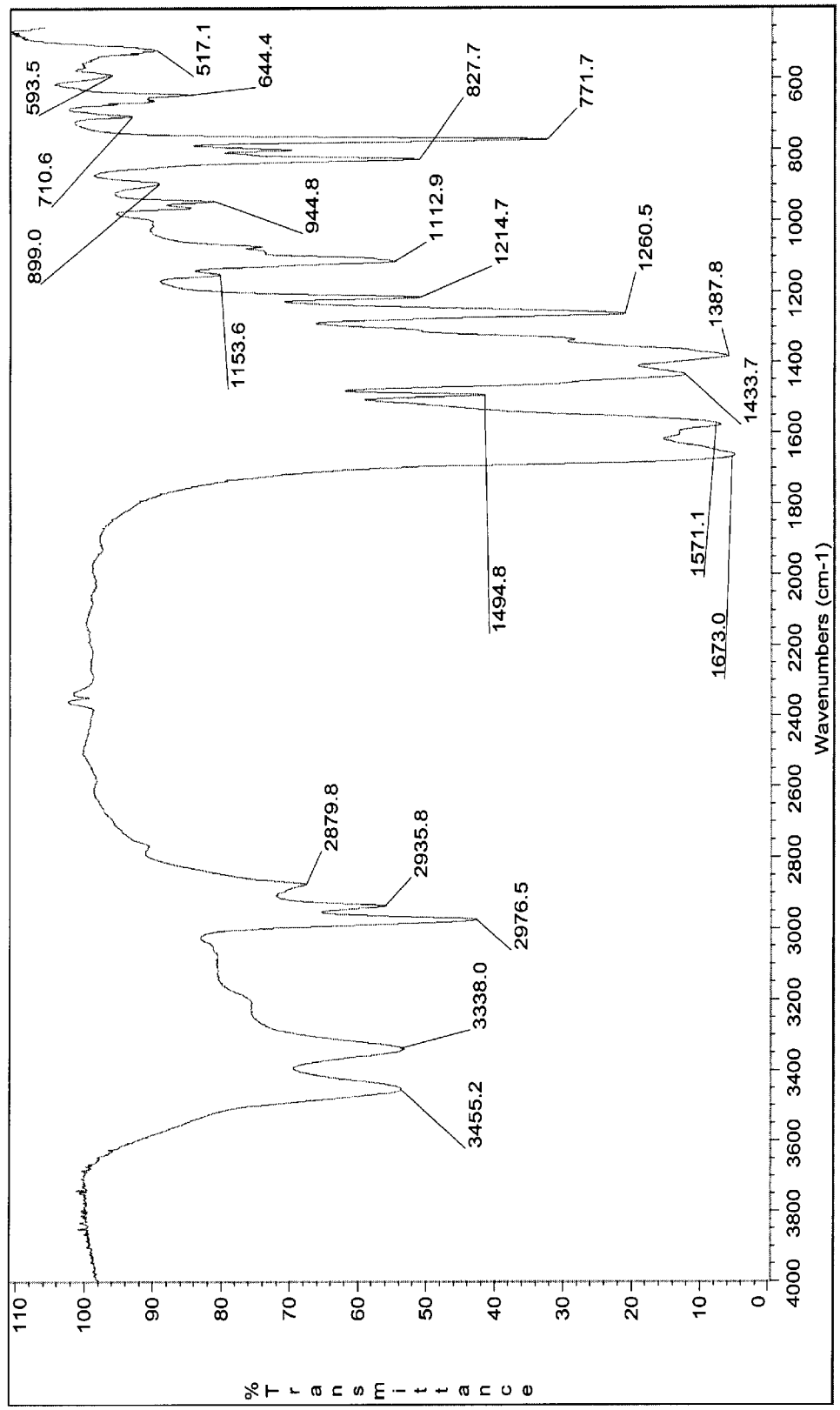
FIG. 5 is a graphic representation of an InfraRed spectrum for IRMOF-3 of the present invention.

Phase purity of the bulk products was confirmed by comparison of the observed X-ray powder diffraction (XRPD) pattern shown in FIG. 4a, and the calculated X-ray powder diffraction (XRPD) pattern shown in FIG. 4b simulated from the single-crystal structure data of IRMOF-3.

Elemental analysis for IRMOF-3: $C_{59}H_{92}O_{20}N_{10}Zn_4=Zn_4O(H_2NBDC)_3.(DEF)_7$ Calcd C, 46.31; H, 6.04; N, 9.20. Found C, 46.59; H, 6.04; N, 9.24.

Infra-Red spectra for IRMOF-3 (FIG. 5):

FT-IR for IRMOF-3 (KBr, 3500–400 $cm^{-1}$): Infrared spectra characteristic peaks 3455 (br), 3338 (br), 2976 (m), 2936 (w), 2879 (w), 1673 (vs), 1571 (s), 1495 (w), 1433 (s), 1387 (vs), 1260 (m), 1214 (m), 1153 (w), 1113 (w), 944 (w), 899 (w), 827 (w), 782 (m), 710 (w), 717 (m), 644 (w), 593 (w), 517 (w).

Figure 6:
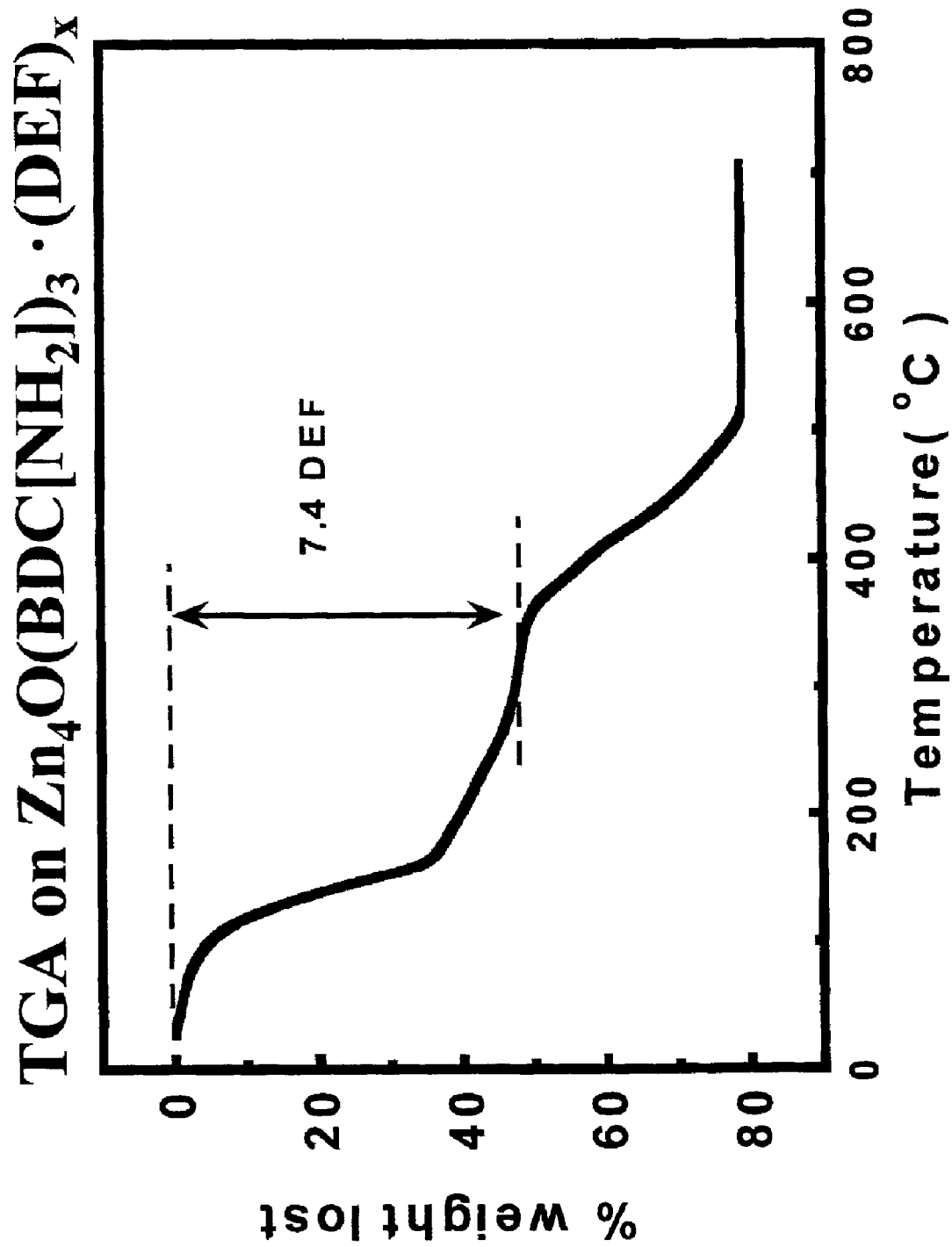
FIG. 6 is a graphic representation of TGA on $Zn_4O(BDC[NH_2])_3.(DEF)_x$ of the present invention.
Figure 7:
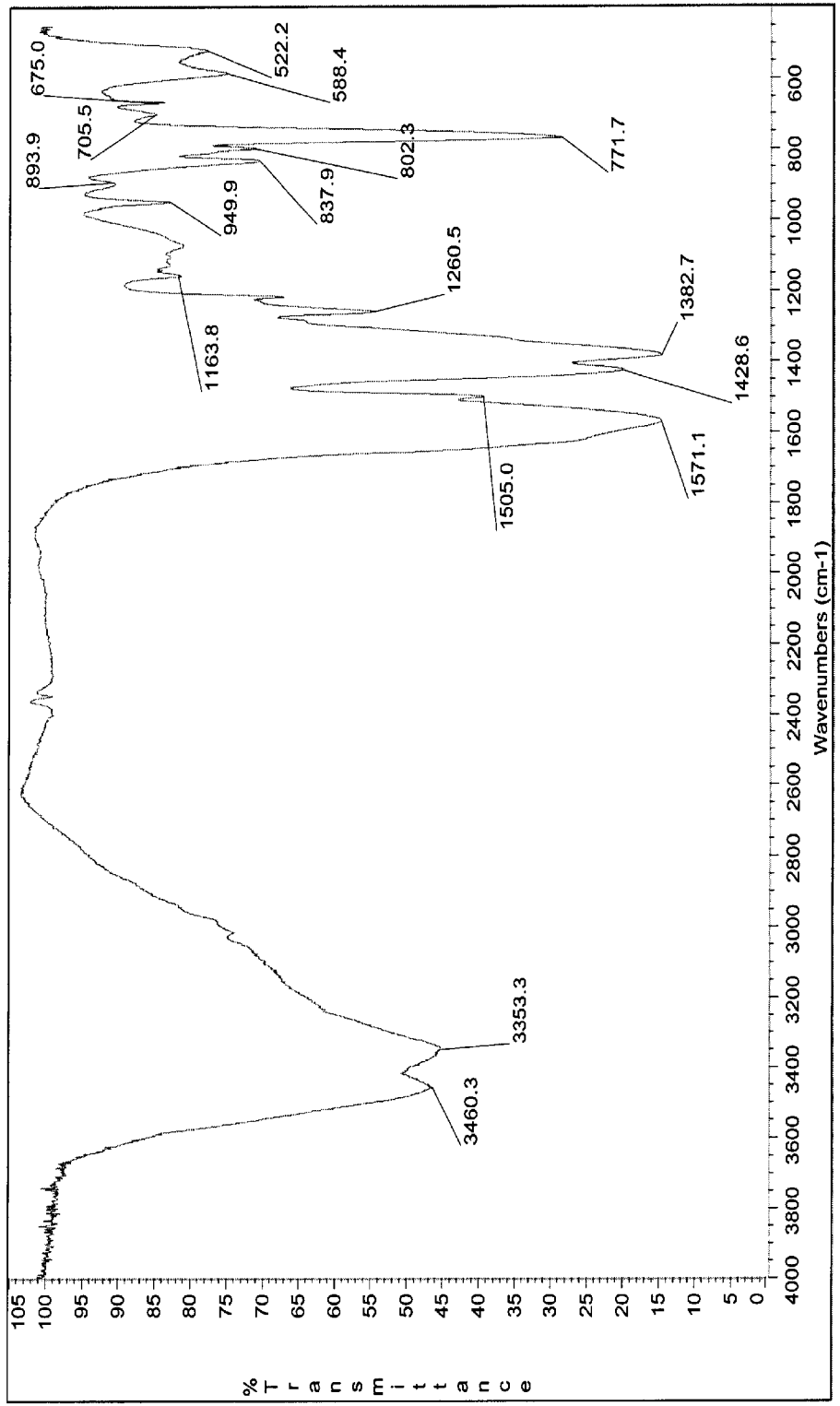
FIG. 7 is a graphic representation of an InfraRed spectrum for $Zn_4O(BDC[NH_2])_3.(CHCl_3)_x$ of the present invention.

Thermogravimetric Analysis for IRMOF-3 (FIG. 6): A crystalline sample was heated at a constant rate, 5° C./min, under nitrogen flow (20 ml/min) from 30 to 700° C. As shown in FIG. 6, two weight loss steps were observed below 350° C.: the first can be attributed to the loss of free DEF (~6 DEF), and the second, occurring between 150 and 350° C., to the desorption of the hydrogen bound DEF. In the last step, occurring between 350 and 500° C., the framework decomposes.

Preparation of IRMOF-3 with chloroform molecules as guests, $Zn_4O(H_2NBDC)_3.(CHCl_3)_x$: A fresh as-synthesized sample was immersed in chloroform solution. The solution was twice refreshed with chloroform and left overnight for a complete exchange. The exchanged compound conserves its overall integrity as shown by retention of the original XRPD pattern. IR, elemental analysis, and thermal gravimetric analysis confirmed the completion of the exchange as shown by the data below:

Elemental analysis for $Zn_4O(H_2NBDC)_3.(CHCl_3)_x$: $C_{30.8}H_{21.8}O_{13}N_3Cl_{6.8}Zn_4=Zn_4O(H_2NBDC)_3.(CHCl_3)_{6.8}$ Calcd C, 23.00; H, 1.38; N, 2.65. Found C, 22.92; H, 1.53; N, 2.67.

FT-IR for $Zn_4O(H_2NBDC)_3.(CHCl_3)_x$ (KBr, 3500–400 $cm^{-1}$) (FIG. 7): 3460 (br), 3353 (br), 1571 (s), 1505 (w), 1428 (s), 1383 (vs), 1260 (w), 1163 (w), 950 (w), 893 (w), 837 (w), 802 (w), 717 (m), 705 (w), 675 (w), 588 (w), 522 (w). The very strong peak at 1673 $cm^{-1}$ disappeared as expected due to the full exchange of diethylformamide, DEF, with the chloroform. $\nu_{C=O}$ (DEF)=1673 $cm^{-1}$.

Figure 8:
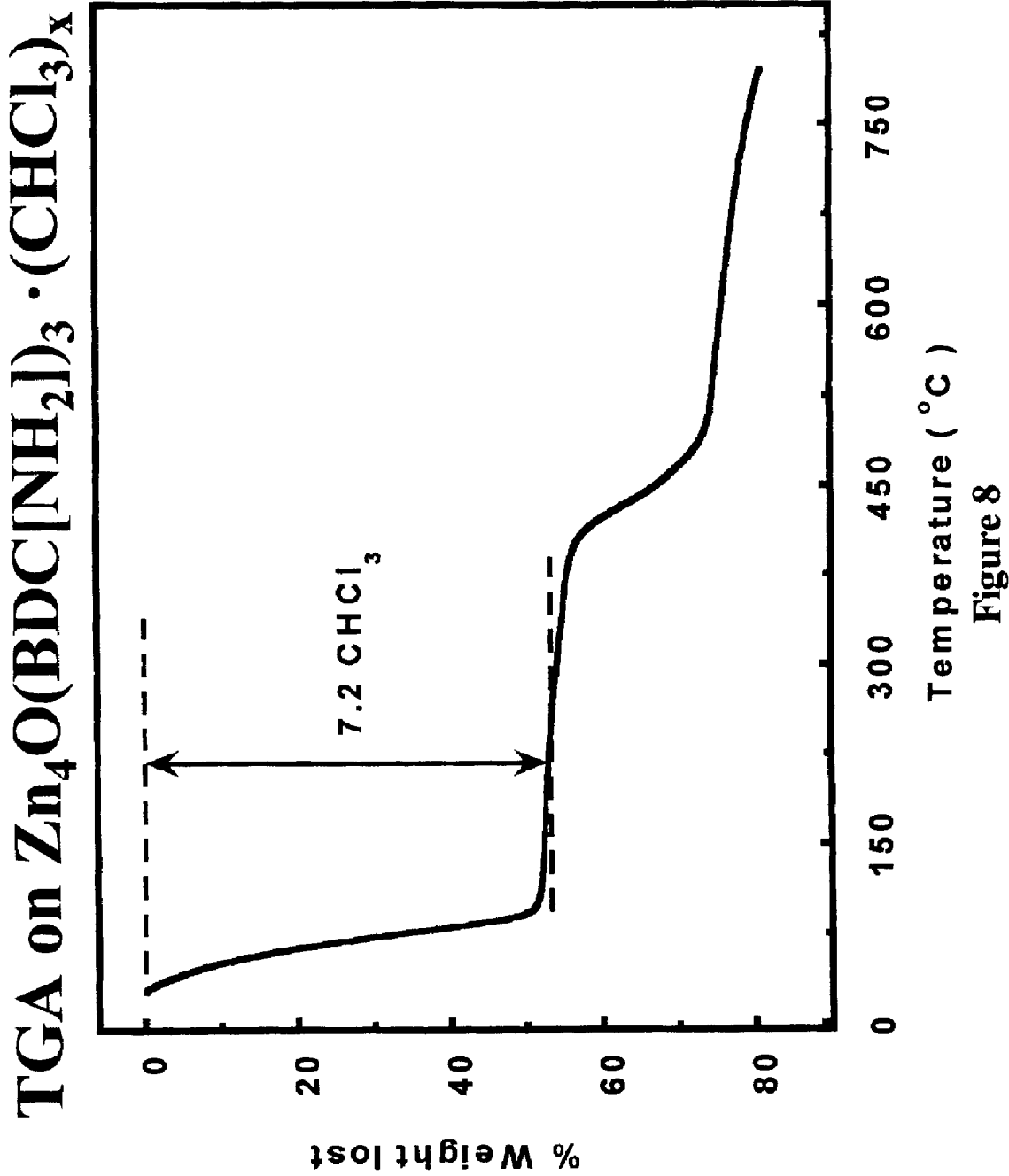
FIG. 8 is a graphic representation of TGA $Zn_4O(BDC[NH_2])_3.(CHCl_3)_x$ of the present invention.

Thermogravimetric analysis for $Zn_4O(H_2NBDC)_3.(CHCl_3)_x$ (FIG. 8): The exchanged crystalline sample was heated at a constant rate, 5° C./min, under nitrogen flow (20 ml/min) from 30 to 760° C. As shown in FIG. 8, a sharp weight loss was observed below 80° C. corresponding to the loss of the chloroform guest molecules (~7.2 $CHCl_3$). In the last step, occurring between 380 and 500° C., the framework decomposes.

Porosity Studies for $Zn_4O(H_2NBDC)_3$ IRMOF-3:

As observed from thermogravimetric analysis (TGA) the exchanged sample can lose all of the chloroform guest molecules under a flow of nitrogen at a relatively low temperature (~80° C.), whereas diethylformamide, DEF, requires higher temperatures for removal. As a consequence, we opted to choose the exchanged framework for the sorption studies.

An exact amount of the exchanged sample, $Zn_4O$ $(H_2NBDC)_3.(CHCl_3)_x$, was introduced into a Cahn C-1000 microbalance. The compound was evacuated at room temperature and $P=10^{-5}$ torr. All the chloroform guest molecules were removed in a short period of time (~15 minutes) as confirmed by no additional weight change upon exposing the sample to vacuum over night or under extended heat (~150° C.).

Figure 9:
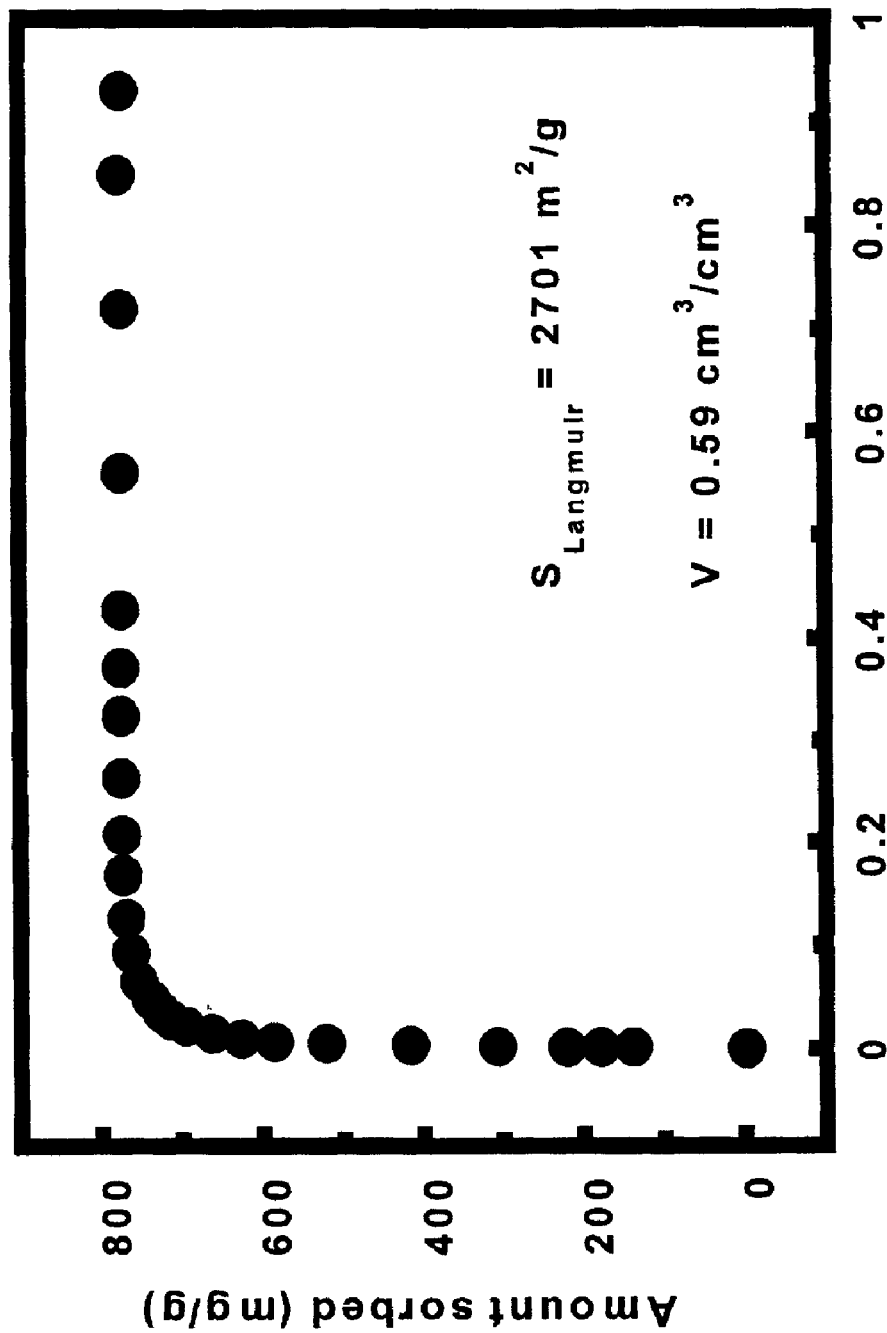
FIG. 9 is a graphic representation of an $N_2$ Sorption on IRMOF-3 @ 77K of the present invention.

To confirm the stability and porosity of the evacuated framework, the nitrogen sorption at 78K was monitored by introducing different increments of nitrogen gas to the sample chamber. As shown in FIG. 9, the nitrogen sorption isotherm is a Type I isotherm and fully reversible, characteristic of a microporous material (<2.0 nm). The plateau was reached at relatively low pressure with no additional uptake at relatively medium pressures (near condensation pressure $P/P_0$~0.5), confirming the homogeneity of the pores and the absence of any mesoroporosity or macroporosity.

By applying the Langmuir and DR equations, the Langmuir surface and pore volume respectively were estimated: $S_{langmuir}=2701$ $m^2/g$ and $Vp=0.58$ $cm^3/cm^3$.

Figure 10:
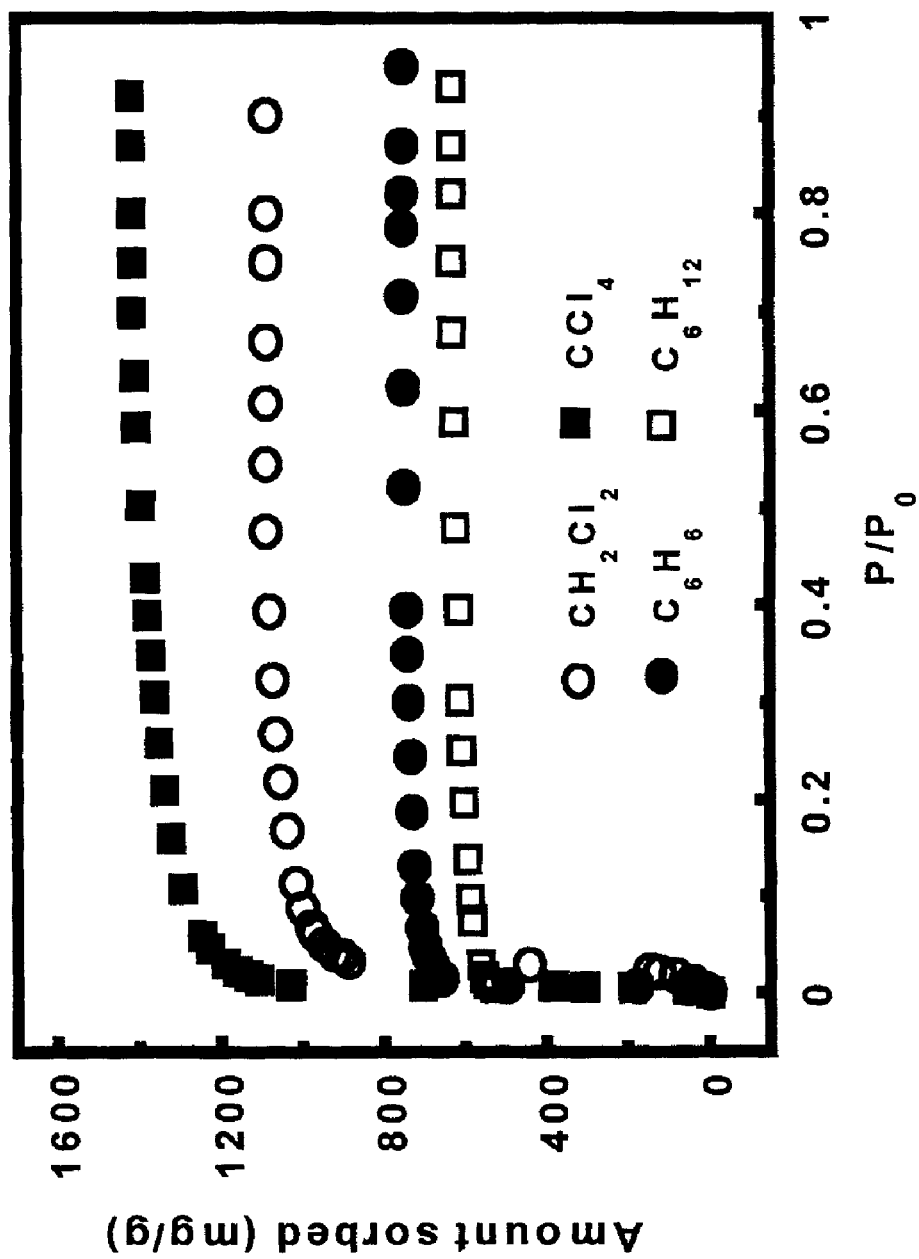
FIG. 10 is a graphic representation of an organic vapor sorption at RT on IRMOF-3 of the present invention.
Figure 11:
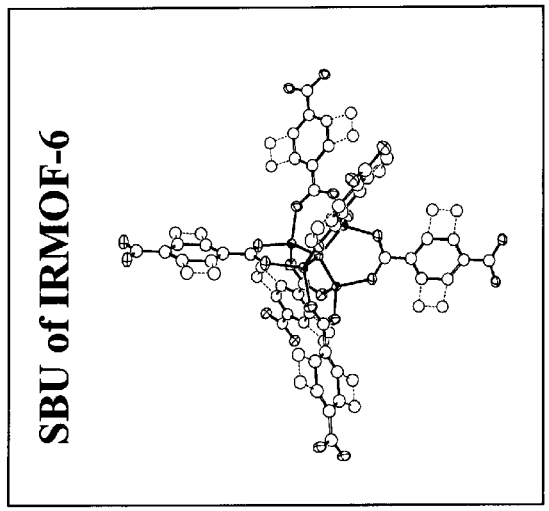
FIG. 11 is a diagrammatic representation of a crystal structure for IRMOF-6 of the present invention.
Figure 11:
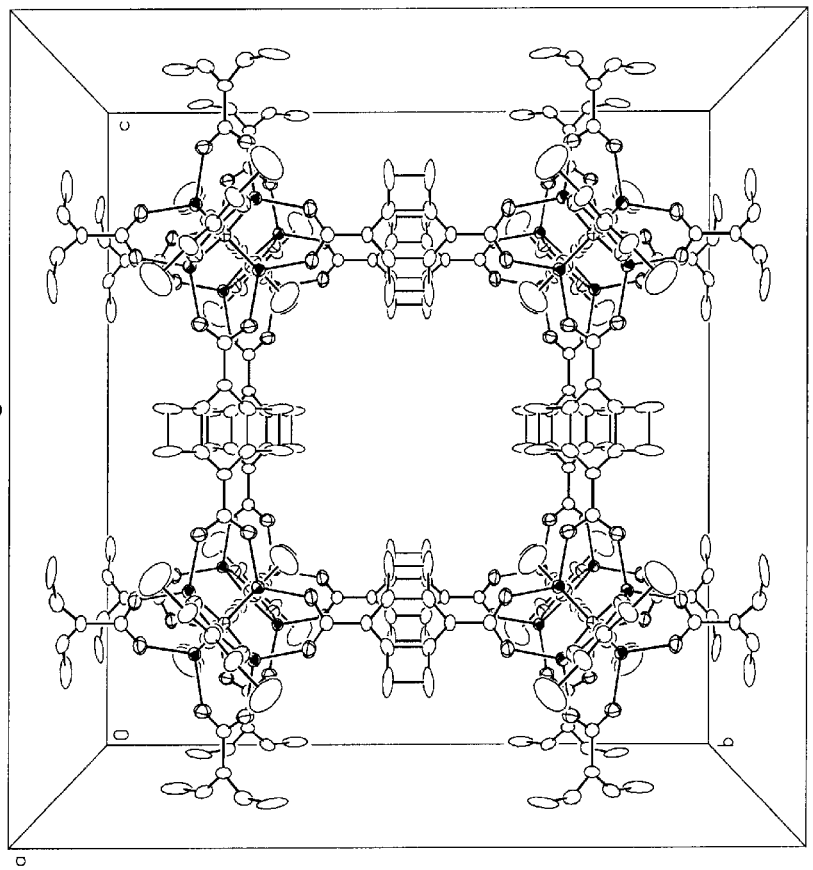

The evacuated sample was also exposed to different organic vapors such as dichloromethane $CH_2Cl_2$, benzene $C_6H_6$, carbon tetrachloride $CCl_4$ and cyclohexane $C_6H_{12}$. All the resultant isotherms were Type I and reversible as shown in FIG. 10. The data are summarized in Table 1, and they indicate that, regardless of the sorbed guest, the pore volumes converge to the same values (0.52–0.59 $cm^3/cm^3$): final proof of the homogeneity of the pores.

The resultant cubic IRMOF-3 crystals were collected and fully characterized. The crystallographic parameters and a picture of the framework are summarized in FIG. 3. The elemental analysis confirms the composition as discussed above, and the Infrared spectrum confirms that the carboxylates are fully deprotonated. The overlap of the observed and simulated XRPD confirms the purity of the sample. Diethylformamide molecules occupied the void spaces in the porous structure of IRMOF-3. The DEF guest molecules can be removed from the pores under extended vacuum or by heating the sample as shown in FIG. 6. The DEF guest molecules can also be fully exchanged with a volatile molecule, such as chloroform, as proven by the data above. To confirm that IRMOF-3 maintains its structure and mainly its porosity upon removing the guest molecules, sorption studies were carried out on the fully evacuated IRMOF-3. As shown in FIG. 9, the isotherm is a type I isotherm characteristic of a microporous material (Nitrogen sorption isotherm is a universal and powerful tool to characterize porous material). The data summarized in Table 1 prove that IRMOF-3 has homogeneous porosity and is able to sorb different guest molecules. It is believed that the stability of the framework may primarily be due to the stability of the $M_4O(CO_2)_6$ cluster (secondary building unit).

Preparation of IRMOF-4:

An exact amount of 2,5-propyl-benzenedicaroxylic acid, ($[OC_3H_7]_2BDCH_2$) (0.032 g, 0.111 mmol), and zinc nitrate tetrahydrate, $Zn(NO_3)_2.4H_2O$, (0.126 g, 0.48 mmol), were dissolved in 10 ml diethylformamide, DEF, placed in a Parr Teflon-lined stainless steel vessel (23 mL). The vessel was sealed and heated at a constant rate (2° C./min) to 95° C. for 36 h and then cooled to room temperature at a rate of 1° C./min. The resultant sample was filtered and washed with DEF (3×5 mL) yielding IRMOF-4.

Elemental analysis: $C_{77}H_{125}O_{26}N_7Zn_4=Zn_4O(BrBDC)_3 \cdot (DEF)_7$ Calculated C, 50.64; H, 6.90; N, 5.37. Found C, 50.79; H, 7.20; N, 5.61.

FT-IR (KBr, 3500–400 cm$^{-1}$): 3455 (br), 2976 (m), 2941 (w), 2936 (w), 2879 (w), 1663 (s), 1607 (vs), 1495 (w), 1423 (vs), 1494 (w), 1393 (s), 1270 (m), 1210 (m), 1118 (w), 1067 (w), 980 (w), 802 (m), 746 (w), 644 (w), 552 (w).

Preparation of IRMOF-5:

An exact amount of 2,5-pentyl-benzenedicaroxylic acid, ([OC$_5$H$_{11}$]$_2$BDCH$_2$) (0.044 g, 0.131 mmol), and zinc nitrate tetrahydrate, Zn(NO$_3$)$_2$.4H$_2$O, (0.130 g, 0.50 mmol), were dissolved in 10 ml diethylformamide, DEF, and placed in a Parr Teflon-lined stainless steel vessel (23 mL). The vessel was sealed and heated at a constant rate (2° C./min) to 95° C. for 36 h and then cooled to room temperature at a rate of 1° C./min. The resultant sample was filtered and washed with DEF (3×5 mL) yielding IRMOF-5.

Elemental analysis: $C_{71}H_{111}O_{24}N_5Zn_4=Zn_4O$ ([OC$_5$H$_{11}$]$_2$ BDC)$_3$.(DMF)$_1$(DEF)$_4$ Calculated C, 50.75; H, 6.86; N, 4.21. Found C, 50.04; H, 6.86; N, 4.21.

FT-IR (KBr, 3500–400 cm$^{-1}$): 3445 (br), 2961 (m), 2931 (m), 2865 (w), 1658(s), 1607 (vs), 1495 (w), 1429 (vs), 1388 (s), 1281 (w), 1200 (m), 1052 (w), 1006 (w), 904 (w), 807 (m), 761 (w), 731(w), 665 (w), 552 (w).

Preparation of IRMOF-6:

$Zn_4O([C_2H_4]BDC)_3.(DEF)_x$ (IRMOF-6): cyclobutene 1,4-benzenedicarboxylic acid, H$_2$BDC[C$_2$H$_4$], (0.045 g, 0.20 mmol) and zinc nitrate tetrahydrate, Zn(NO$_3$)$_2$.4H$_2$O, (0.156 g, 0.60 mmol) were dissolved in 12 mL diethylformamide, DEF and placed in a Parr Teflon-lined stainless steel vessel (23 mL). The vessel was sealed and heated at a constant rate (2° C./min) to 105° C. for 20 h and then cooled to room temperature at a rate of 1° C./min. The resultant sample (92%), IRMOF-2, was filtered and washed with DEF (3×5 mL). It is insoluble in water and all common organic solvents such as ethanol, acetonitrile, tetrahydrofuran, chloroform, dichloromethane, acetone, N,N'-dimethylformamide, and N,N'-diethylformamide.

Figure 12A:
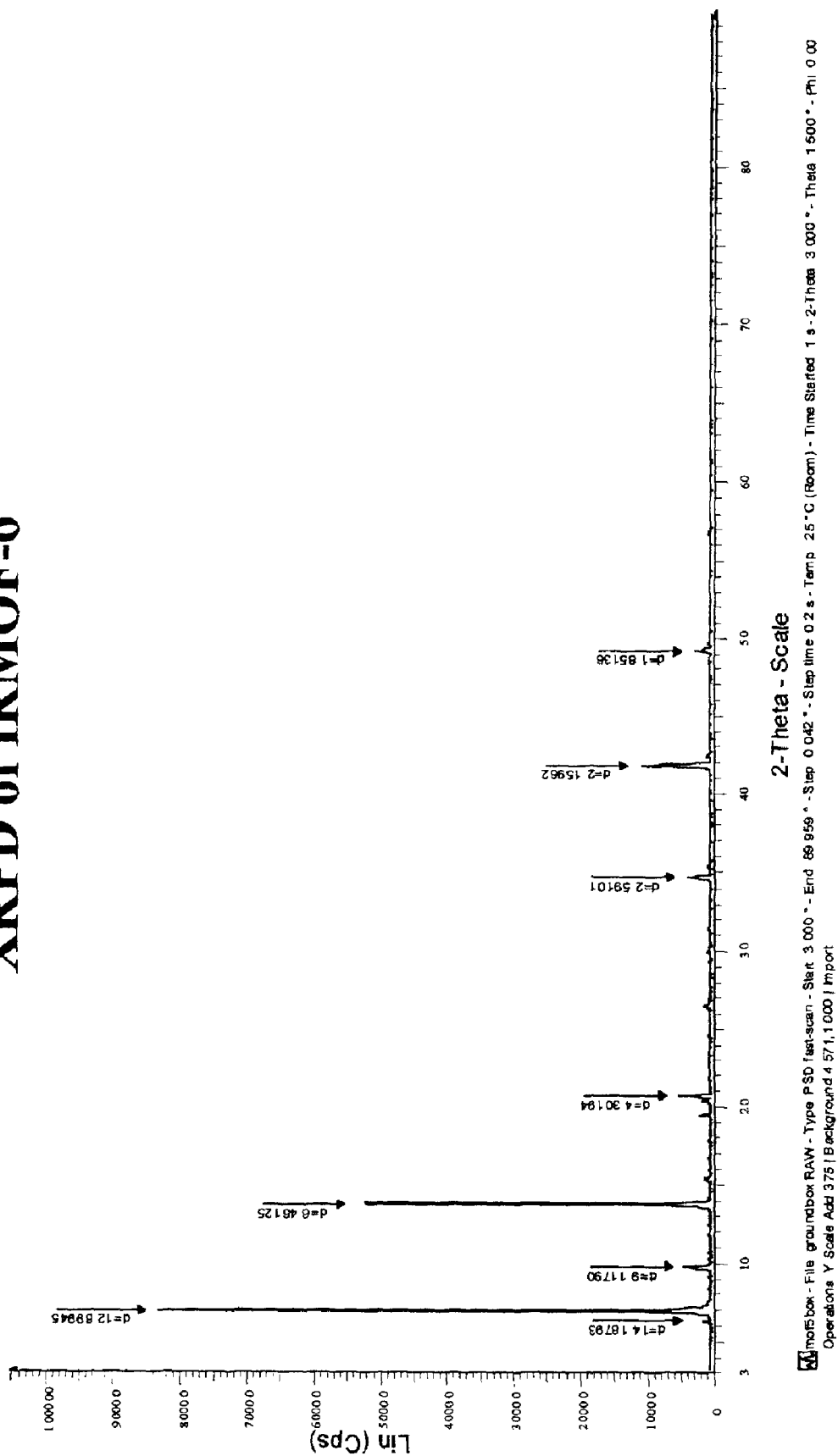
FIG. 12a is a graphic representation of an XRPD of IRMOF-6 of the present invention.
Figure 12B:
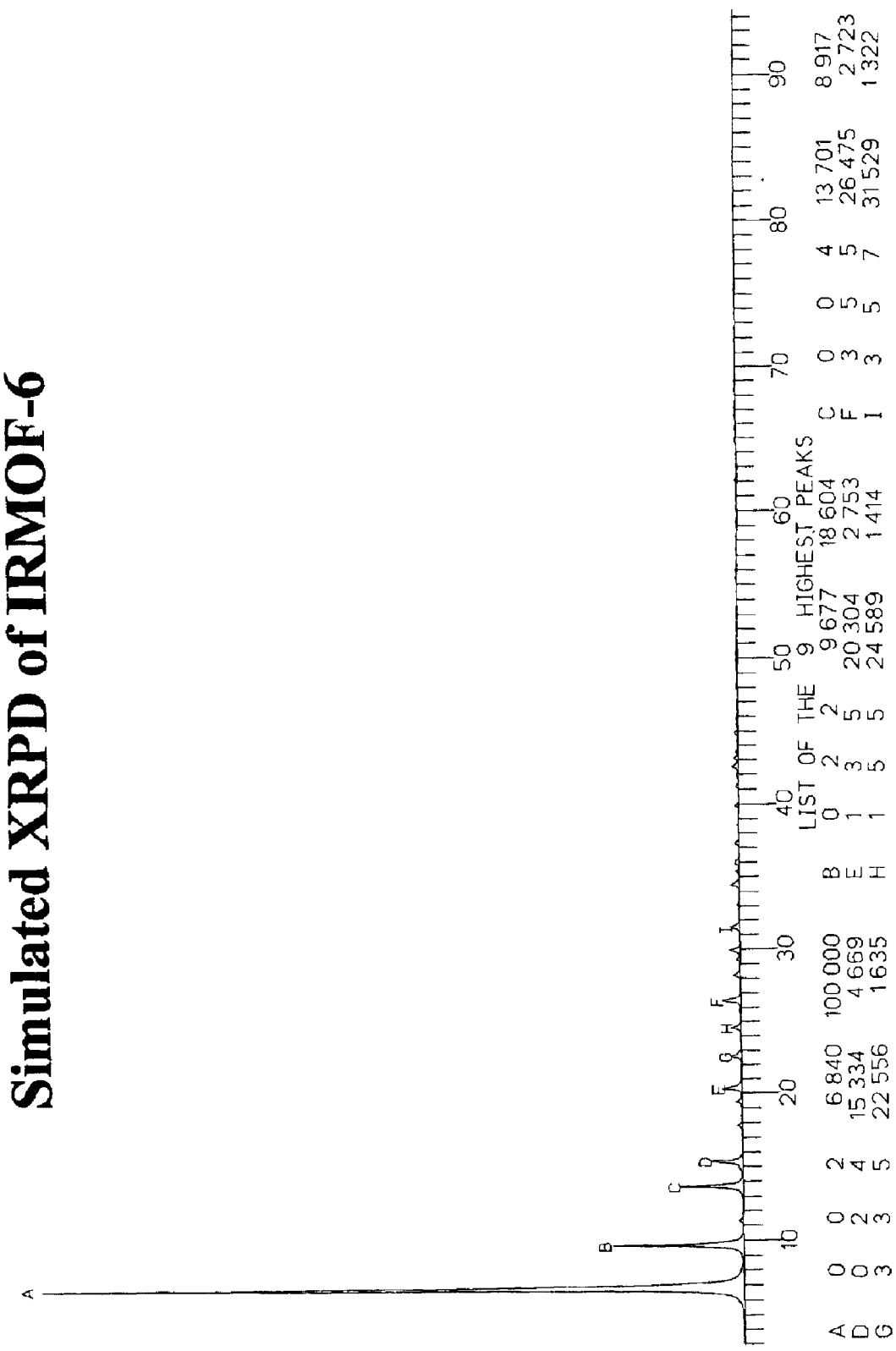
FIG. 12b is a graphic representation of a simulated XRPD of IRMOF-6 of the present invention.
Figure 13:
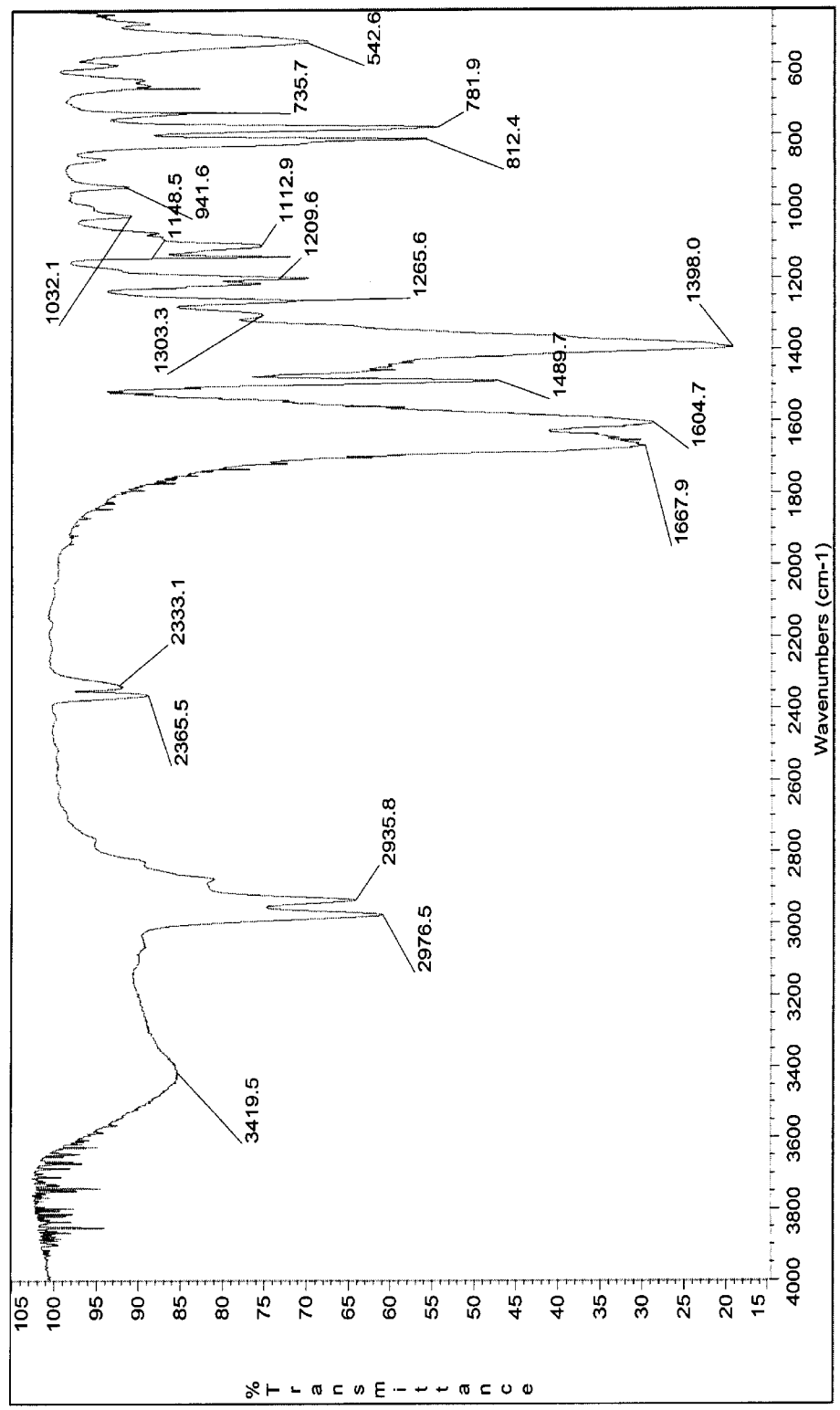
FIG. 13 is a graphic representation of an InfraRed spectrum for IRMOF-6.

Phase purity of the bulk product was confirmed by comparison of the observed X-ray powder diffraction (XRPD) pattern, shown in FIG. 12a, and the calculated X-ray powder diffraction pattern, shown in FIG. 12b, simulated from the single-crystal structure data of IRMOF-2, $Zn_4O([C_2H_4]BDC)_3.(DEF)_x$.

Elemental analysis for IRMOF-6: $C_{57.5}H_{78.5}O_{18.5}N_{5.5}Zn_4=Zn_4O([C_2H_4]BDC)_3.(DEF)_{5.5}$ Calculated C, 46.77; H, 5.22; N, 5.86. Found C, 46.75; H, 5.45; N, 5.19.

Infra-Red spectra for IRMOF-6 (FIG. 13):

FT-IR for IRMOF-6 (KBr, 3500–400 cm$^{-1}$): 3419 (br), 2976 (m), 2936 (m), 2365 (w), 2340 (w), 1668 (s), 1605 (vs), 1489 (m), 1398 (vs), 1303 (w), 1265 (w), 1112 (w), 941 (w), 812 (m), 782 (m), 735 (w), 542 (m).

Figure 14:
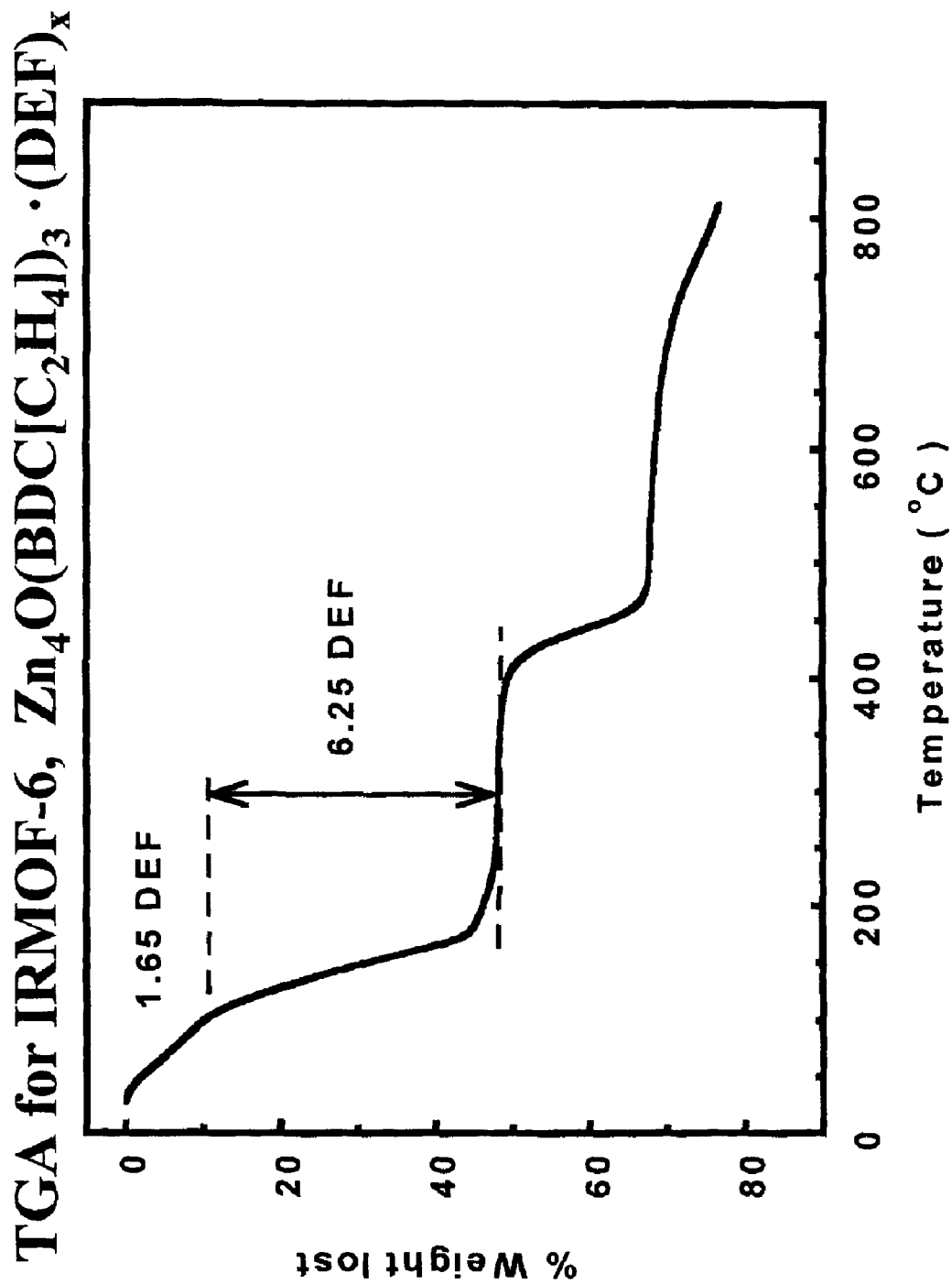
FIG. 14 is a graphic representation of a TGA for IRMOF-6, $Zn_4O(BDC[C_2H_4])_3.(DEF)_x$ of the present invention.
Figure 15:
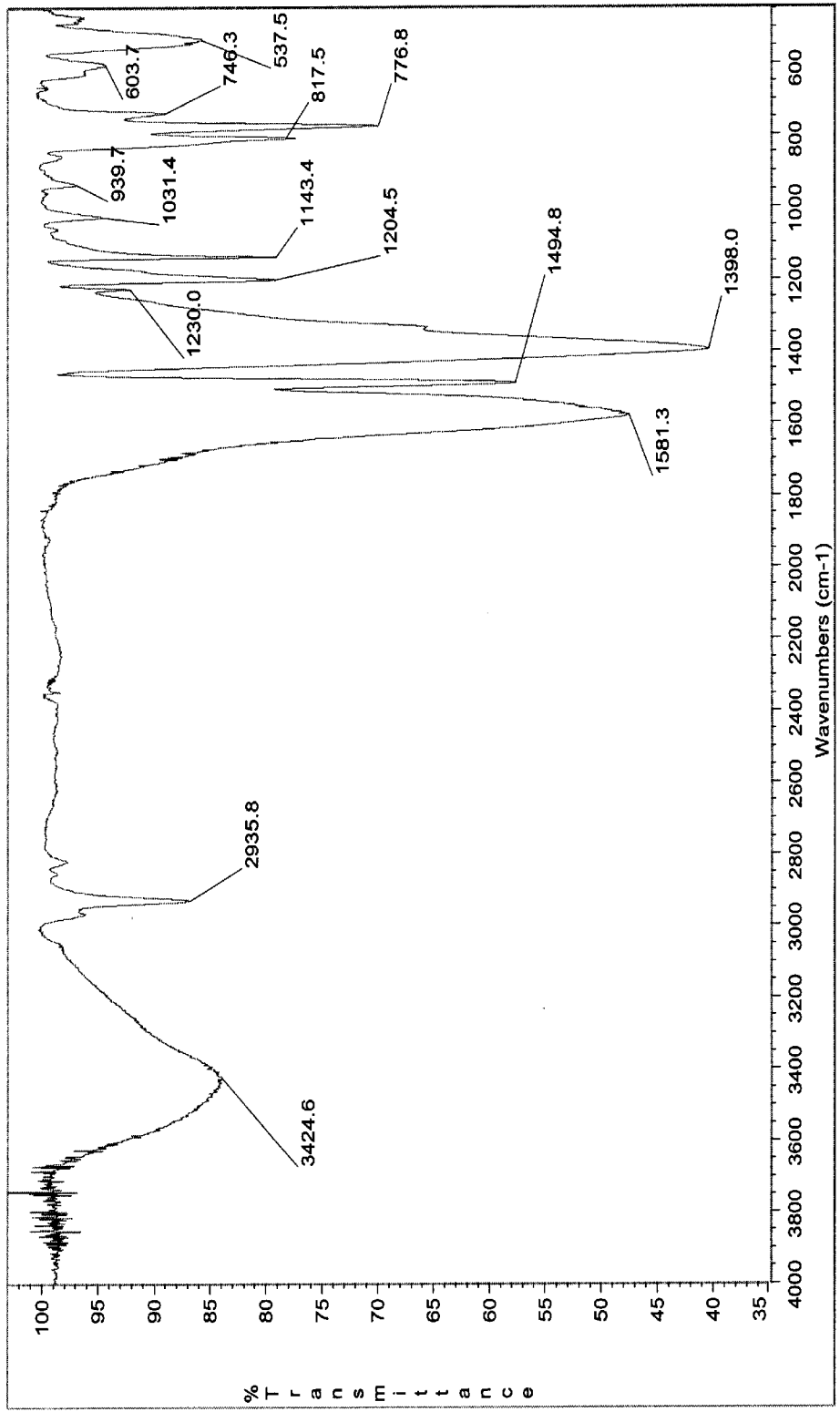
FIG. 15 is a graphic representation of an InfraRed spectrum for $Zn_4O(BDC[C_2H_4])_3.(CHCl_3)_x$.

Thermogravimetric Analysis for IRMOF-6 (FIG. 14): A crystalline sample was heated at a constant rate (5° C./min) under nitrogen flow (20 ml/min) from 30 to 700° C. As shown in FIG. 14, two weight loss steps were observed below 400° C.: the first can be attributed to the loss of DEF at the crystal surface (~1.65 DEF), and the second, occurring between 100–200° C., to the desorption of DEF guest molecules. In the last step, 400–500° C., the framework decomposes.

Preparation of IRMOF-6 with chloroform molecules as guests, $Zn_4O([C_2H_4]BDC)_3.(CHCl_3)_x$: A fresh as-synthesized sample was immersed in chloroform solution. The solution was refreshed twice with chloroform and left overnight for a complete exchange. The exchanged compound conserves its overall integrity as shown by the retention of the original in the XRPD pattern. IR, elemental analysis, and thermal gravimetric analysis confirmed the completion of the exchange as shown by the data below:

Elemental analysis for $Zn_4O([C_2H_4]BDC)_3.(CHCl_3)_x$: $C_{36.8}H_{24.8}O_{13}Cl_{6.8}Zn_4=Zn_4O([C_2H_4]BDC)_3.(CHCl)_{6.8}$ Calcd C, 26.61; H, 1.50; N, 0.00. Found C, 26.63; H, 1.55; N, 0.00.

FT-IR for $Zn_4O([C_2H_4]BDC)_3.(CHCl_3)_x$ (KBr, 3500–400 cm$^{-1}$) (FIG. 15): 3424 (br), 2936 (br), 1581 (s), 1494 (m), 1398 (vs), 1204 (w), 1143 (w), 1031(w), 940 (w), 817 (w), 777 (w), 746 (w), 537 (w). The very strong peak at 1668 cm$^{-1}$ disappeared as expected due to the full exchange of DEF with the Chloroform. $v_{C=O}$ (DEF)=1668 cm$^{-1}$.

Figure 16:
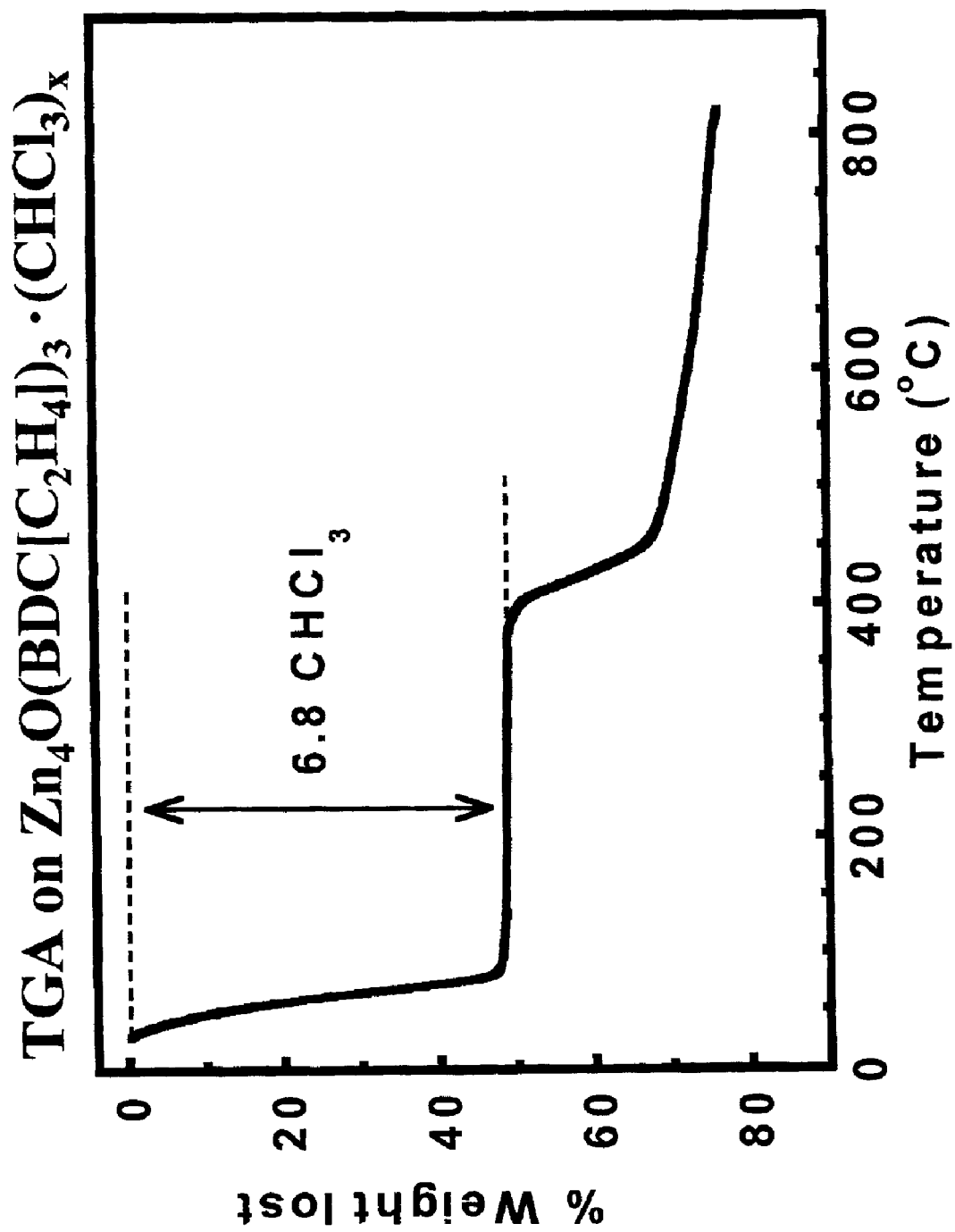
FIG. 16 is a graphic representation of a TGA on $Zn_4O(BDC[C_2H_4])_3.(CHCl_3)_x$ of the present invention.

Thermogravimetric analysis for $Zn_4O([C_2H_4]BDC)_3.(CHCl_3)_x$ (FIG. 16): The exchanged crystalline sample was heated at a constant rate (5° C./min) under nitrogen flow (20 ml/min) from 30 to 760° C. As shown in FIG. 16, a sharp weight loss was observed below 80° C., corresponding to the loss of the chloroform guest molecules (~6.8 CHCl$_3$) followed by a flat plateau synonym of framework stability up ~400° C. In the last step, 400–500° C., the framework decomposes.

Porosity studies on IRMOF-6: As observed from TGA analysis, the exchanged sample can lose all chloroform guest molecules under a flow of nitrogen at relatively low temperature (~80° C.) whereas the DEF guests require higher temperatures for removal. As a consequence, we opted to choose the exchanged framework for the sorption studies.

An exact amount of exchanged sample was introduced into a Cahn C-1000 microbalance. The compound was evacuated at room temperature and $P=10^{-5}$ torr. All the chloroform guest molecules were removed in a short time (~15 minutes), as confirmed by no additional weight change upon exposing the sample to vacuum overnight or under extended heat (~150° C.).

Figure 17:
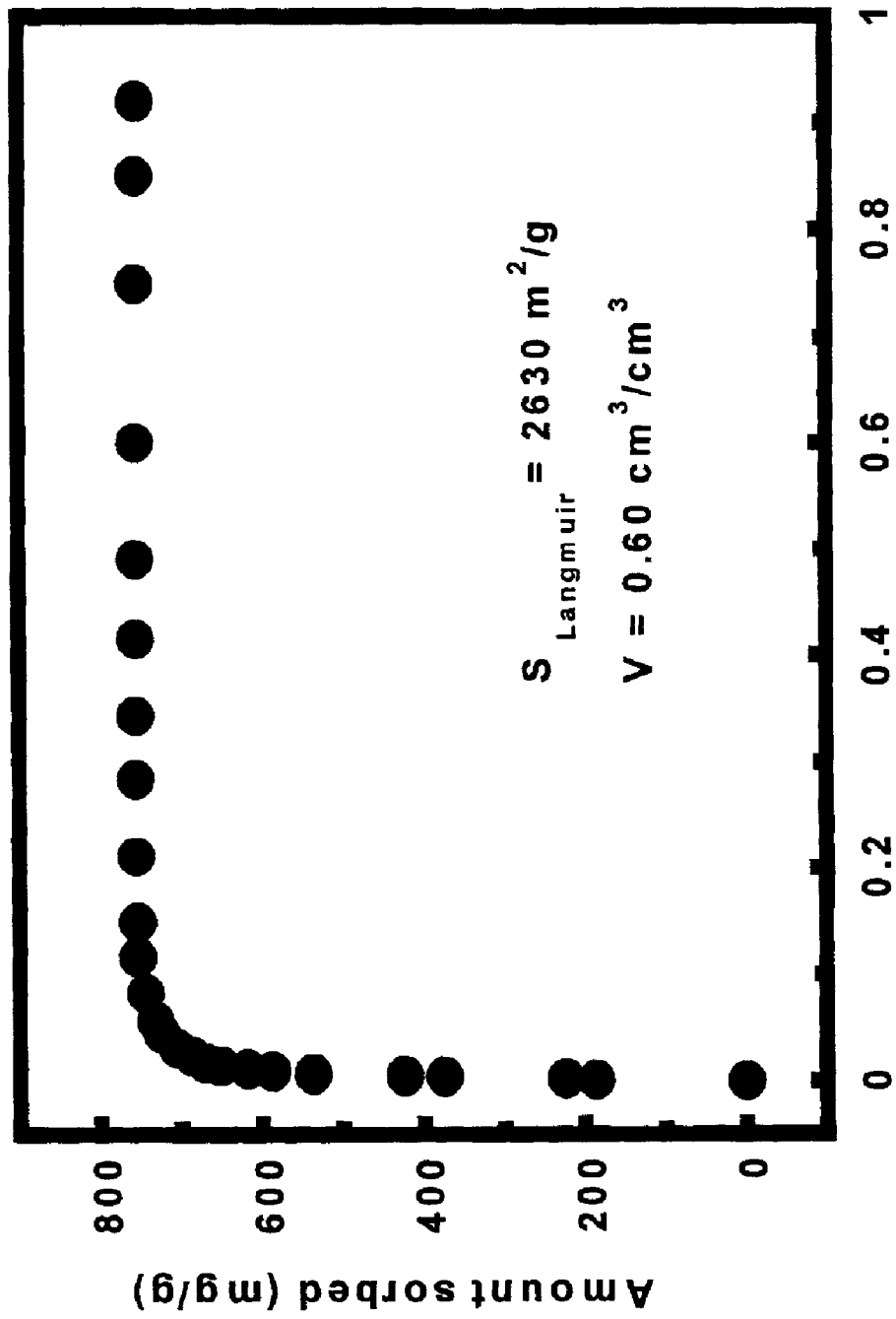
FIG. 17 is a graphic representation of sorption on $Zn_4O([H_4C_2]BDC)_3$ of the present invention.

To confirm the stability and porosity of the evacuated framework, the nitrogen sorption at 78K was monitored by introducing different increments of nitrogen gas to the sample chamber. As shown in FIG. 17, the sorption isotherm is a Type I isotherm and fully reversible, characteristic of a microporous material (<2.0 nm). The plateau was reached at relatively low pressure with no additional uptake at relatively medium pressures (near condensation pressure $P/P_0$~0.5), confirming the homogeneity of the pores, and the absence of mesopores and macropores.

By applying the Langmuir and DR equations, the Langmuir surface and pore volume, respectively, were estimated to be $S_{langmuir}$=2630 m$^2$/g and Vp=0.60 cm$^3$/cm$^3$.

The evacuated sample was also exposed to different organic vapors (CH$_2$Cl$_2$, C$_6$H$_6$, CCl$_4$ and C$_6$H$_{12}$) and all the isotherms were Type I and reversible. The data are summarized in Table 2, and they show that the pore volume converge to the same values (0.57–0.60 cm$^3$/cm$^3$), proving the homogeneity of the pores.

The resultant IRMOF-6 cubic crystals were collected and fully characterized. The crystallographic parameters and a representative picture of the framework are summarized in FIG. 11. The elemental analysis confirms the composition as shown above, the Infrared confirms that the carboxylates are fully deprotonated. The overlap of the observed and simulated XRPD confirms the purity of the sample. Diethylformamide molecules occupied the void spaces in the porous structure of IRMOF-6. The DEF guest molecules can be removed from the pores under extended vacuum or by heating the sample as shown in FIG. 14. The DEF guest molecules can also be fully exchanged with a volatile, molecule such as chloroform as proven by the data above. To confirm that IRMOF-6 maintains its structure and mainly its porosity upon removing the guest molecules sorption studies were carried out on the fully evacuated IRMOF-6. As shown in FIG. 17, the isotherm is a type I isotherm characteristic of a microporous material. The data summarized in table 2 prove that IRMOF-6 has homogeneous porous and able to sorb different guests molecules.

Figure 19A:
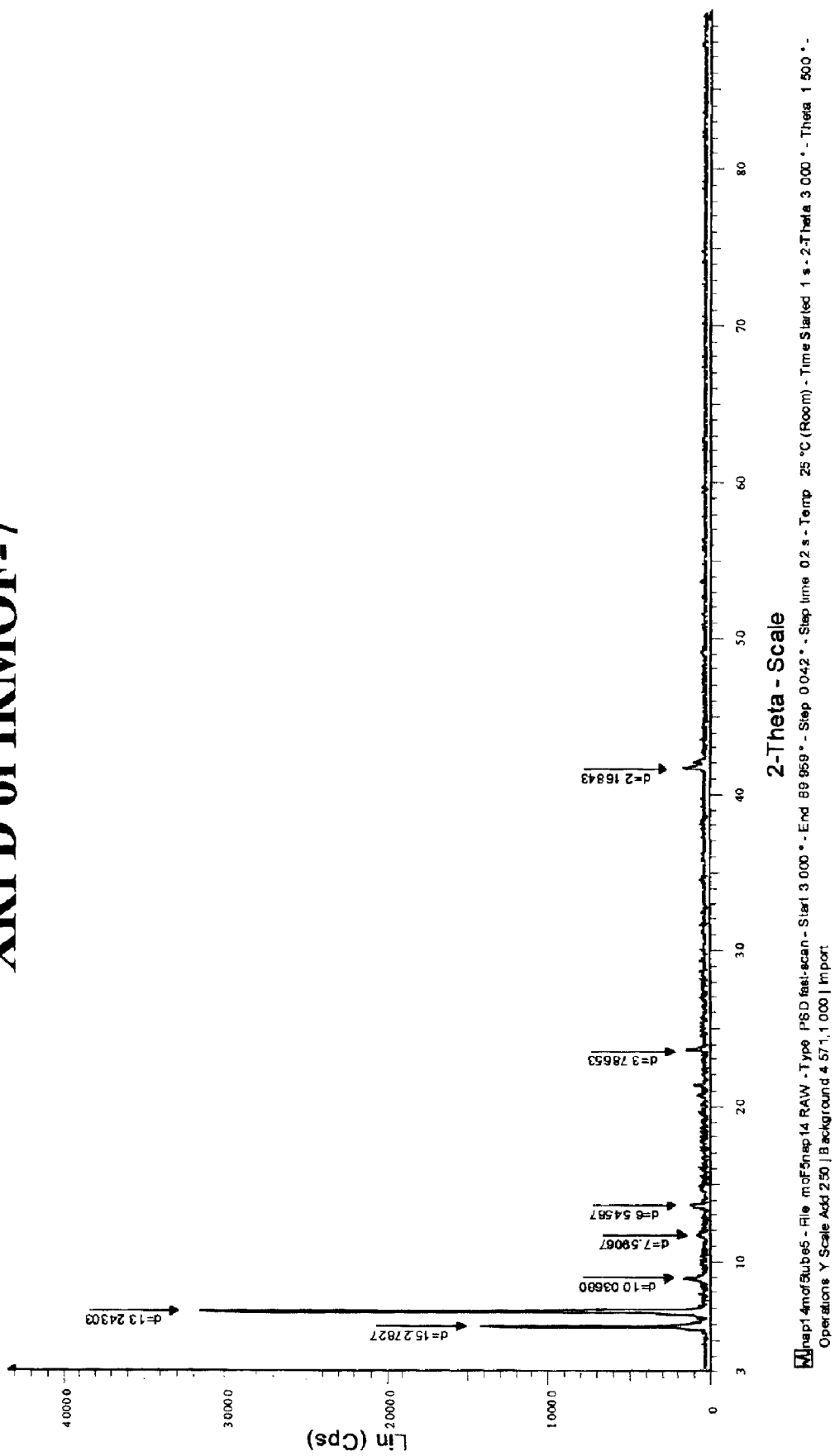
FIG. 19a is a graphic representation of XRPD of IRMOF-7.
Figure 19B:
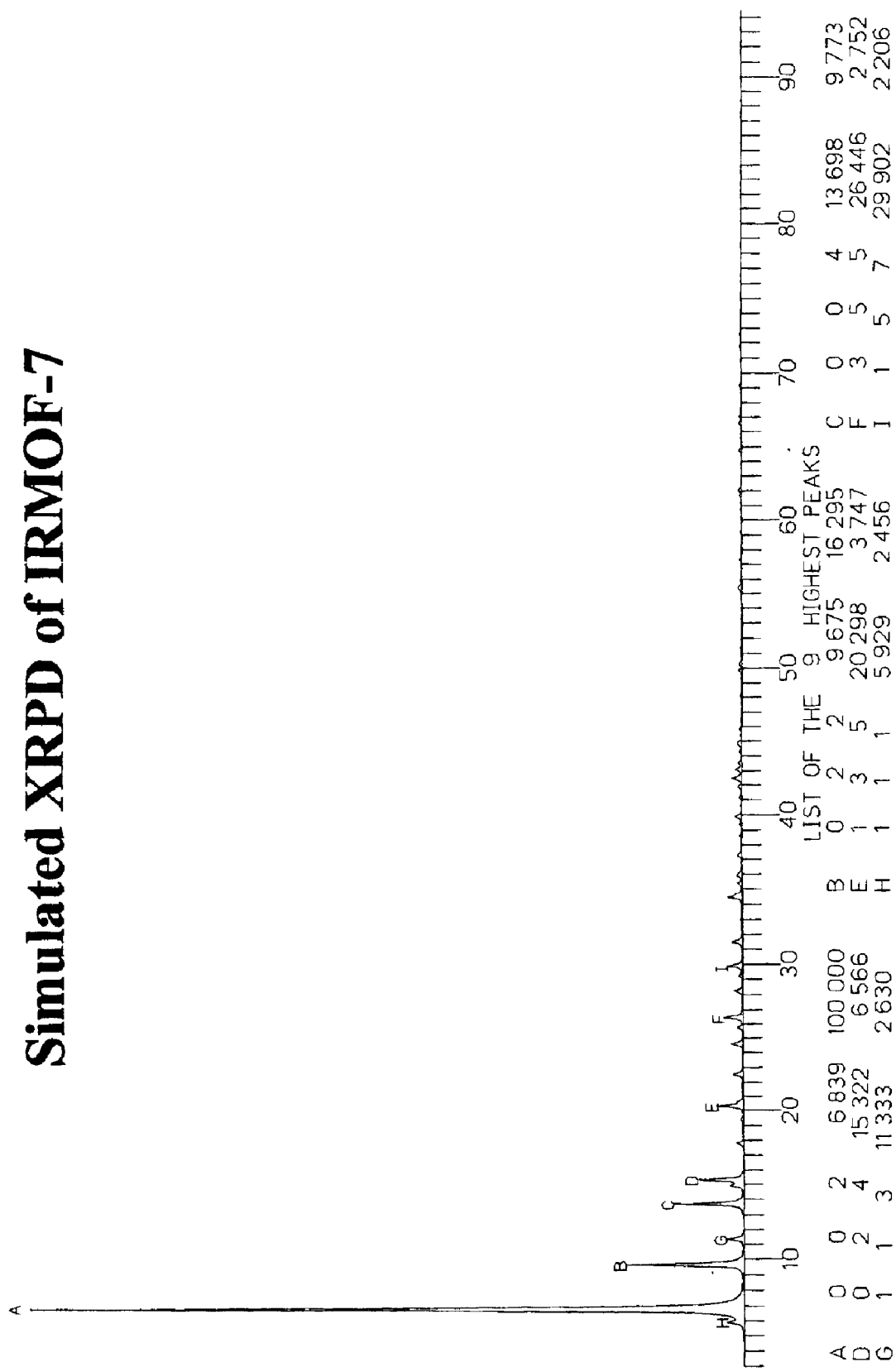
FIG. 19b is a graphic representation of a simulated XRPD of IRMOF-7 of the present invention.

Preparation of IRMOF-7:

$Zn_4O(2,4NDC)_3 \cdot (DEF)_x$ (IRMOF-7): An exact amount of 2,4 naphthalene dicarboxylic acid, (2,4 H2NDC) (0.015 g, 0.072 mmol), and zinc nitrate tetrahydrate, $Zn(NO_3)_2 \cdot 4H_2O$, (0.0.53 g, 0.20 mmol), were dissolved in 5 mL diethylformamide, DEF, and placed in a Parr Teflon-lined stainless steel vessel (23 mL). The vessel was sealed and heated at a constant rate (2° C./min) to 85° C. for 20 h and then cooled to room temperature at a rate of 1° C./min. The resultant sample was filtered and washed with DEF (3×5 mL) yielding IRMOF-7. IRMOF-7 is insoluble in water and all common organic solvents such as ethanol, acetonitrile, tetrahydrofuran, chloroform, dichloromethane, acetone, N,N'-dimethylformamide, and N,N'-diethylformamide. The observed X-ray powder diffraction pattern shown in FIG. 19a was compared to the simulated one in FIG. 19b to confirm the purity of the as-synthesized IRMOF-7, $Zn_4O(2,4NDC)_3 \cdot (DEF)_x$.

The resultant IRMOF-7 cubic crystals were collected. The crystallographic parameters and a representative picture are summarized in FIG. 18.

Elemental analysis: $C_{71}H_{101}O_{23}N_7Zn_4 = Zn_4O(1,4NDC)_3 \cdot (DEF)_7(H_2O)_3$ Calcd C, 50.69; H, 6.05; N, 5.83. Found C, 50.81; H, 6.28; N, 5.85.

FT-IR (KBr, 3500–400 $cm^{-1}$): 3435 (br), 2980 (w), 2935 (w), 2340 (w), 1644 (s), 1605 (vs), 1519 (m), 1466 (m), 1413 (s), 1361 (vs), 1263 (m), 1220 (w), 1163 (w), 1108 (w), 840 (w), 792 (w), 562 (w).

Preparation of IRMOF-8:

Exact amounts of 2,6-naphthalene dicarboxylic acid, (2,6 H2NDC) (0.012 g, 0.055 mmol), and zinc nitrate tetrahydrate, $Zn(NO_3)_2 \cdot 4H_2O$, (0.110 g, 0.42 mmol), were dissolved in 10 ml DEF and left at room temperature. After 2 days, cubic-like crystals were grown. The resultant sample (83%) was filtered and washed with DEF (3×5 mL), yielding IRMOF-8. Heating the same amounts of starting materials to 95° C. for 20 hours leads to the same compound. However the crystals made at room temperature have cleaner surfaces and were used for single X-ray data collection.

Figure 20:
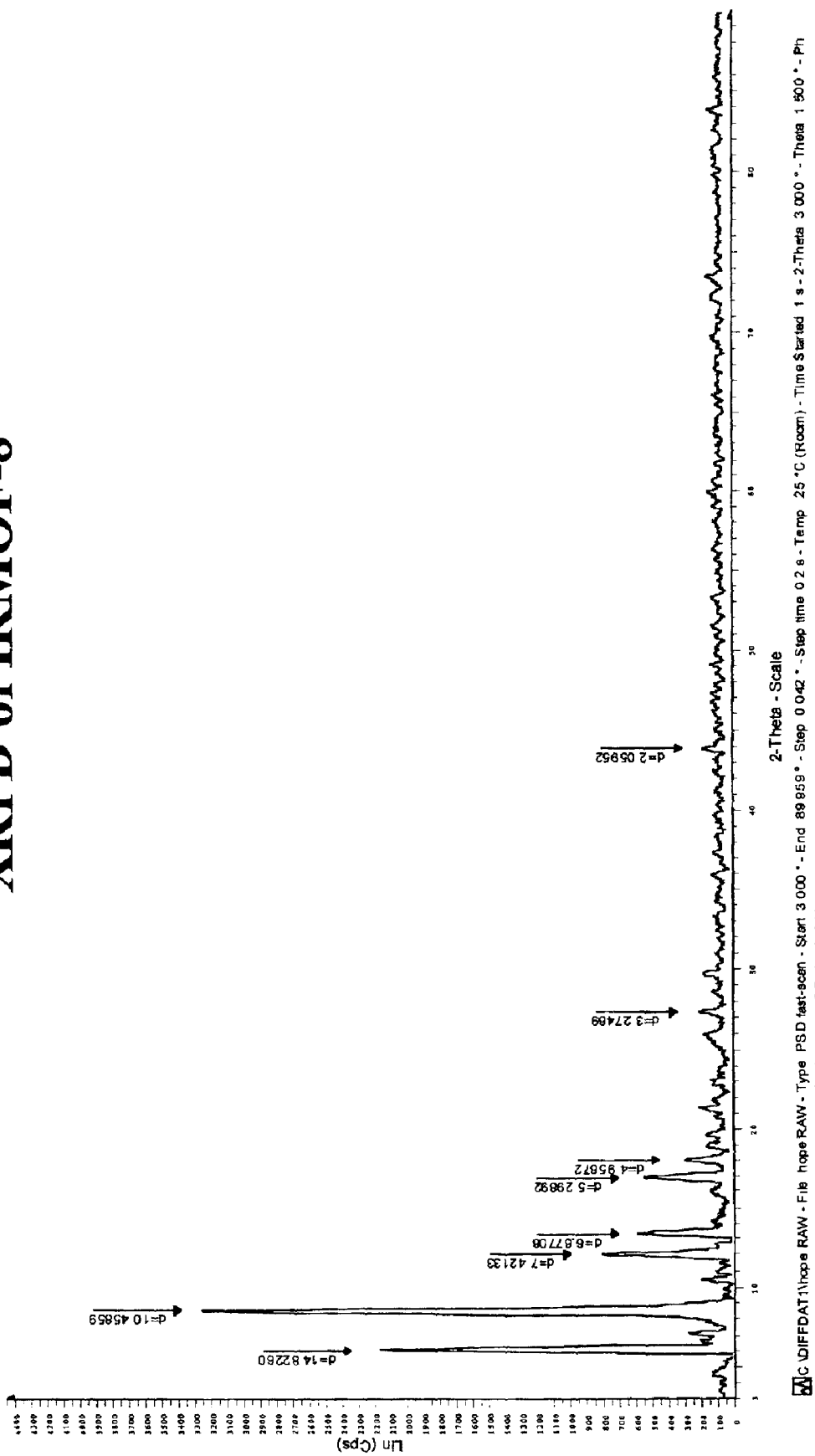
FIG. 20 is a graphic representation of XRPD of IRMOF-8 of the present invention.

IRMOF-8 is insoluble in water and all common organic solvents such as ethanol, acetonitrile, tetrahydrofuran, chloroform, dichloromethane, acetone, N,N'-dimethylformamide, and N,N'-diethylformamide. The observed X-ray powder diffraction pattern is shown in FIG. 20.

Elemental analysis: $C_{66}H_{84}O_{19}N_6Zn_4 = Zn_4O(NDC)_3 \cdot (DEF)_6$ Calcd C, 51.91; H, 5.54; N, 5.50. Found C, 51.90; H, 5.96; N, 5.57.

FT-IR (KBr, 3500–400 $cm^{-1}$): 3455 (br), 2982 (m), 2941 (w), 2874 (w), 1667 (s), 1642(m), 1622 (s), 1413 (vs), 1494 (w), 1363 (m), 1266 (m), 1200 (w), 1108 (w), 930 (w), 992 (m), 487 (w).

Preparation of IRMOF-9:

Method 1: Exact amounts of 4,4'biphenyldicarboxylic acid, (4,4'-BPDCH_2) (0.08 g, 0.05 mmol), and zinc nitrate tetrahydrate, $Zn(NO_3)_2 \cdot 4H_2O$, (0.110 g, 0.42 mmol), were dissolved in 9 ml DEF and and placed in a Parr Teflon-lined stainless steel vessel (23 mL). The vessel was sealed and heated at a constant rate (2° C./min) to 85° C. for 20 h and then cooled to room temperature at a rate of 1° C./min. The resultant sample (63%) was filtered and washed with DEF (3×5 mL) yielding IRMOF-9.

Elemental analysis: $C_{73}H_{103}O_{26}N_9Zn_4 = Zn_4O(BPDC)_3 \cdot (DEF)_2(DMF)_7(H_2O)_4$ Calcd C, 49.14; H, 5.82; N, 7.07. Found C, 49.52; H, 6.50; N, 7.22.

FT-IR (KBr, 4000–400 $cm^{-1}$): 3430 (br), 2981 (w), 2935 (w), 2870 (w), 1663 (vs), 1607 (vs), 1545 (m), 1403 (vs), 1347 (s), 1311 (w), 1265 (w), 1220 (w), 1184 (w), 1113 (w), 1011 (w), 777 (m), 705 (w), 680 (w), 644 (w), 456 (w).

Figure 22A:
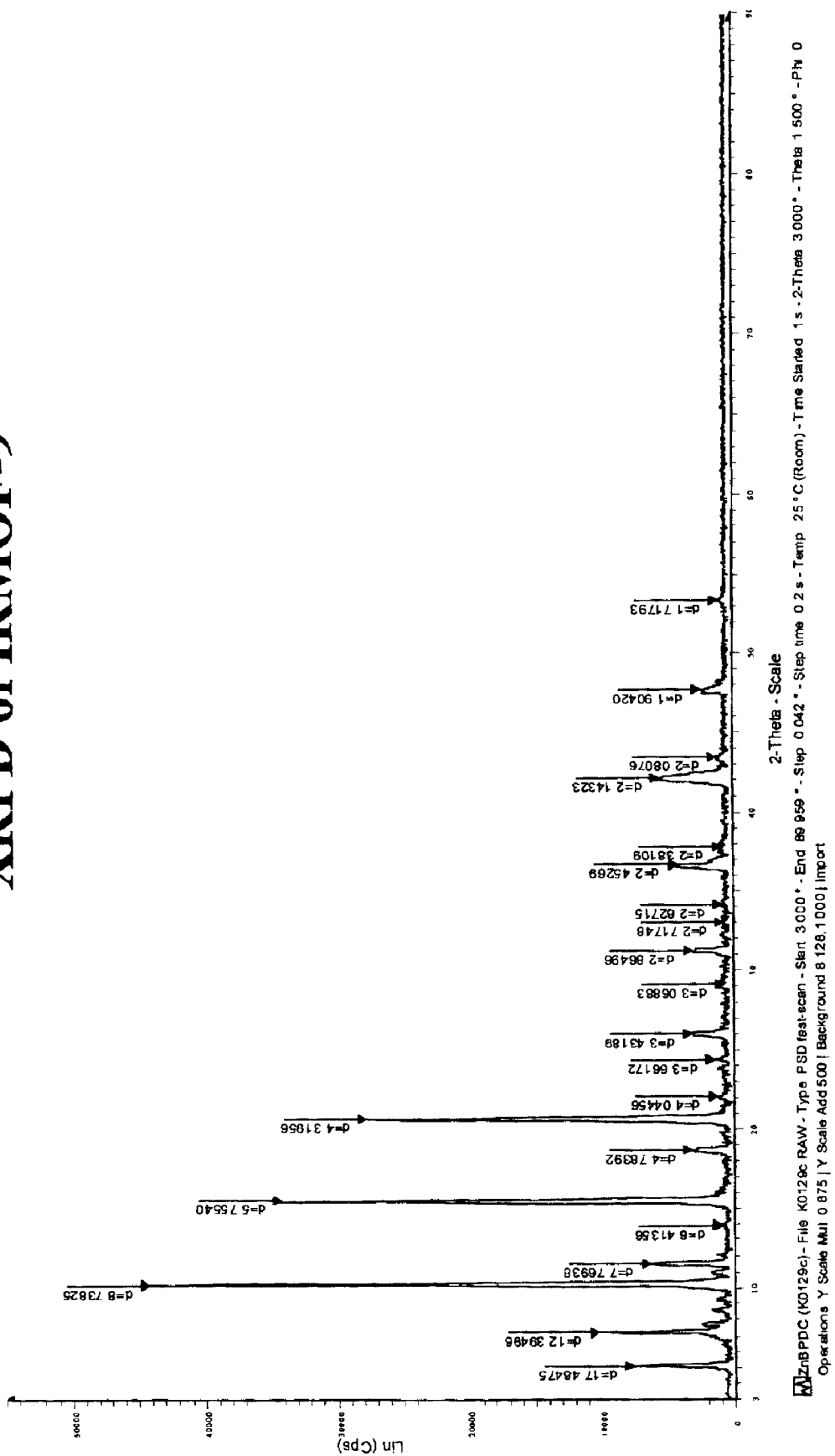
FIG. 22a is a graphic representation of XRPD of IRMOF-9 of the present invention.
Figure 22B:
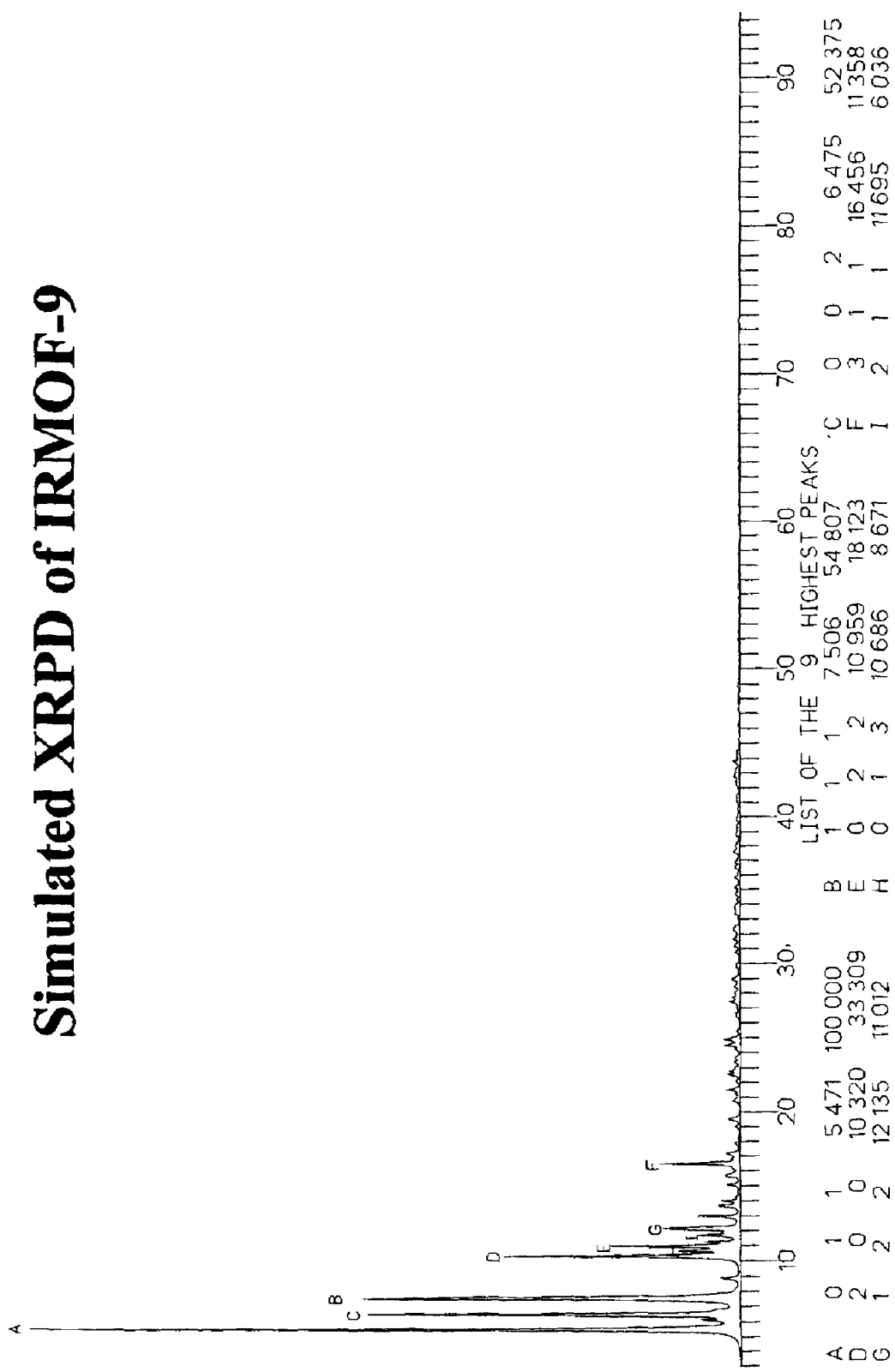
FIG. 22b is a graphic representation of simulated XRPD of IRMOF-9.

Method 2: $Zn_4O(BPDC)_3 \cdot (DMF)_x$(IRMOF-9): A mixture of N,N' dimethylformamide and benzene DMF/2-$C_3H_8$OH: 4/4 ml containing 4,4' biphenyl dicarboxylic acid, $H_2$BPDC, (0.015 g, 0.062 mmol) and zinc nitrate tetrahydrate, $Zn(NO_3)_2 \cdot 4H_2O$, (0.130 g, 0.50 mmol) was placed in a Parr Teflon-lined stainless vessel (23 mL). The vessel was sealed and heated to 85° C. for 24 h at a rate of 2.0° C./min and cooled to room temperature at a rate of 2.0° C./min. The resultant product was filtered, washed with a DMF/benzene mixture (3×5 mL) to give 60% of IRMOF-9. The as-synthesized IRMOF-9 is insoluble in water and all common organic solvents such as ethanol, acetonitrile, tetrahydrofuran, chloroform, dichloromethane, acetone, N,N'-dimethylformamide, and N,N'-diethylformamide. The observed X-ray powder diffraction pattern is shown in FIG. 22a, and the simulated pattern from the single X-Ray data is shown in FIG. 22b.

Figure 23:
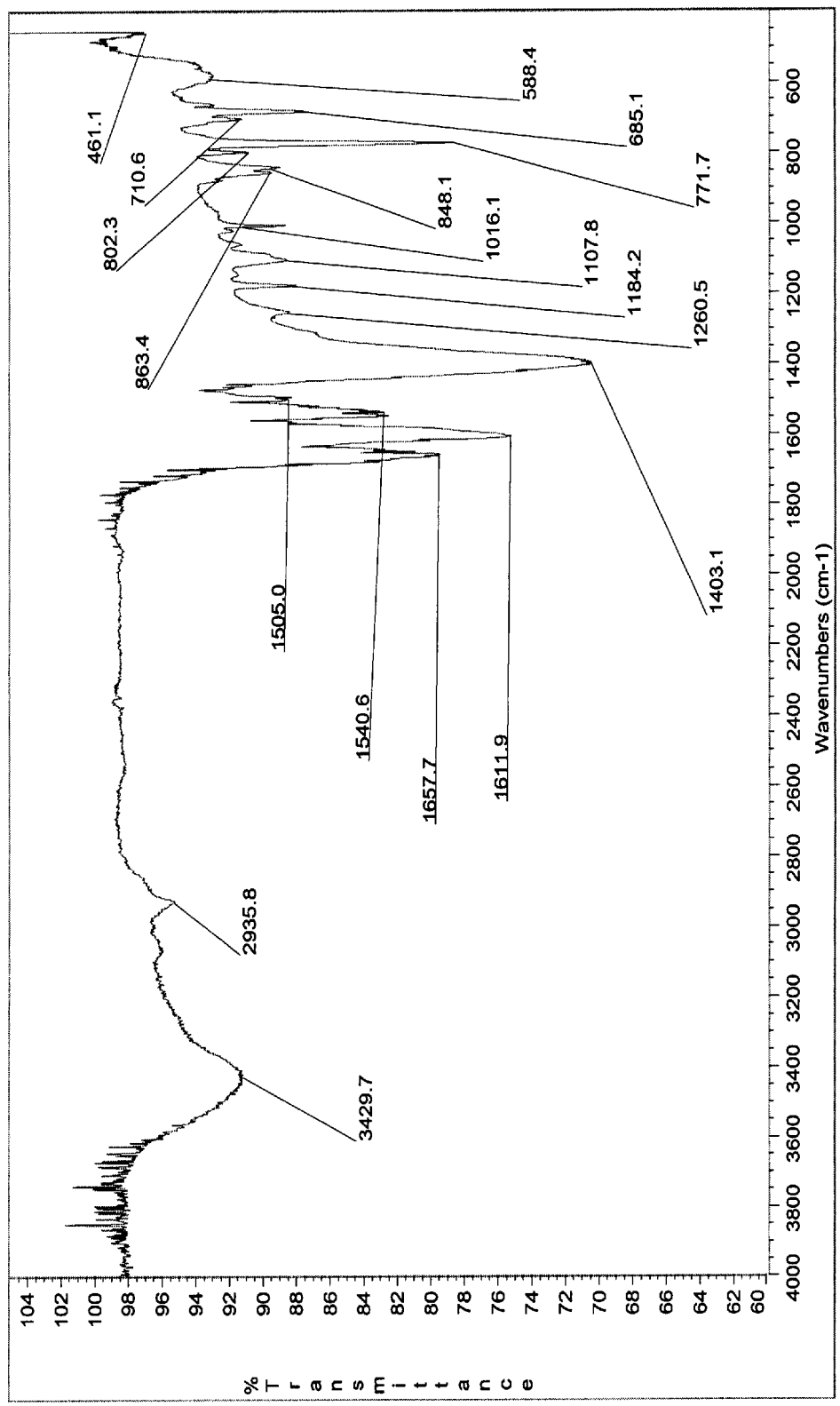
FIG. 23 is a graphic representation of an InfraRed spectrum for IRMOF-9 of the present invention.

The InfraRed spectrum for IRMOF-9 is shown in FIG. 23. FT-IR for IRMOF-9: FT-IR (KBr, 4000–400 cm-1): 3430 (br), 2936 (w), 1658 (m), 1612 (s), 1541 (w), 1505 (w), 1403 (vs), 1261 (w), 1184 (w), 1108 (w), 1016 (w), 863 (w), 848 (w), 802 (w), 772 (m), 711 (w), 685 (w), 588 (br), 461 (w).

Figure 21:
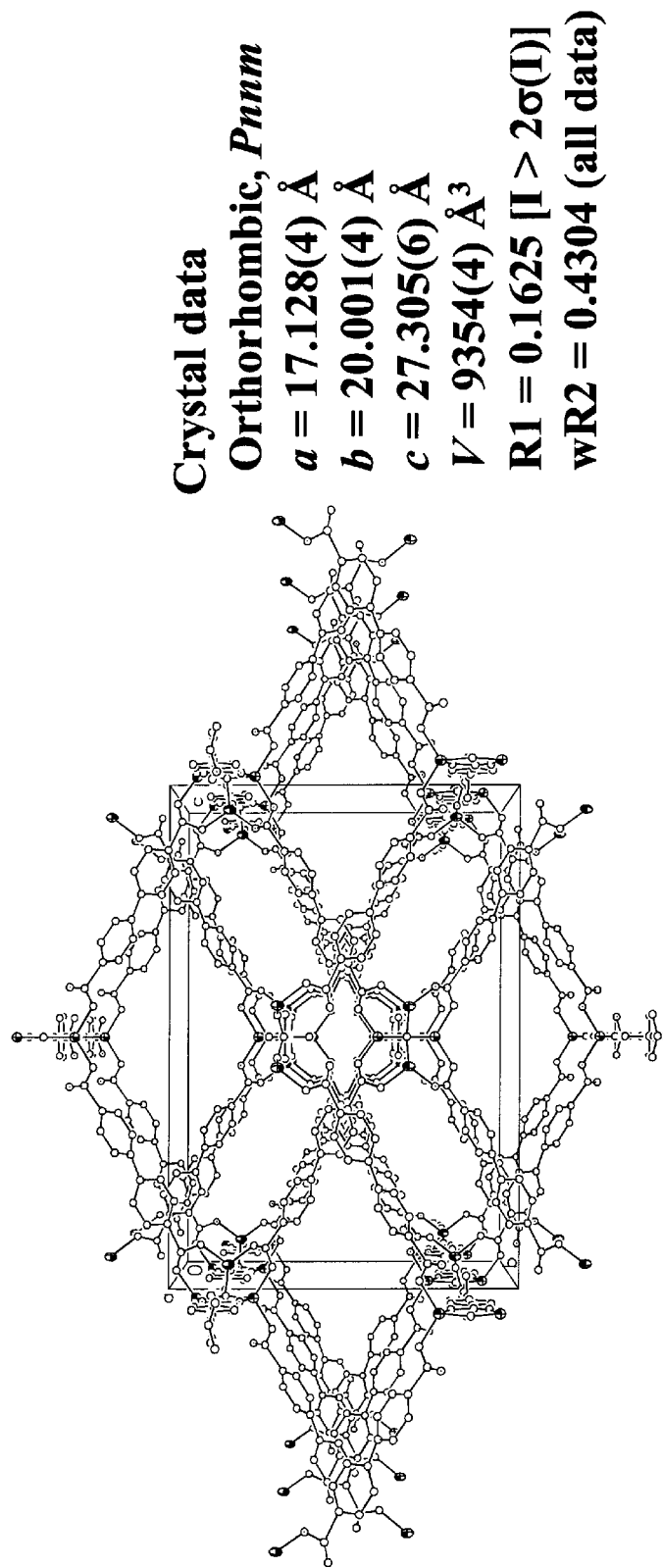
FIG. 21 is a diagrammatic representation of a crystal structure for IRMOF-9 of the present invention.

The resultant IRMOF-9 cubic crystals were collected and characterized. The crystallographic parameters and a representative picture of the framework are summarized in FIG. 21.

Preparation of IRMOF-10:

Exact amounts of 4,4'biphenyldicarboxylic acid, (4,4'-BPDCH_2) (0.005 g, 0.02 mmol), and zinc nitrate tetrahydrate, $Zn(NO_3)_2 \cdot 4H_2O$, (0.031 g, 0.12 mmol), were dissolved in 16 ml DEF and placed in a Parr Teflon-lined stainless steel vessel (23 mL). The vessel was sealed and heated at a constant rate (2° C./min) to 85° C. for 20 h and then cooled to room temperature at a rate of 1° C./min. The resultant sample (52%) was filtered and washed with DEF (3×5 mL) yielding IRMOF-10.

Elemental analysis: $C_{102}H_{158}O_{26}N_{12}Zn_4 = Zn_4O(BPDC)_3 \cdot (H_2O)(DEF)_{12}$ Calcd C, 54.94; H, 7.14; N, 7.54. Found C, 54.40; H, 7.32; N, 7.54.

FT-IR (KBr, 3500–400 $cm^{-1}$): 3455 (br), 2981 (m), 2941 (w), 2880 (w), 1668 (vs), 1607 (vs), 1546 (m), 1398 (s), 1311 (w), 1265 (m), 1220 (m), 1118 (w), 1011 (w), 950 (w), 827 (w), 777 (m), 690 (w), 556 (w).

Preparation of IRMOF-11:

Method 1: Exact amounts of tetrahydropyrene-2,7-dicarboxylic acid, (4,4'-HPDCH_2) (0.015 g, 0.05 mmol), and zinc nitrate tetrahydrate, $Zn(NO_3)_2 \cdot 4H_2O$, (0.052 g, 0.20 mmol), were dissolved in 10 ml DEF and placed in a Parr Teflon-lined stainless steel vessel (23 mL). The vessel was sealed and heated at a constant rate (2° C./min) to 105° C. for 20 h and then cooled to room temperature at a rate of 1° C./min. The resultant sample (76%) was filtered and washed with DEF (3×5 mL) yielding IRMOF-11.

Elemental analysis: $C_{114}H_{172}N_{12}O_{27}Zn_4=Zn_4O(HPDC)_3.(DEF)_{12}(H_2O)_2$ Calcd C, 56.95; H, 7.21; N, 6.99. Found C, 56.66; H, 10 7.02; N, 7.02.

FT-IR (KBr, 4000–400 cm$^{-1}$): 3430 (br), 2977 (w), 2941 (w), 2890 (w), 2840 (w), 1647 (vs), 1601 (s), 1548 (m), 1464 (m), 1398 (vs), 1352 (s), 1301 (w), 1270 (w), 1245 (w), 1214 (w), 1113 (w), 1091 (w), 1006 (w), 827 (w), 650 (w).

Figure 28A:
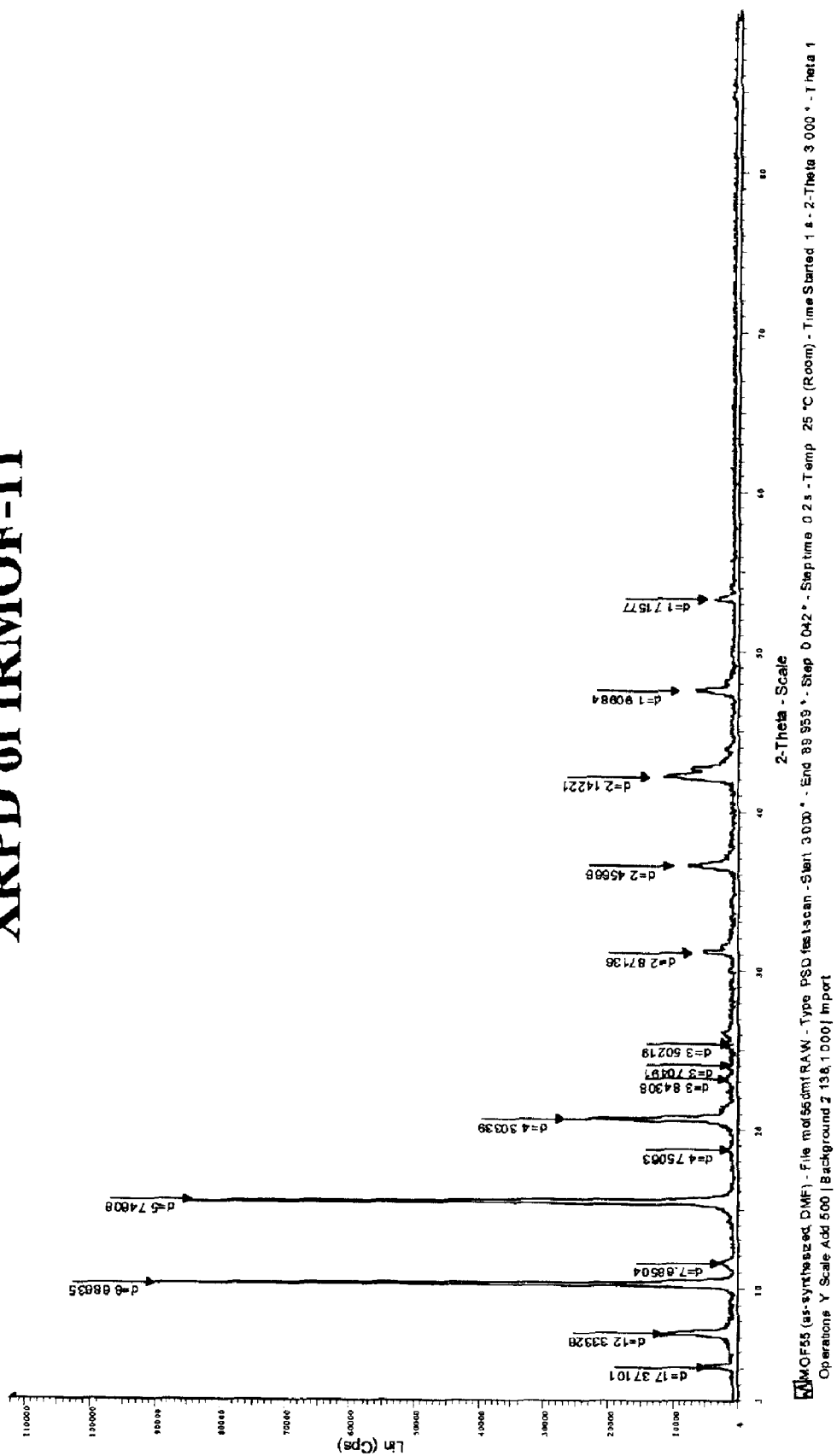
FIG. 28a is a graphic representation of XRPD of IRMOF-11 of the present invention.
Figure 28B:
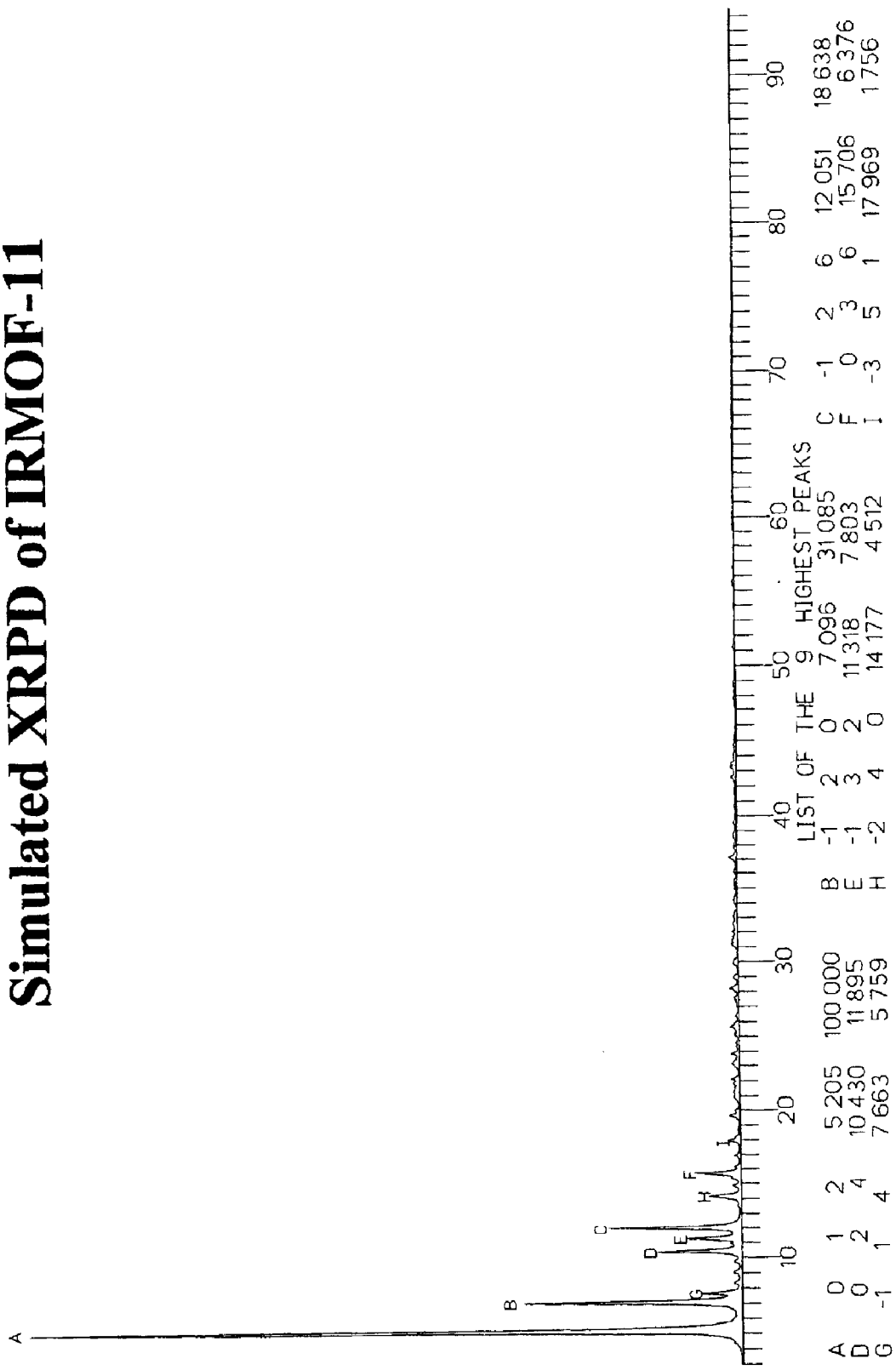
FIG. 28b is a graphic representation of a simulated XRPD of IRMOF-11 of the present invention.

Method 2: $Zn_4O(TPDC)_3.4H_2O.9DMF$ (IRMOF-11): A mixture of dimethylformamide and isopropanol DMF/2-$C_3H_8OH$: 6/2 ml containing tetrahydropyrene-2,7-dicarboxylic acid, $H_2TPDC$ (0.015 g, 0.051 mmol), and zinc nitrate tetrahydrate, $Zn(NO_3)_2.4H_2O$ (0.080 g, 0.31 mmol), was placed in a Parr Teflon-lined stainless vessel (23 mL). The vessel was sealed and heated to 85° C. for 24 h at a rate of 2.0° C./min and cooled to room temperature at a rate of 2.0° C./min. The resultant product, rectangular, pale yellow crystals, was filtered, washed with a DMF and isopropanol mixture (3×5 mL) to yield 69% of IRMOF-11. The as-synthesized IRMOF-11 is insoluble in water and all common organic solvents such as ethanol, acetonitrile, tetrahydrofuran, chloroform, dichloromethane, acetone, N,N'-dimethylformamide, and N,N'-diethylformamide. Phase purity of the bulk products was confirmed by comparison of the observed X-ray powder diffraction pattern shown in FIG. 28a, and the calculated X-ray powder diffraction pattern shown in FIG. 28b simulated from the single-crystal structure data of IRMOF-11.

Elemental analysis for IRMOF-11: $C_{81}H_{107}N_9O_{26}Zn_4=Zn_4O(TPDC)_3.(4H_2O).(9DMF)$ Calcd C, 51.63; H, 5.72; N, 6.69. Found C, 51.95; H, 5.53; N, 6.76.

Figure 29:
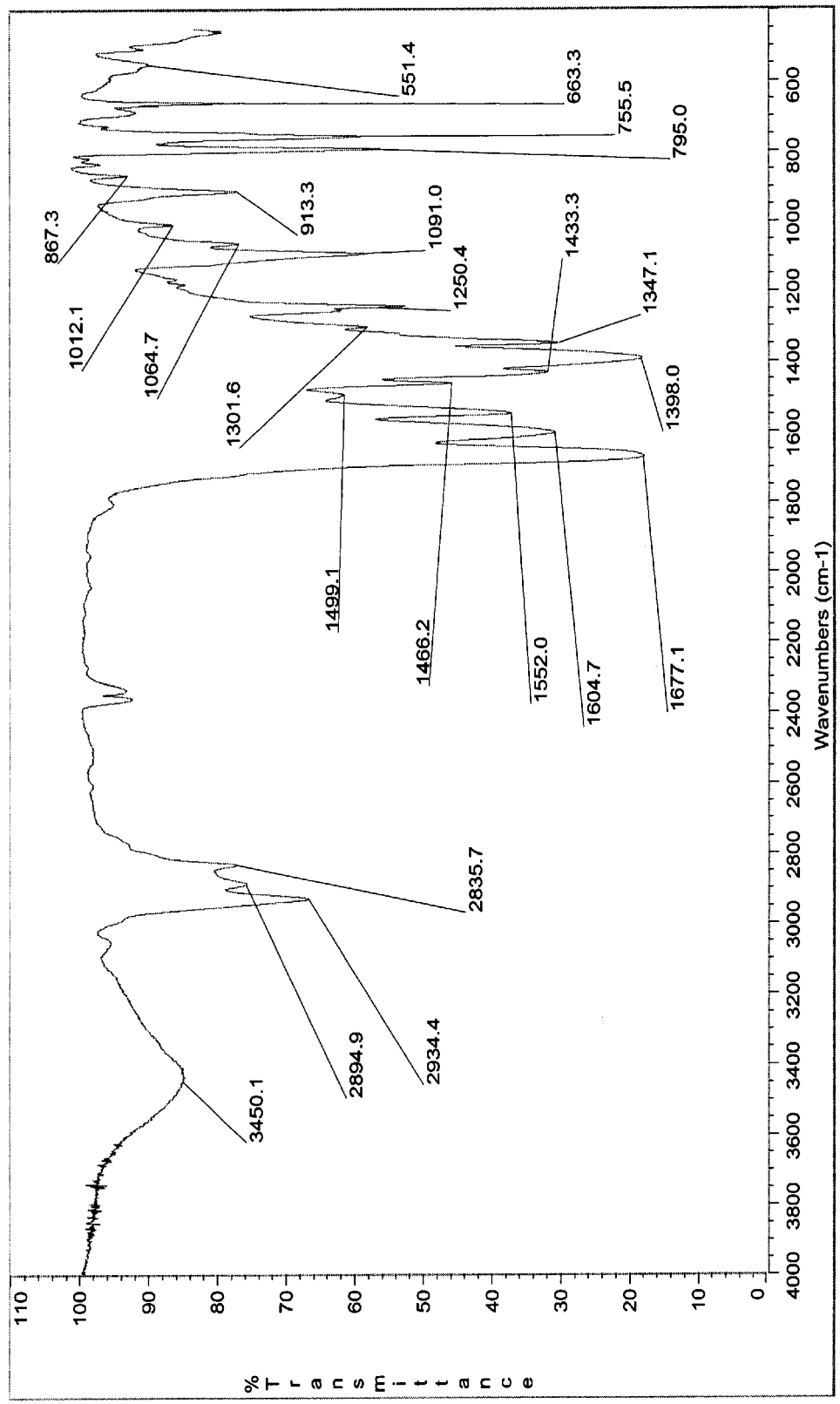
FIG. 29 is a graphic representation of an InfraRed spectrum for IRMOF-11 of the present invention.

Infra-Red spectra for IRMOF-11 (FIG. 29):

FT-IR for IRMOF-11 (KBr, 4000–400 cm$^{-1}$): 3450 (br), 2934 (w), 2895 (w), 2836 (w), 1677 (vs), 1605 (s), 1552 (m), 1499 (w), 1466 (w), 1433 (s), 1398 (vs), 1347 (s), 1302 (w), 1250 (w), 1091 (w), 1065 (w), 1012 (w), 913 (w), 867 (w), 795 (w), 756 (w), 663 (w), 551 (w)

Thermogravimetric analysis for IRMOF-11: A crystalline sample (16.527 mg) was heated from 30° C. to 900° C. at 5.0° C./min; two separate weight-loss steps were observed. The first weight loss (38.1%) step at 250° C. corresponds to the removal of (4H$_2$O+9DMF) and the second, which occurs above 400° C. (41.8%), corresponds to framework decomposition. A plateau between 250–400° C. was observed, confirming the stability of the evacuated framework IRMOF-11 up to 400° C.

Figure 27:
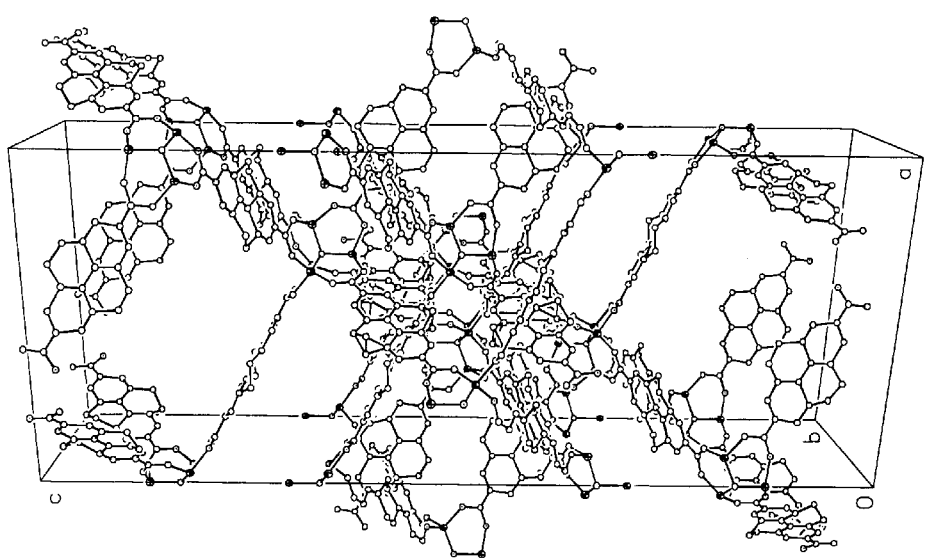
FIG. 27 is a diagrammatic representation of a crystal structure for IRMOF-11 of the present invention.

The resultant IRMOF-11 cubic crystals were collected and fully characterized. The crystallographic parameters and a representative picture of the framework are summarized in FIG. 27. The elemental analysis confirms the composition as shown above, the Infrared confirms that the carboxylates are fully deprotonated. The overlap of the observed and simulated XRPD confirms the purity of the sample.

Preparation of IRMOF-12:

Method 1: Exact amounts of tetrahydropyrene-2,7-dicarboxylic acid, (4,4'-HPDCH$_2$) (0.005 g, 0.017 mmol), and zinc nitrate tetrahydrate, $Zn(NO_3)_2.4H_2O$, (0.031 g, 0.12 mmol), were dissolved in 16 mL DEF and placed in a Parr Teflon-lined stainless steel vessel (23 mL). The vessel was sealed and heated at a constant rate (2° C./min) to 85° C. for 20 h and then cooled to room temperature at a rate of 1° C./min. The resultant sample (65%) was filtered and washed with DEF (3×5 mL) yielding IRMOF-12.

Elemental analysis: $C_{104}H_{148}O_{24}N_{10}Zn_4=Zn_4O(HPDC)_3.(H_2O)(DEF)_{10}$ Calcd C, 57.20; H, 6.83; N, 6.41. Found C, 57.16; H, 7.25; N, 6.53.

FT-IR (KBr, 3500–400 cm$^{-1}$): 3455 (br), 2982 (m), 2941 (m), 2879 (w), 1668 (vs), 1602 (s), 1551 (m), 1464 (m), 1434 (m), 1393 (vs), 1352 (m), 1306 (w), 1266 (w), 1220 (w), 1113 (w), 920 (w), 827 (w), 797 (m), 761 (m), 650(w).

Figure 25A:
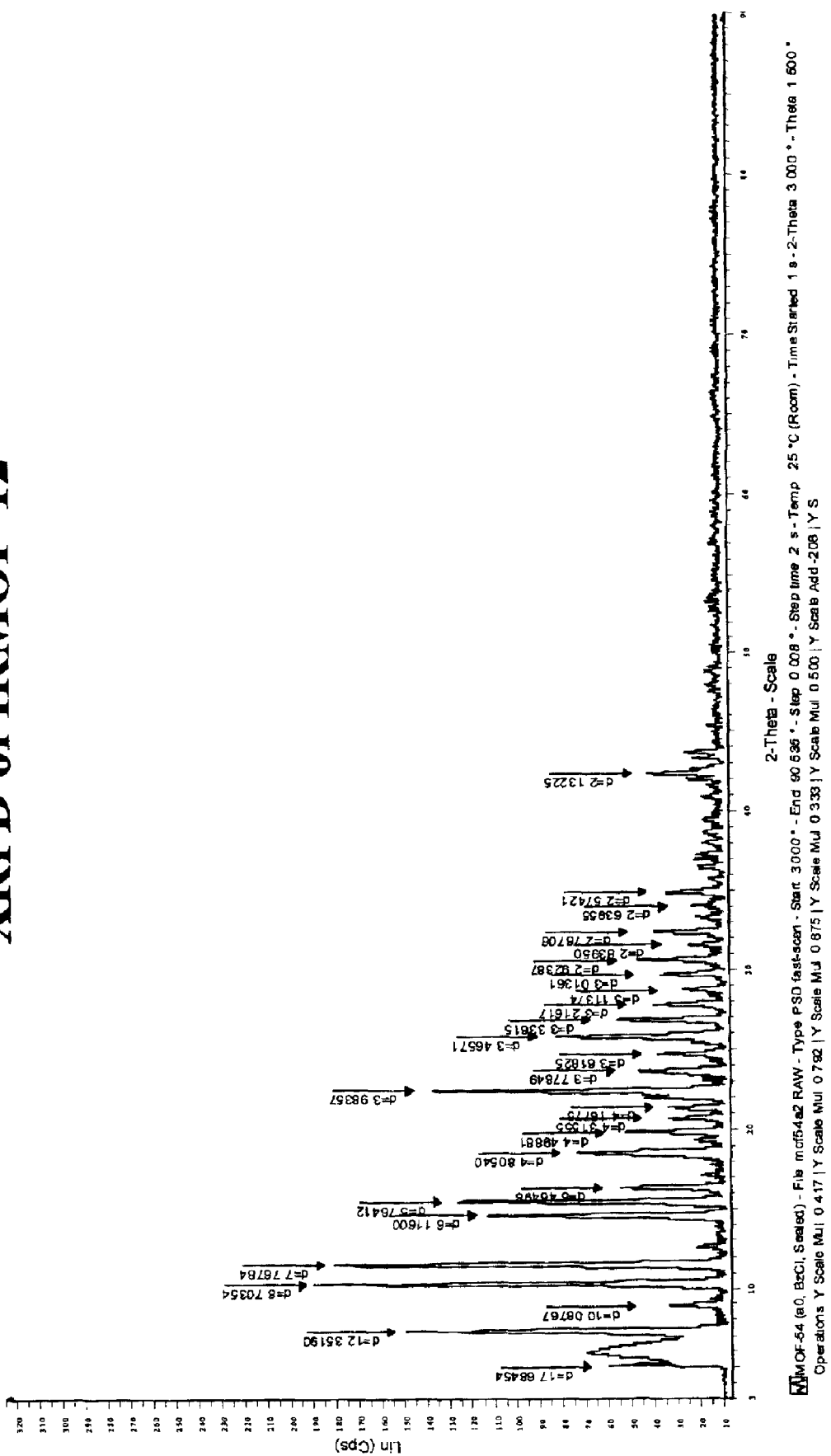
FIG. 25a is a graphic representation of XRPD of IRMOF-12 of the present invention.
Figure 25B:
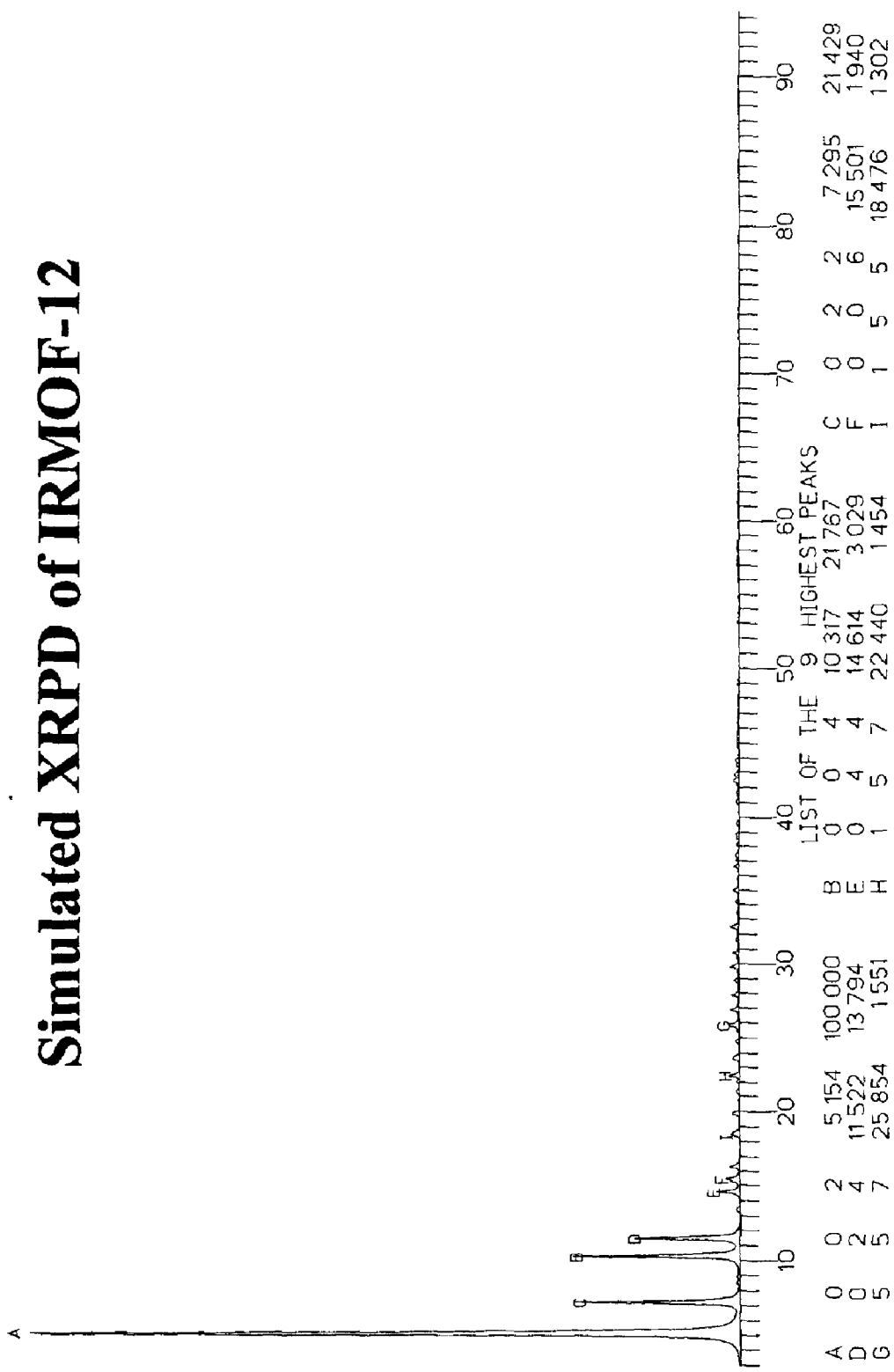
FIG. 25b is a graphic representation of simulated XRPD of IRMOF-12 of the present invention.

Method 2: $Zn_4O(TPDC)_3.11H_2O.CHP.$chlorobenzene (IRMOF-12) Exact amounts of tetrahydropyrene-2,7-dicarboxylic acid, $H_2PDC$, (0.040 g, 0.048 mmol), and zinc nitrate tetrahydrate, $Zn(NO_3)_2.4H_2O$, (0.040 g, 0.15 mmol), were dissolved in 1-cyclohexyl-2-pyrrolidinone, CHP, (7.0 mL) and chlorobenzene (3.0 mL). The mixture was exposed to diluted triethylamine solution. The diluted triethylamine solution was prepared by diluting 0.10 mL of the stock solution (triethylamine: chlorobenzene=1:10, v/v) with 5.0 mL of chlorobenzene. After three weeks cubic, colorless crystals were produced. The resultant product was filtered, washed with a DMF and chlorobenzene mixture (3×5 mL) to yield 7% of IRMOF-12. The as-synthesized IRMOF-12 is insoluble in water and all common organic solvents such as ethanol, acetonitrile, tetrahydrofuran, chloroform, dichloromethane, acetone, N,N'-dimethylformamide, and N,N'-diethylformamide. The observed X-ray powder diffraction pattern is shown in FIG. 25a, and the pattern simulated from the single X-Ray data is shown in FIG. 25b. Comparison of these two patterns confirms the purity of the as-synthesized IRMOF-12.

Elemental analysis for IRMOF-12: $C_{70}H_{80}NO_{25}ClZn_4=Zn_4O(TPDC)_3.(11H\ O).(CHP).$(chlorobenzene) Calcd C, 51.50; H, 4.94; N, 0.86. Found C, 51.64; H, 3.73; N, 1.01.

Figure 26:
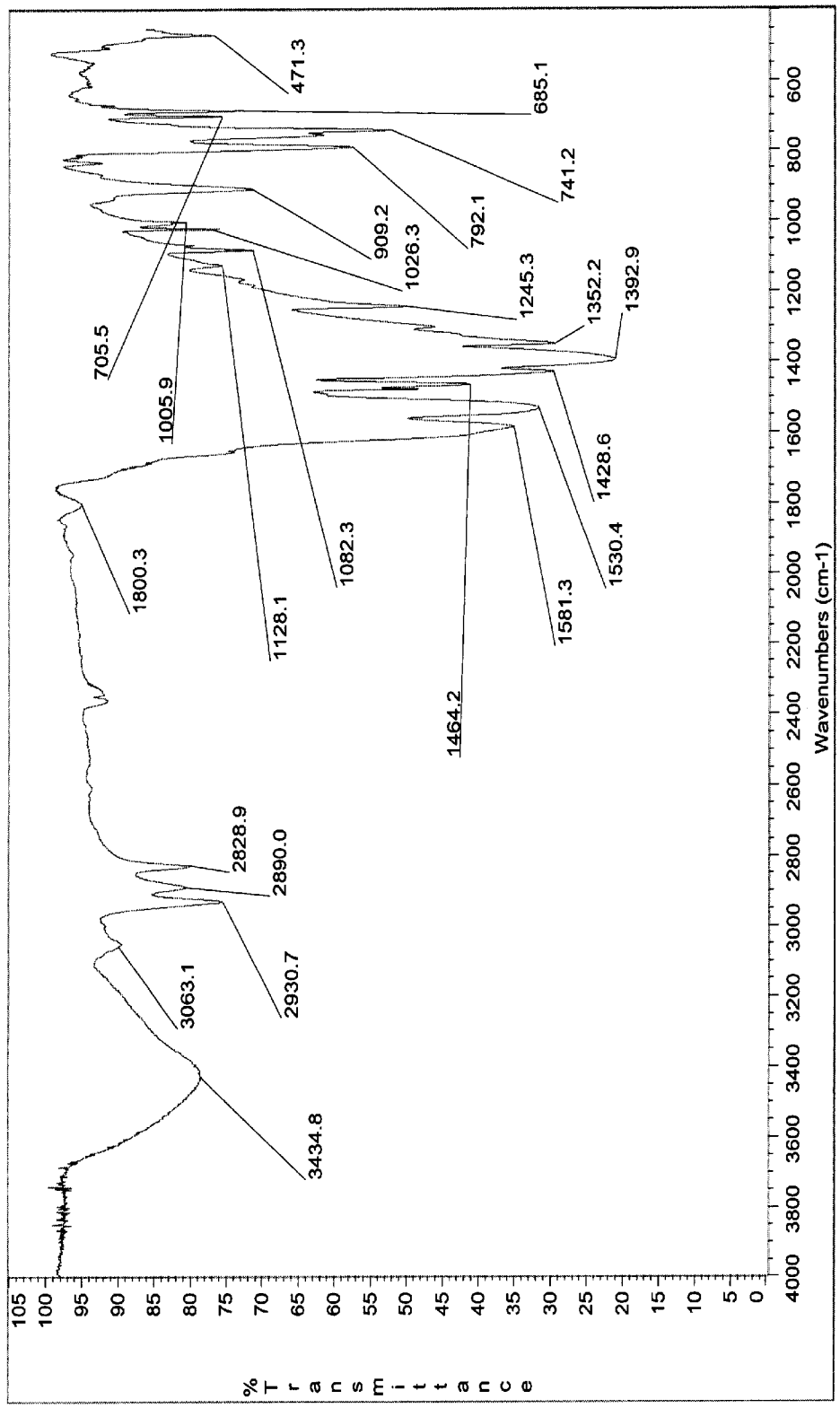
FIG. 26 is a graphic representation of InfraRed spectrum for IRMOF-12 of the present invention.

Infra-Red spectra for IRMOF-12 (FIG. 26):

FT-IR for IRMOF-12 FT-IR (KBr, 4000–400 cm$^{-1}$): 3434 (br), 3063 (w), 2931 (w), 2890 (w), 2829 (w), 1800 (w), 1581 (s), 1530 (s), 1464 (m), 1429 (s), 1393 (vs), 1352 (s), 1245 (w), 1128 (w), 1082 (w), 1026 (w), 1006 (w), 909 (w), 792 (w), 741 (w), 706 (w), 685 (w), 471 (w).

Thermogravimetric analysis of IRMOF-12: A crystalline sample (16.527 mg) was heated from 30° C. to 900° C. at constant rate (5.0° C./min); two separate weight-loss steps were observed. The first weight loss step (38.1%) at 250° C. corresponds to the removal of (4H$_2$O+9DMF) and the second one (41.8%) to the decomposition of the framework. A pseudo-plateau was observed between 250° C.–400° C. corresponding to the stability of IRMOF-6 up to 400° C.

Figure 24:
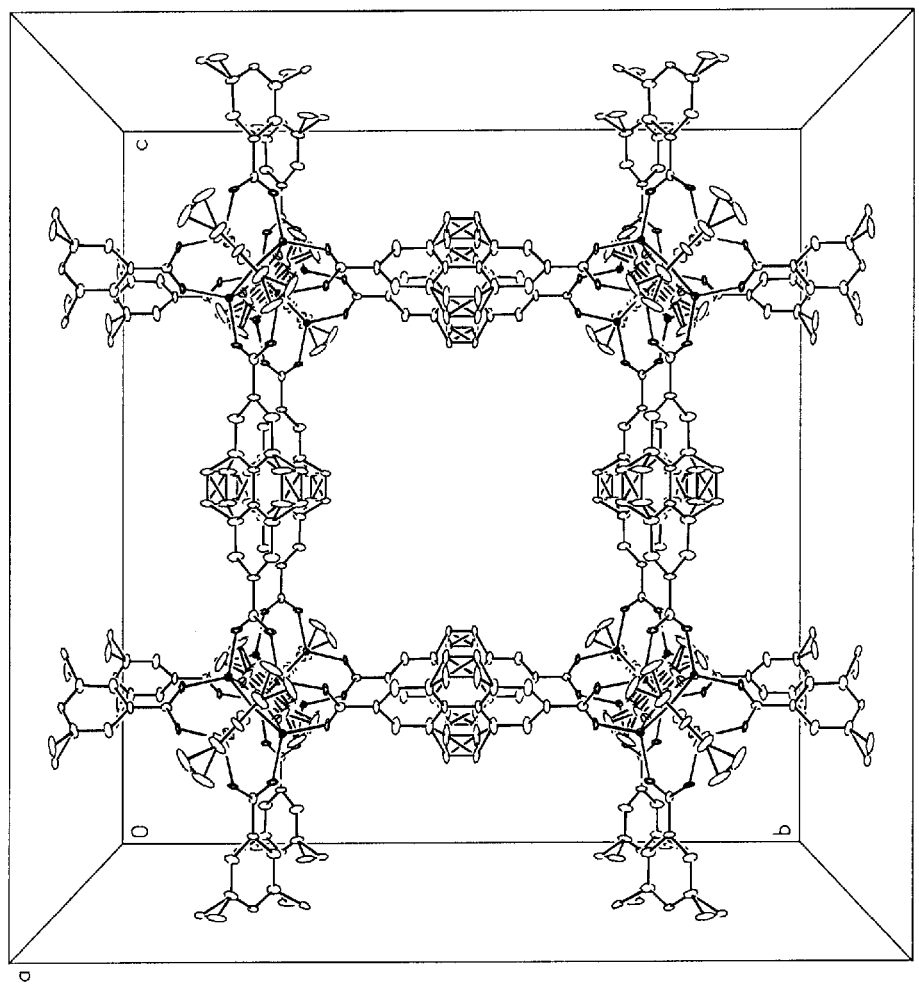
FIG. 24 is a diagrammatic representation of a crystal structure for IRMOF-12 of the present invention.

The resultant IRMOF-12 crystals were fully characterized as discussed above. The crystallographic parameters and a representative picture of the framework are summarized in FIG. 24. The elemental analysis confirms the composition as shown above, the Infrared confirms that the carboxylates are fully deprotonated. The overlap of the observed and simulated XRPD confirms the purity of the sample.

Preparation of IRMOF-13:

$Zn_4O(PDC)_3.4H_2O.\ 6DEF$ (IRMOF-13): Exact amounts of ppyrene-2,7- dicarboxylic acid, $H_2TPDC$ (0.014 g, 0.048 mmol), and zinc nitrate hexahydrate, $Zn(NO_3)_2.4H_2O$ (0.080 g, 0.31 mmol), were dissolved in diethylformamide, DEF, (6.0 mL) and placed in a Parr Teflon-lined stainless vessel (23 mL). The vessel was sealed and heated to 85° C. for 24 h at a rate of 2.0° C./min and cooled to room temperature at a rate of 2.0° C./min.

Figure 33:
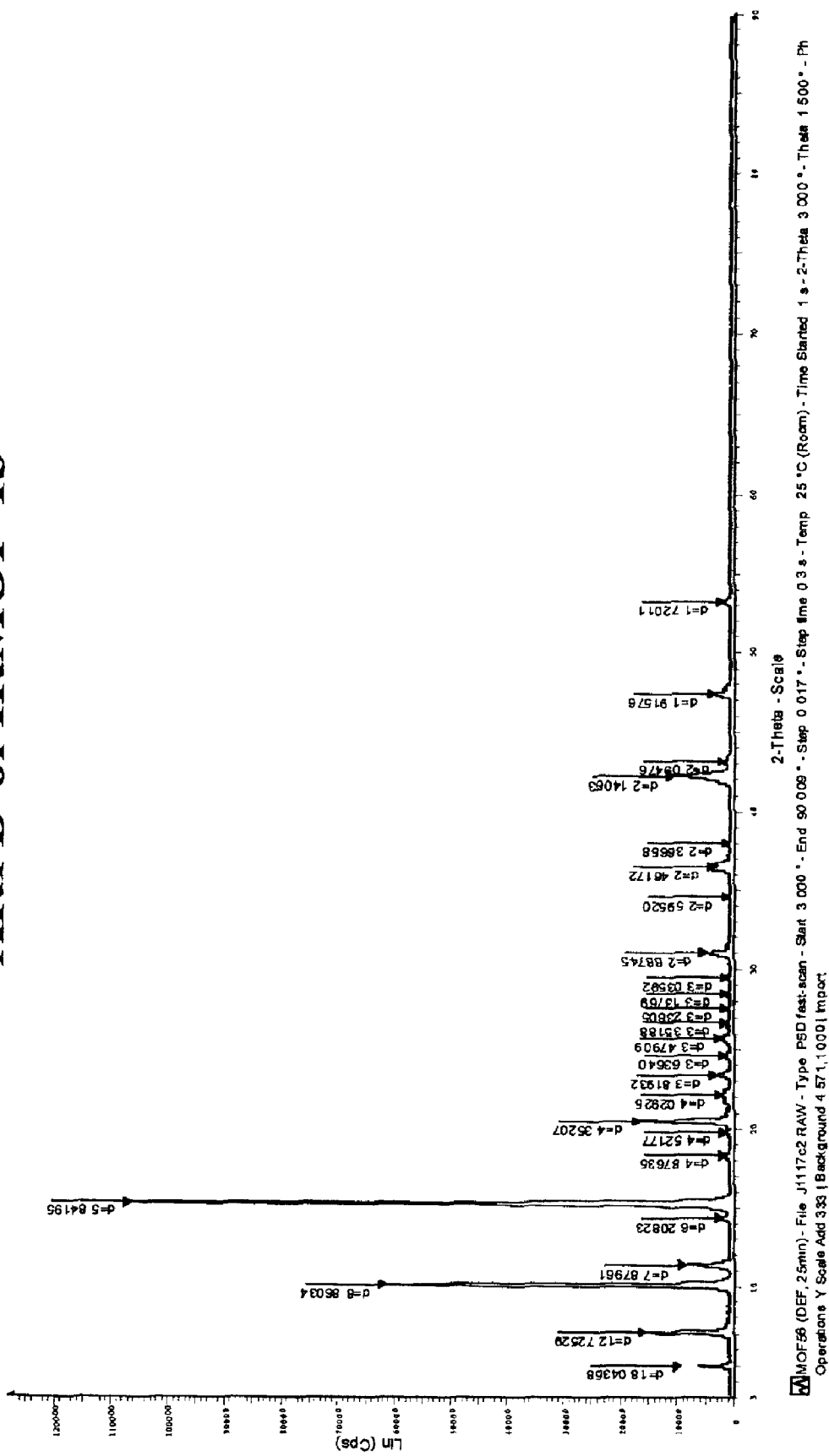
FIG. 33 is a graphic representation of XRPD of IRMOF-13 of the present invention.

The resultant product, rectangular, pale yellow crystals, was filtered, washed with a DEF and ethanol mixture (3×5 ml) to yield 63% of IRMOF-13. The as-synthesized IRMOF-13 is insoluble in water and all common organic solvents such as ethanol, acetonitrile, tetrahydrofuran, chloroform, dichloromethane, acetone, N,N'-dimethylformamide, and N,N'-diethylformamide. The observed X-ray powder diffraction (XRPD) is shown in FIG. 33.

Elemental analysis for IRMOF-13: $C_{84}H_{98}N_6O_{23}Zn_4=Zn_4O(PDC)_3.(4H_2O).(6DEF)$ Calcd C, 55.40; H, 5.42; N, 4.61. Found C, 55.56; H, 2 0 4.85; N, 4.35.

Figure 34:
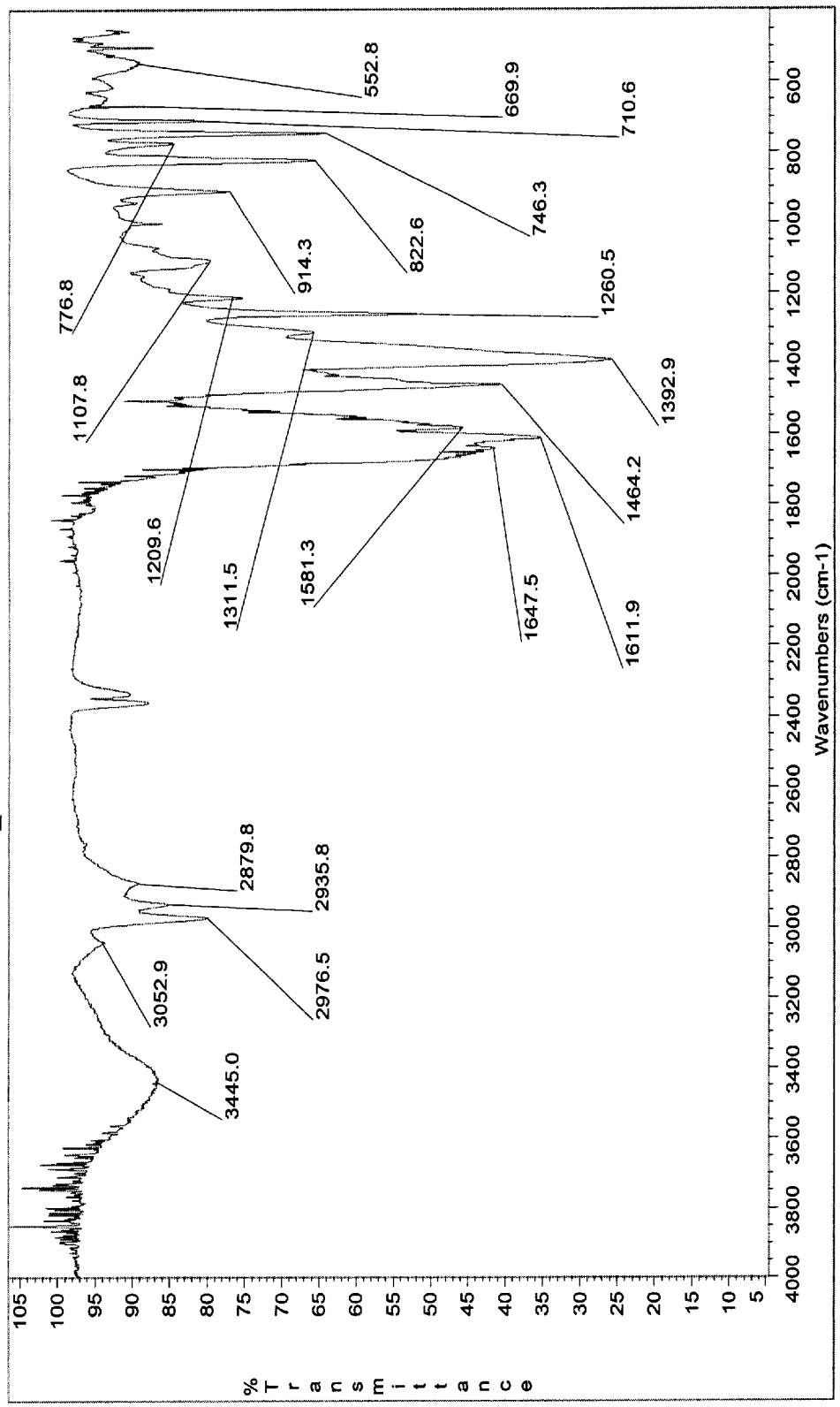
FIG. 34 is graphic representation of an InfraRed spectrum for IRMOF-13 of the present invention.

Infra-Red spectra for IRMOF-13 (FIG. 34): FT-IR for IRMOF-13 (KBr, 4000–400 cm$^{-1}$): 3445 (br), 2977 (w), 2936 (w), 2880 (w), 1648 (s), 1612 (s), 1581 (s), 1464 (s), 1393 (vs), 1312 (w), 1261 (m), 1209 (w), 1108 (w), 914 (w), 823 (w), 777 (w), 746 (w), 711 (w), 670 (w), 553 (w).

Thermogravimetric analysis for IRMOF-13: A crystalline sample (22.256 mg) was heated from 25° C. to 700° C. at a constant rate (5.0° C./min); two separate weight-loss steps were observed. The first weight loss (31.4%) step below 300° C. corresponds to the removal of (4H$_2$O+6DEF) and the second one above 420° C. (42.7%) to the framework decomposition. A pseudo-plateau between 300–420° C. was observed, proving the stability of IRMOF-13.

The resultant crystals were collected and fully characterized. The elemental analysis confirms the composition as shown above, and the Infrared confirms that the carboxylates are fully deprotonated, and that expected M$_4$O(CO$_2$)$_6$ cluster is incorporated in structure.

Preparation of IRMOF-14:

Method 1: Exact amounts of pyrene-2,7- dicarboxylic acid, H$_2$PDC (0.005 g, 0.017 mmol), and zinc nitrate hexahydrate, Zn(NO$_3$)$_2$.4H$_2$O (0.031 g, 0.12 mmol), were dissolved in diethylformamide, 16 ml, DEF and placed in a Parr Teflon-lined stainless vessel (23 mL). The vessel was sealed and heated to 85° C. for 24 h at a rate of 2.0° C./min and cooled to room temperature at a rate of 2.0° C./min. The resultant product was filtered, washed with a DEF (3×5 mL) to yield 70% of IRMOF-14.

Elemental analysis: C$_{84}$H$_{100}$O$_{24}$N$_6$Zn$_4$=Zn$_4$O(PDC)$_3$.(H$_2$O)$_5$(DEF)$_6$ Calcd C, 54.85; H, 5.48; N, 4.57. Found C, 53.94; H, 5.37; N, 4.72.

FT-IR (KBr, 3500–400 cm$^{-1}$): 3455 (br), 2982 (m), 2935 (w), 1658 (s), 1607 (s), 1581 (m), 1464 (m), 1393 (s), 1261 (m), 1220 (w), 1113 (w), 914 (w), 827 (m), 751 (w), 711 (w), 511 (w).

Figure 31A:
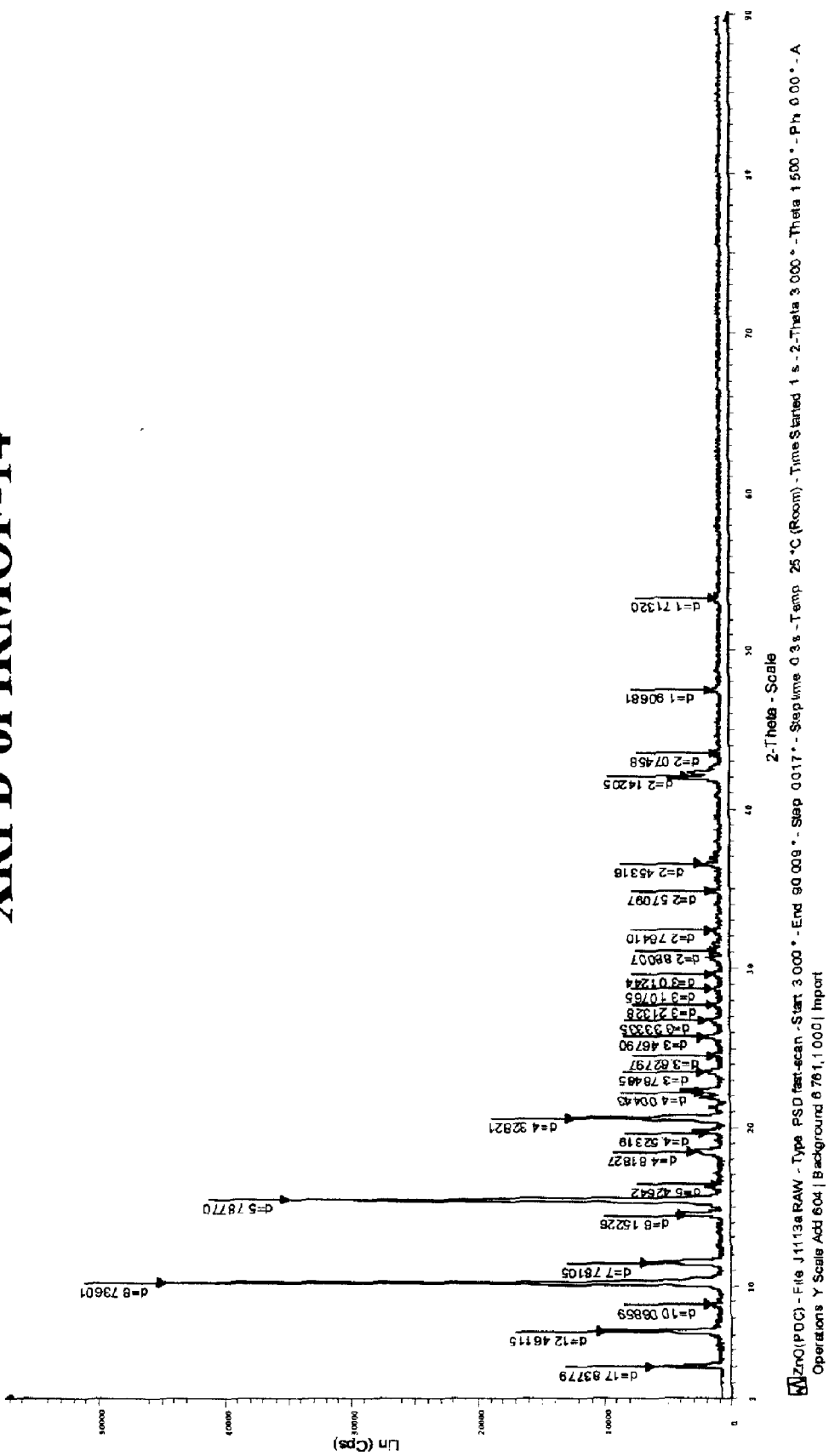
FIG. 31a is a graphic representation of XRPD of IRMOF-14 of the present invention.
Figure 31B:
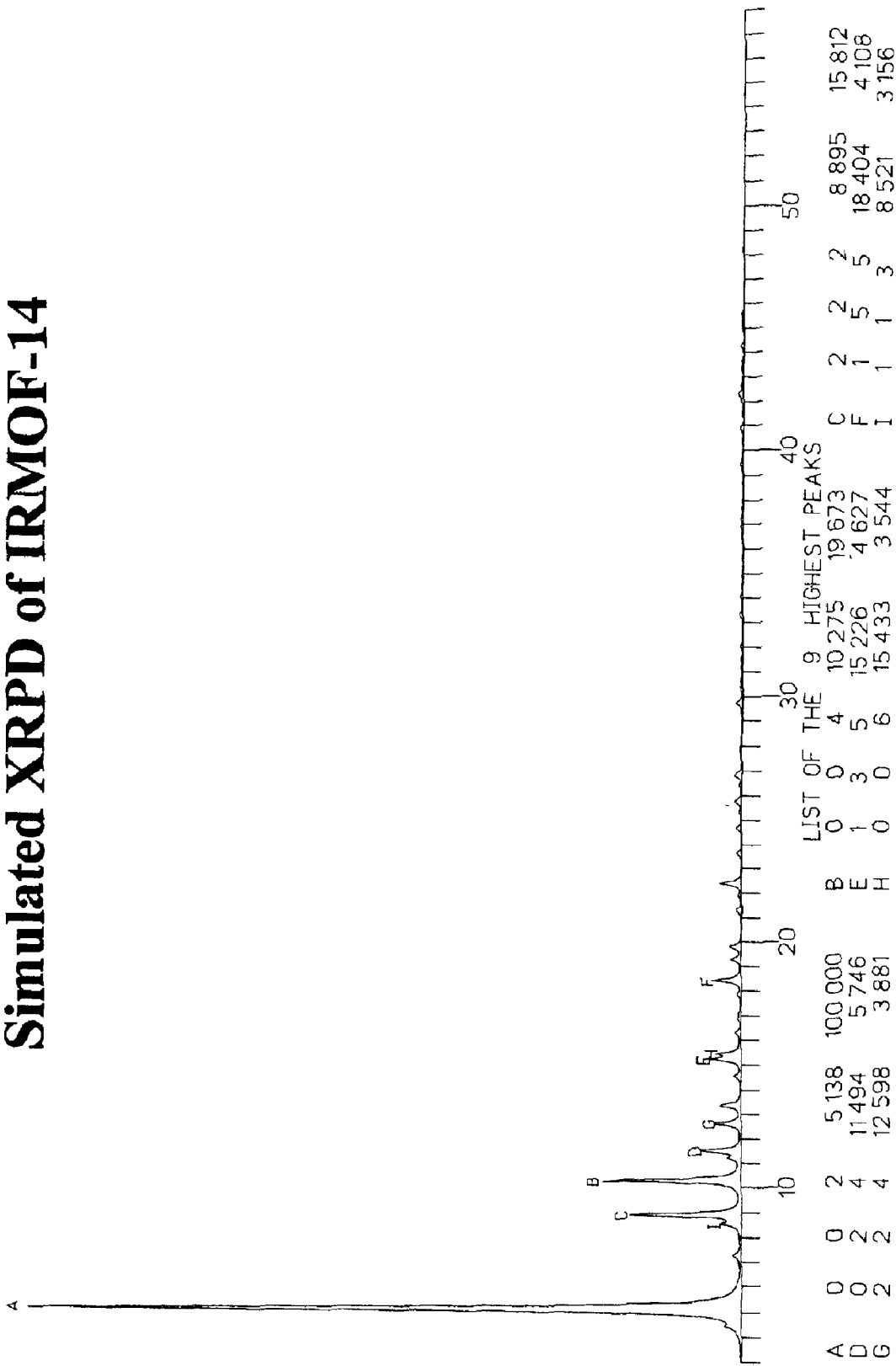
FIG. 31b is a graphic representation of a simulated XRPD of IRMOF-14 of the present invention.

Method 2: Zn$_4$O(PDC)$_3$.4H$_2$O.½CHP.10chlorobenzne (IRMOF-14): A mixture of dimethylformamide and isopropanol DMF/2-C$_3$H$_8$OH: 6/1 ml containing pyrene-dicarboxylic acid, H$_2$PDC (0.014 g, 0.048 mmol), and zinc nitrate tetrahydrate, Zn(NO$_3$)$_2$.4H$_2$O (0.080 g, 0.31 mmol), was placed in a Parr Teflon-lined stainless vessel (23 mL). The vessel was sealed and heated to 85° C. for 24 h at a rate of 2.0° C./min and cooled to room temperature at a rate of 2.0° C./min. The filtrate solution from six vessels (35 mL) was diluted with CHP (1-cyclohexyl-2-pyrrolidinone) (15.0 mL). The final solution was divided equally, transferred into five vials, and exposed to diluted triethylamine. The diluted triethylamine solution was prepared by diluting 0.10 mL of the stock solution (triethylamine: chlorobenzene=1:10, v/v) with 5.0 mL of chlorobenzene. After two weeks pale brown crystals were produced. The resultant product was filtered, washed with a DMF and chlorobenzene mixture (3×5 mL) to yield 6% of IRMOF-14. The as-synthesized IRMOF-14 is insoluble in water and all common organic solvents such as ethanol, acetonitrile, tetrahydrofuran, chloroform, dichloromethane, acetone, N,N'-dimethylformamide, and N,N'-diethylformamide. Comparison of the observed X-ray powder diffraction pattern shown in FIG. 31$a$ and the simulated pattern from the single X-Ray data (FIG. 31$b$) confirms the purity of the as-synthesized IRMOF-14.

Elemental analysis for IRMOF-14: C$_{119}$H$_{90.5}$NO$_{0.5}$O$_{17.5}$Cl$_{10}$Zn$_4$=Zn$_4$O(PDC)$_3$.(4H$_2$O).(½CHP).(10chlorobenzne) Calcd C, 58.97; H, 3.76; N, 0.29. Found C, 58.68; H, 3.64; N, 0.30.

Figure 32:
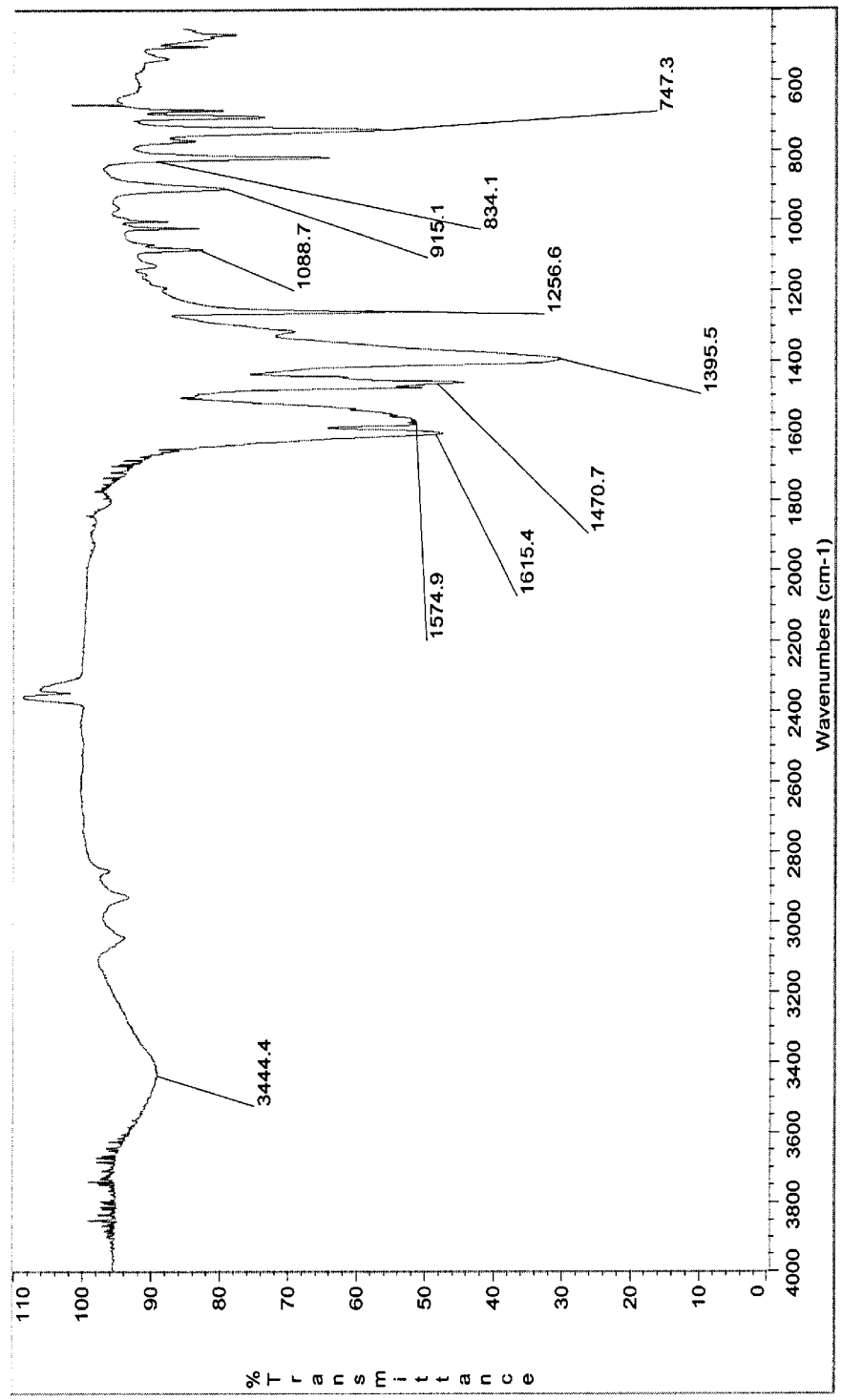
FIG. 32 is a graphic representation of an InfraRed spectrum for IRMOF-14 of the present invention.

Infra-Red spectra for IRMOF-14 (FIG. 32):

FT-IR for IRMOF-14 FT-IR (KBr, 4000–400 cm$^{-1}$): 3430 (br), 3048 (w), 2936 (w), 2854 (w), 1607 (m), 1571 (m), 1464 (m), 1393 (vs), 1317 (w), 1261 (m), 1087 (w), 909 (w), 823 (w), 746 (m), 706 (w), 685 (w), 471 (w).

Thermogravimetric analysis of IRMOF-14: A crystalline sample (12.000 mg) was heated from 30° C. to 800° C. at 10.0° C./min; two separate weight-loss steps were observed. The first weight loss (52.4%) step at 250° C. is attributed to the removal of (4H$_2$O+½CHP+10chlorobenzne) and the second one (34.9%) to the framework decomposition. A pseudo plateau was observed between 250–300° C. indicating the stability of IRMOF-14 up to 300° C.

Figure 30:
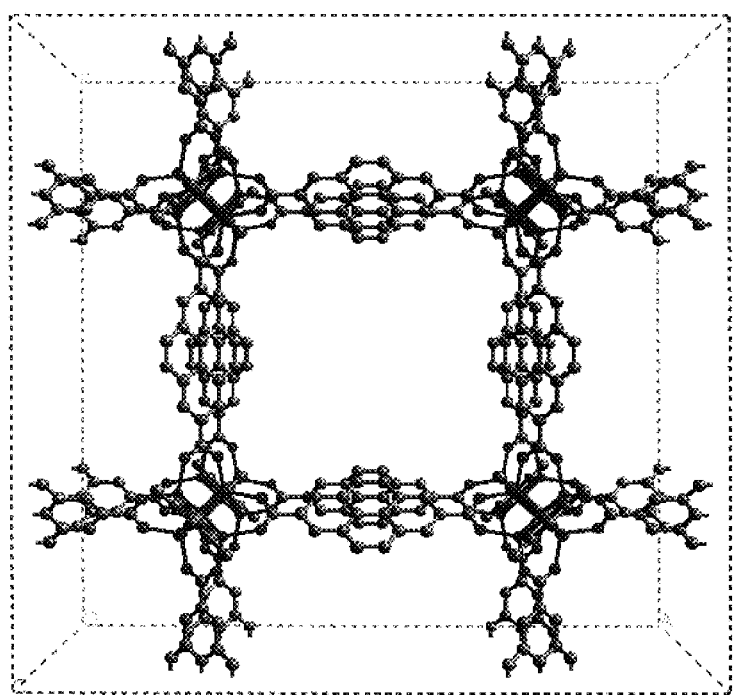
FIG. 30 is a diagrammatic representation of a crystal structure for IRMOF-14 of the present invention.

The resultant IRMOF-14 crystals, after two weeks, were collected and fully characterized. The crystallographic parameters and a representative picture of the framework are summarized in FIG. 30. The elemental analysis confirms the composition as shown above, the Infrared confirms that the carboxylates are fully deprotenated. The overlap of the observed and simulated XRPD confirms the purity of the sample.

Figure 35:
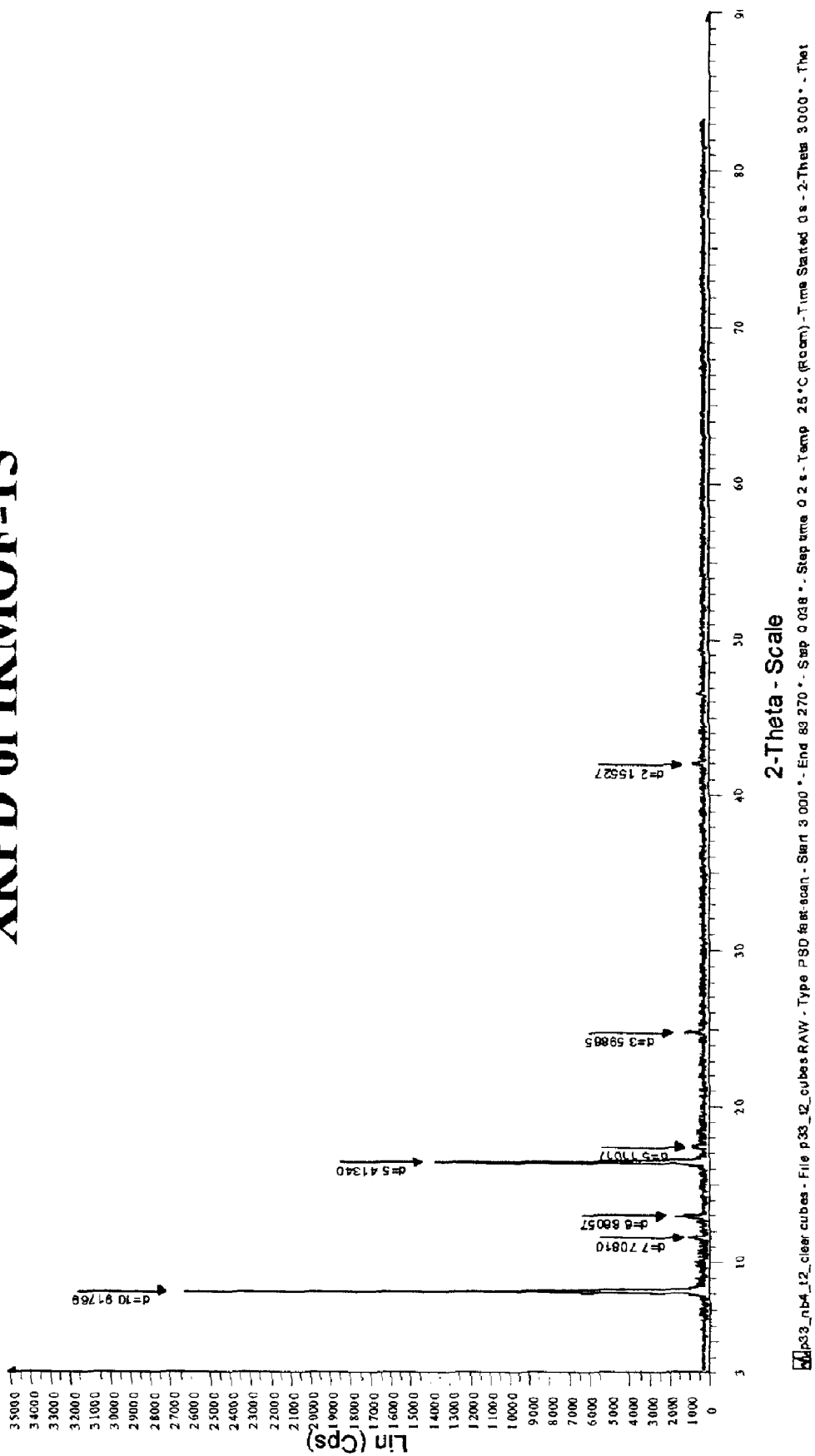
FIG. 35 is a graphic representation of XRPD of IRMOF-15 of the present invention.

Preparation of IRMOF-15:

Zn$_4$O(TPDC)$_3$.(DEF)$_x$ (IRMOF-15): Exact amounts of terphenyldicarboxylic acid, H$_2$TPDC (0.002 g, 0.0063 mmol), and zinc nitrate hexahydrate, Zn(NO$_3$)$_2$·6(H$_2$O) (0.0075 mg, 0.025 mmol), were dissolved in 1.5 ml diethylformamide (DEF) and placed in a pyrex tube (100 mm, 6 ml). The evacuated tube was sealed and heated to 100° C. for 24 h at a rate of 2.0° C./min and cooled to room temperature at a rate of 0.1° C./min. The resultant clear cubic crystals were washed with DEF. The X-ray powder diffraction pattern shown in FIG. 35 confirms the homogeneity of the as-synthesized product and is attributed as IRMOF-15.

The ability to design and construct solid-state materials with pre-determined structures is a significant challenge in chemistry. The present inventive strategy, based on reticulating metal ions and organic linking compounds into extended networks, has been advanced to a point that has allowed the design of porous structures in which pore size and functionality can be varied systematically. MOF-5, a prototype of a new class of porous materials and one that is constructed from octahedral Zn—O—C clusters and benzene links, was used as one example to demonstrate that its 3-D porous system can be functionalized with the organic groups, —Br, —NH2, —OC$_3$H7, —OC$_5$H$_{11}$, —H$_4$C$_2$, and —H$_4$C$_4$, and its pore size expanded with the long molecular struts biphenyl, tetrahydropyrene, pyrene, and terphenyl. The ability to direct the formation of the octahedral clusters in the presence of a desired carboxylate link may be, in certain instances, an important feature of this strategy, which resulted in the design of an isoreticular (having the same framework topology) series of sixteen well-defined materials whose crystals have open space representing up to 91.1 % of the crystal volume, and homogeneous periodic pores that can be incrementally varied from 3.8 to 28.8 angstroms. The deliberate control exercised at the molecular level in the design of these crystals of an embodiment of the present invention is expected to have tremendous implications on materials properties and future technologies. This is in sharp contrast to the unpredictable nature of zeolite and other molecular sieve syntheses. Indeed, data indicate that members of this series of materials of an embodiment of the present invention represent the first monocrystalline mesoporous organic/inorganic frameworks, and exhibit a very high capacity for methane storage (155 cm$^3$/cm$^3$ at 36 atm). This is the highest methane storage capacity in any crystalline porous material to date. Members of this inventive series of materials also exhibit the lowest densities (0.41 to 0.21 g/cm$^3$) attained to date for any crystalline material at room temperature.

Elemental analysis: $C_{84}H_{100}O_{24}N_6Zn_4=Zn_4O(TPDC)_3 \cdot (H_2O)_5(DEF)$ Calcd C, 55.07; H, 4.05; N, 0.99. Found C, 55.05; H, 3.80; N, 0.66.

Figure 36:
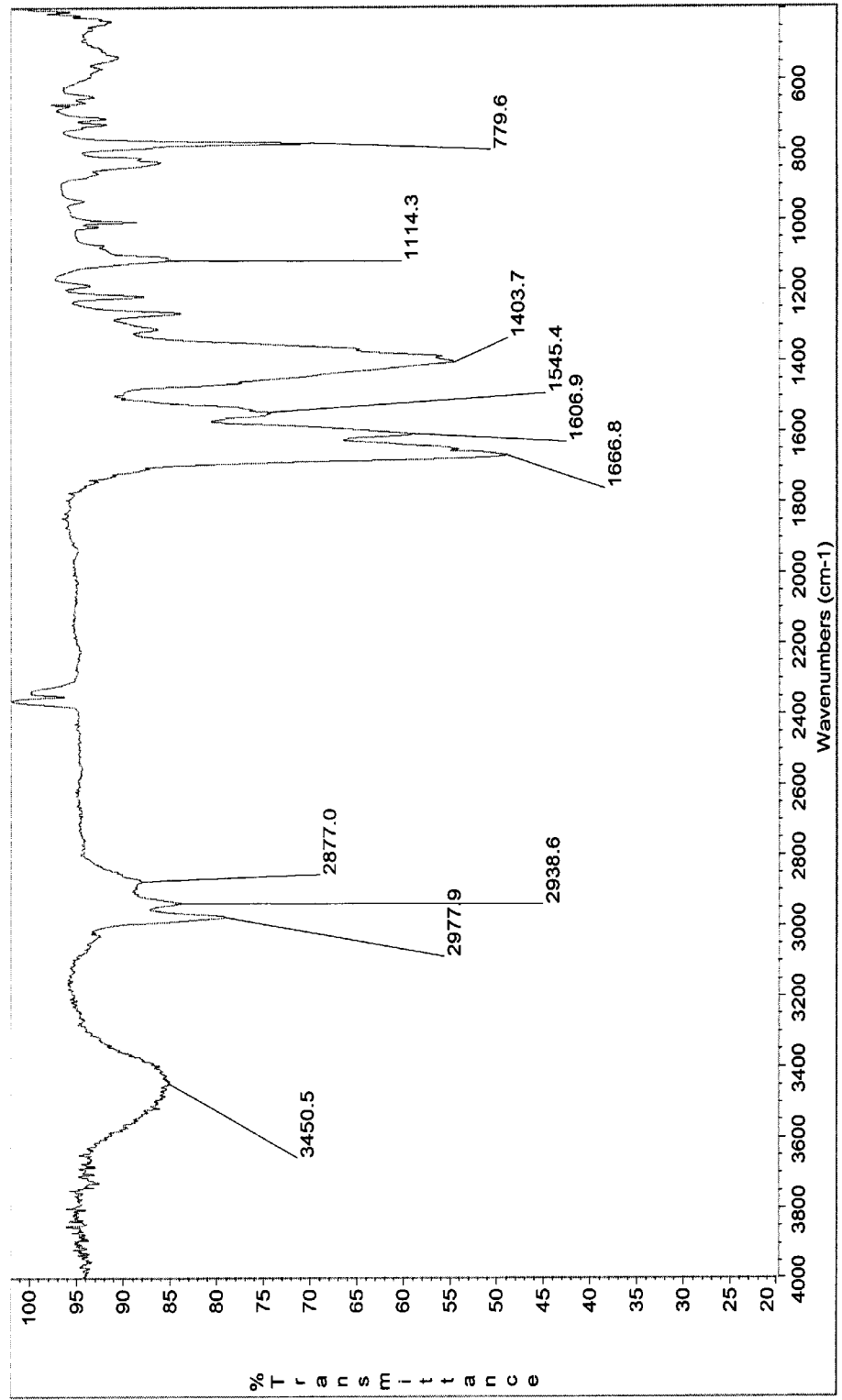
FIG. 36 is a graphic representation of an InfraRed spectrum for IRMOF-15 of the present invention.

Infra-Red spectra for IRMOF-15 (FIG. 36):

FT-IR for IRMOF-15 (KBr, 4000–400 cm$^{-1}$): 3451 (br), 2978 (w), 2939 (w), 2877 (w), 1667 (s), 1607 (s), 1545 (w), 1404 (vs), 1393 (vs), 1114 (w), 780 (w).

The resultant IRMOF-15 clear cubic crystals were collected and characterized. The IR data point to the presence of $M_4O(CO_2)_6$ cluster and therefore coordinated with the observed XRPD for the as-synthesized material assigned as IRMOF-15.

Preparation of IRMOF-16

Exact amounts of terphenyldicarboxylic acid, H$_2$TPDC (0.004 g, 0.0126 mmol), and zinc nitrate hexahydrate, Zn(NO$_3$)$_2 \cdot _6$(H$_2$O) (0.015 mg, 0.05 mmol), were dissolved in 1.0 ml N-methylpyrilidone (NMP). The solution was diluted with 1 ml diethylformamide (DEF) and placed in a pyrex tube (100 mm, 6 ml). The evacuated tube was sealed and heated to 95° C. for 24 h at a rate of 2.0° C./min, then to 100° C. for 48 h at a constant rate of 2.0° C./min and cooled to room temperature at a rate of 2.0° C./min. The resultant clear cubic crystals were filtered and washed with DEF (3×5 mL) to yield IRMOF-16.

Elemental analysis: $C_{145}H_{227}O_{32}N_{17}Zn_4=Zn_4O(TPDC)_3 \cdot (DEF)_{17}(H_2O)_2$ Calcd C, 58.40; H, 7.99; N, 7.99. Found C, 58.37; H, 7.97; N, 8.01.

FT-IR (KBr, 4000–400 cm$^{-1}$): 3425 (br), 2971 (w), 2931 (w), 2880 (w), 1678 (s), 1607 (s), 1409 (s), 1301 9w), 1266 (w), 1118 (w), 1011 (w), 843 (w), 777 (m), 736 (w), 563 (w).

While preferred embodiments of the invention have been described in detail, it will be apparent to those skilled in the art that the disclosed embodiments may be modified. Therefore, the foregoing description is to be considered exemplary rather than limiting, and the true scope of the invention is that defined in the following claims.

What is claimed is:

1. A systematically formed isoreticular metal-organic framework (IRMOF), consisting essentially of:

a plurality of secondary building units (SBUs), each of the plurality of SBUs comprising an $M_4O(CO_2)_6$ cluster; and a compound linking adjacent SBUS, the linking compound comprising a linear ditopic carboxylate having at least one substituted phenyl group and at least one functional group X attached to the at least one substituted phenyl group;

wherein the IRMOF has a substantially permanent porosity and is substantially stable;

wherein the functional group X is at least one of hydrogen, amines, halides, an R group selected from at least one of linear, substituted or cyclo alkanes, alkenes, alkynes, chains, and ether O—R, wherein R is at least one of linear, substituted or cyclo alkanes, alkenes, alkynes, chains, and mixtures thereof; and M is a metal cation;

and wherein at least one of functionality, dimension, pore size and free volume of the IRMOF is substantially determined by the linking compound.

2. The IRMOF as defined in claim 1 wherein the linking compounds are selected from the group consisting of:

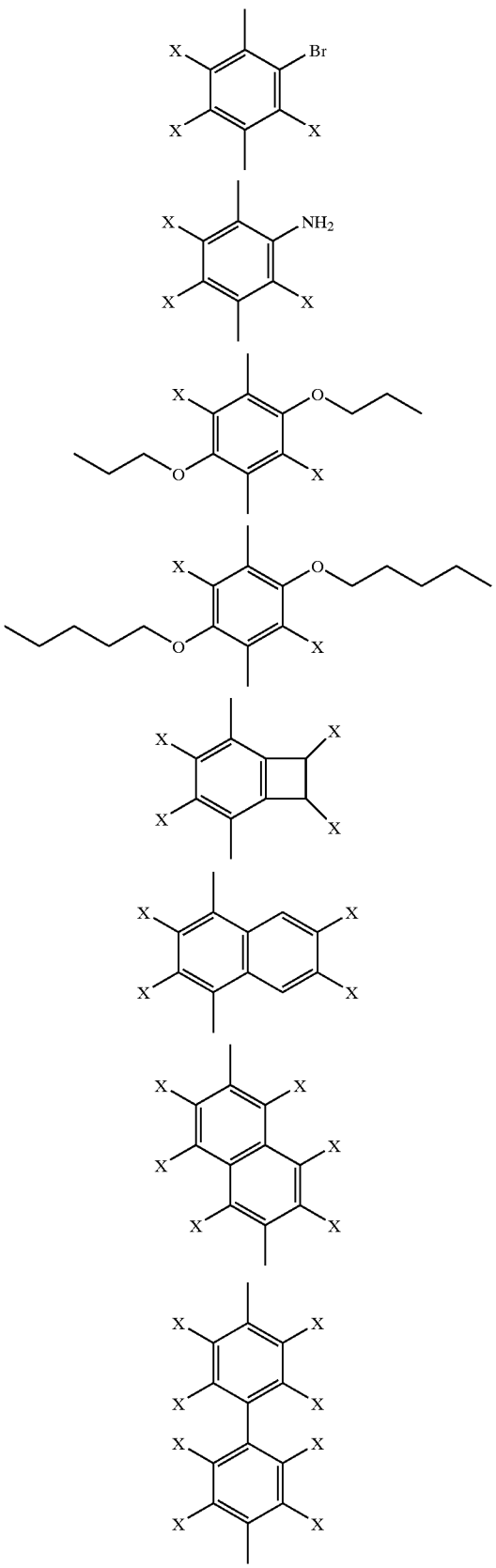

-continued

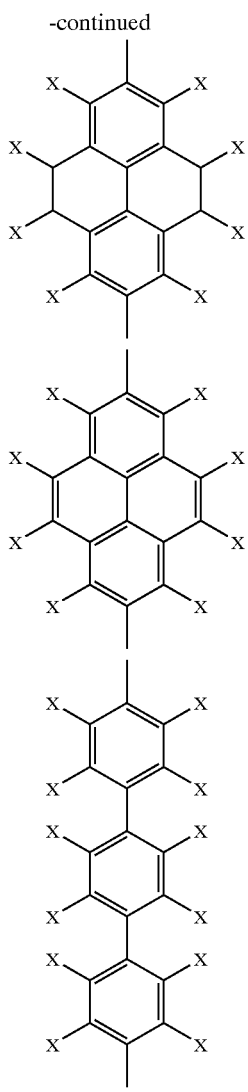

wherein the functional group X is at least one of hydrogen, amines, halides, an R group selected from at least one of linear, substituted or cyclo alkanes, alkenes, alkynes, chains, and ether O—R, wherein R is at least one of linear, substituted or cyclo alkanes, alkenes, alkynes, chains, and mixtures thereof.

3. The IRMOF as defined in claim 2 wherein X comprises at least one of primary, secondary or tertiary amines; aromatic amines, pyridine, pyrimidine like 5 or 6 membered rings; halides including substituted —RX; alcohols: ROH; thiols: RSH; sulfonates —R—$SO_3$; nitro groups —R($NO_2^-$); phosphates —R—$PO_2^-$; epoxides; aldehydes (RCOH); ketones (RCOR); esters $RCO_2R$; carboxylic acids; cycloalkenes; cycloalkynes; silyls derivatives; boranes derivatives; ferrocenes, other metallocenes, and mixtures thereof.

4. The IRMOF as defined in claim 1 wherein M in the SBU is a metal cation of a metal chosen from at least one of beryllium, zinc, cadmium, mercury, any of the transition metals in the periodic table, scandium through copper, yttrium through silver, lanthanum through gold, and all known elements from actinium on.

5. A method of systematically forming an isoreticular metal-organic framework (IRMOF), the method comprising the steps of:

dissolving at least one source of metal cations and at least one organic linking compound in a solvent to form a solution, the at least one organic linking compound comprising a linear ditopic carboxylate having at least one substituted phenyl group; and crystallizing the solution under predetermined conditions to form a predetermined IRMOF;

wherein at least one of functionality, dimension, pore size and free volume of the IRMOF is substantially determined by the organic linking compound.

6. The method as defined in claim 5 wherein the at least one source of metal cations is a metal salt formed from a metal cation and an anion, the metal cation being a cation of a metal selected from the group consisting of zinc, cadmium, mercury, and transition metals, and wherein the anion is selected from the group consisting of $F^-$, $Cl^-$, $Br^-$, $I^-$, $ClO_2^-$, $ClO_3^-$, $ClO_4^-$, $OH^-$, $NO_3^-$, $NO_2^-$, $SO_4^{2-}$, $SO_3^{2-}$, $PO_4^{3-}$, $CO_3^{2-}$, $CH_3CO_2-$, $HCO_2^-$ and $CF_3SO_3^-$, $B_4O_7^{2-}$ and $PF_6^-$.

7. The method as defined in claim 6 wherein at least one functional group X is attached to the at least one substituted phenyl group.

8. The method as defined in claim 5 wherein the predetermined conditions are at least one of: leaving the solution at room temperature; adding a diluted base to the solution to initiate the crystallization; diffusing a diluted base into the solution to initiate the crystallization; and transferring the solution to a closed vessel and heating to a predetermined temperature.

9. A systematically formed isoreticular metal organic framework (IRMOF), consisting essentially of:

a plurality of secondary building units (SBUs), each of the plurality of SBUs comprising an $M_4O(CO_2)_6$ cluster, wherein M is a metal cation; and a compound linking adjacent SBUs, the linking compound comprising a linear ditopic carboxylate having at least one substituted phenyl group and at least one functional group X attached to the at least one substituted phenyl group;

wherein the IRMOF has a substantially permanent porosity and is substantially stable;

wherein at least one of functionality, dimension, pore size and free volume of the IRMOF is substantially determined by the linking compound;

and wherein the IRMOF is adapted to store at least one gas.

10. A systematically formed isoreticular metal organic framework (IRMOF), consisting essentially of:

a plurality of secondary building units (SBUs), each of the plurality of SBUs comprising an $M_4O(CO_2)_6$ cluster, wherein M is a metal cation; and a compound linking adjacent SBUs, the linking compound comprising a linear ditopic carboxylate having at least one phenyl group and at least one functional group X attached to the at least one phenyl group;

wherein the IRMOF has a substantially permanent porosity and is substantially stable;

wherein at least one of functionality, dimension, pore size and free volume of the IRMOF is substantially determined by the linking compound;

and wherein the IRMOF is adapted to store methane.

11. The IRMOF as defined in claim 1 wherein the density of the IRMOF is between about 1.0 g/cm³ and about 0.2 g/cm³.

12. The IRMOF as defined in claim 11 wherein the density of the IRMOF is between about 0.41 g/cm³ and about 0.21 g/cm³.

13. The IRMOF as defined in claim 10, wherein the methane storage capacity is about 155 cm$^3$/cm$^3$.

14. The method as defined in claim 5 wherein the at least one source of metal cations is a plurality of secondary building units (SBUs).

15. The method as defined in claim 14 wherein each of the SBUs is a multi-metal nuclear carboxylate cluster.

16. The method as defined in claim 15 wherein the multi-metal nuclear carboxylate cluster is $M_4O(CO_2)_6$.

17. A method of systematically forming an isoreticular metal-organic framework (IRMOF), the method comprising the steps of:

dissolving at least one source of metal cations and at least one organic linking compound in a solvent to form a solution; and crystallizing the solution under predetermined conditions to form a predetermined IRMOF;

wherein at least one of functionality, dimension, pore size and free volume of the IRMOF is substantially determined by the organic linking compound;

wherein the at least one source of metal cations is a metal salt formed from a metal cation and an anion, the metal cation being a cation of a metal selected from the group consisting of zinc, cadmium, mercury, and transition metals, and wherein the anion is selected from the group consisting of F$^-$, Cl$^-$, Br$^-$, I$^-$, ClO$^-$, ClO$_2^-$, ClO$_3^-$ClO$_4^-$, OH$^-$, NO$_3^-$, NO$_2^-$, SO$_4^{2-}$, SO$_3^{2-}$, PO$_4^{3-}$, CO$_3^{2-}$, CH$_3$CO$_2^-$, HCO$_2^-$ and CF$_3$SO$_3^-$, B$_4$O$_7^{2-}$ and PF$_6^-$;

wherein the at least one organic linking compound is a linear ditopic carboxylate having at least one substituted phenyl group;

and wherein the linear ditopic carboxylate is selected from the group consisting of;

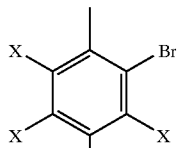

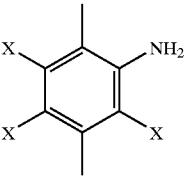

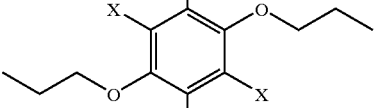

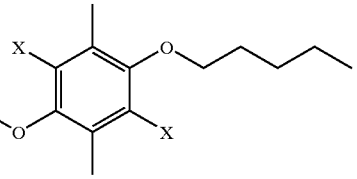

-continued

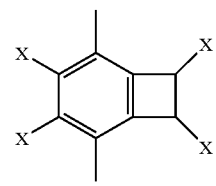

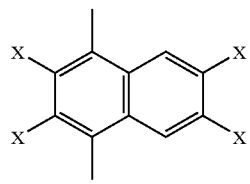

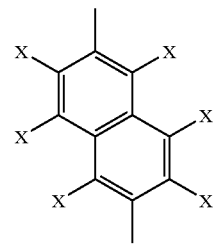

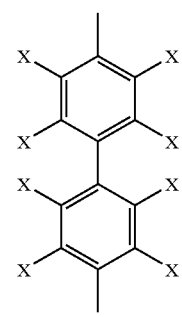

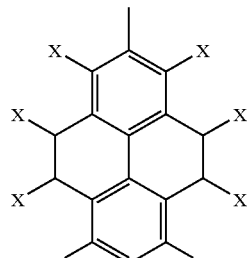

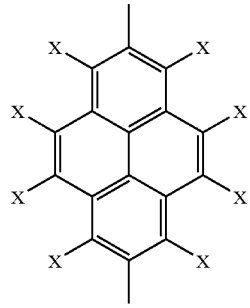

-continued

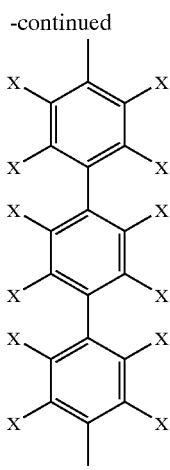

wherein the functional group X is at least one of hydrogen, amines, halides, an R group comprising at least one of linear, substituted or cyclo alkanes, alkenes, alkynes, chains, and ether O—R, wherein R is at least one of linear, substituted or cyclo alkanes, alkenes, alkynes, chains, and mixtures thereof.

18. The method as defined in claim 17 wherein X comprises at least one of primary, secondary or tertiary amines; aromatic amines, pyridine, pyrimidine like 5 or 6 membered rings; halides including substituted —RX; alcohols: ROH; thiols: RSH; sulfonates —R—$SO_3$; nitro groups —R($NO_2^-$); phosphates —R—$PO_2^-$; epoxides; aldehydes (RCOH); ketones (RCOR); esters $RCO_2R$; carboxylic acids; cycloalkenes; cycloalkynes; silyls derivatives; boranes derivatives; ferrocenes, other metallocenes, and mixtures thereof.

19. The method as defined in claim 5 wherein the metal cation is a cation of a metal chosen from at least one of beryllium, zinc, cadmium, mercury, any of the transition metals in the periodic table, scandium through copper, yttrium through silver, lanthanum through gold, and all known elements from actinium on.

20. A method of systematically forming an isoreticular metal-organic framework (IRMOF), the method comprising the steps of:
    dissolving at least one source of metal cations and at least one organic linking compound in a solvent to form a solution, the at least one organic linking compound comprising a linear ditopic carboxylate having at least one substituted phenyl group;
    crystallizing the solution under predetermined conditions to form a predetermined IRMOF; and
    storing at least one gas within the IRMOF;
    wherein at least one of functionality, dimension, pore size and free volume of the IRMOF is substantially determined by the organic linking compound.

21. A method of systematically forming an isoreticular metal-organic framework (IRMOF), the method comprising the steps of:
    dissolving at least one source of metal cations and at least one organic linking compound in a solvent to form a solution;
    crystallizing the solution under predetermined conditions to form a predetermined IRMOF; and
    storing methane within the IRMOF;
    wherein at least one of functionality, dimension, pore size and free volume of the IRMOF is substantially determined by the organic linking compound.

22. The method as defined in claim 21, wherein the methane storage capacity is about 155 $cm^3/cm^3$.

23. A method of systematically forming an isoreticular metal-organic framework (IRMOF), the method comprising the steps of:
    dissolving at least one source of metal cations and at least one organic linking compound in a solvent to form a solution, the at least one organic linking compound comprising a linear ditopic carboxylate having at least one substituted phenyl group; and
    crystallizing the solution under predetermined conditions to form a predetermined IRMOF;
    wherein at least one of functionality, dimension, pore size and free volume of the IRMOF is substantially determined by the organic linking compound;
    and wherein the density of the IRMOF is between about 1.0 $g/cm^3$ and about 0.2 $g/cm^3$.

24. A method of systematically forming an isoreticular metal-organic framework (IRMOF), the method comprising the steps of:
    dissolving at least one source of metal cations and at least one organic linking compound in a solvent to form a solution: and
    crystallizing the solution under predetermined conditions to form a predetermined IRMOF;
    wherein at least one of functionality, dimension, pore size and free volume of the IRMOF is substantially determined by the organic linking compound;
    and wherein the density of the IRMOF is between about 0.41 $g/cm^3$ and about 0.21 $g/cm^3$.

25. A method of systematically forming an isoreticular metal-organic framework (IRMOF), the method comprising the steps of:
    dissolving at least one source of metal cations and at least one organic linking compound in a solvent to form a solution, wherein the metal cation is a cation of a metal chosen from at least one of beryllium, zinc, cadmium, mercury, any of the transition metals in the periodic table, scandium through copper, yttrium through silver, lanthanum through gold, and all known elements from actinium on, and wherein the at least one organic linking compound is a linear ditopic carboxylate having at least one substituted phenyl group; and
    crystallizing the solution under predetermined conditions to form the IRMOF, wherein the predetermined conditions are at least one of: leaving the solution at room temperature; adding a diluted base to the solution to initiate the crystallization; diffusing a diluted base into the solution to initiate the crystallization; and transferring the solution to a closed vessel and heating to a predetermined temperature;
    wherein at least one of functionality, dimension, pore size and free volume of the IRMOF is substantially determined by the organic linking compound.

26. A method of systematically forming an isoreticular metal-organic framework (IRMOF), the method comprising the steps of:
    dissolving at least one source of metal cations and at least one organic linking compound in a solvent to form a solution, wherein the metal cation is a cation of a metal chosen from at least one of beryllium, zinc, cadmium, mercury, any of the transition metals in the periodic table, scandium through copper, yttrium through silver, lanthanum through gold, and all known elements from actinium on, and wherein the at least one organic linking compound is a linear ditopic carboxylate having at least one substituted phenyl group; and crystallizing the solution under predetermined conditions to form the IRMOF, wherein the predetermined conditions are at least one of: leaving the solution at room temperature; adding a diluted base to the solution to initiate the crystallization; diffusing a diluted base into the solution to initiate the crystallization; and transferring the solution to a closed vessel and heating to a predetetmined temperature;

wherein at least one of functionality, dimension, pore size and free volume of the IRMOF is substantially determined by the organic linking compound;

and wherein the linear ditopic carboxylate is selected from the group consisting of:

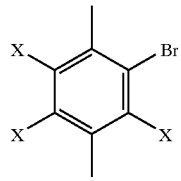

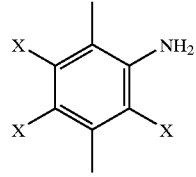

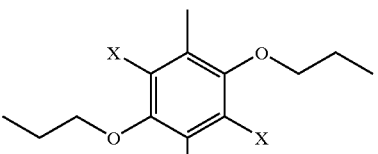

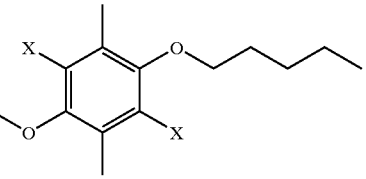

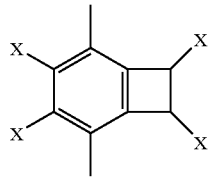

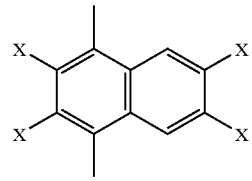

-continued

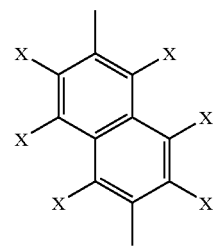

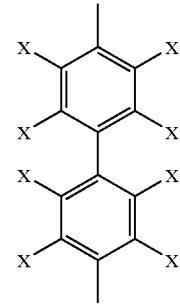

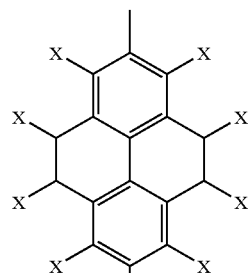

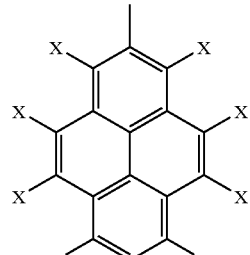

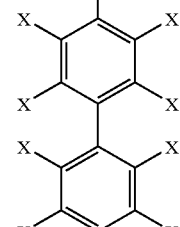

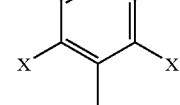

wherein the functional group X is at least one of hydrogen, amines, halides, an R group comprising at least one of linear, substituted or cyclo alkanes, alkenes, alkynes, chains, and ether O—R, wherein R is at least one of linear, substituted or cyclo alkanes, alkenes, alkynes, chains, and mixtures thereof.

27. The method as defined in claim 26 wherein the at least one source of metal cations is a plurality of secondary building units (SBUs), and wherein each of the SBUs is a multi-metal nuclear carboxylate cluster.

28. The method as defined in claim 27 wherein the multi-metal nuclear carboxylate cluster is $M_4O(CO_2)_6$.

29. The method as defined in claim 28 wherein X comprises at least one of primary, secondary or tertiary amines; aromatic amines, pyridine, pyrimidine like 5 or 6 membered rings; halides including substituted —RX; alcohols: ROH; thiols: RSH; sulfonates —R—$SO_3$; nitro groups —R($NO_2$); phosphates —R—$PO_2^-$; epoxides; aldehydes (RCOH); ketones (RCOR); esters $RCO_2R$ carboxylic acids; cycloalkenes; cycloalkynes; silyls derivatives; boranes derivatives; ferrocenes, other metallocenes, and mixtures thereof.

30. The method as defined in claim 29 wherein the at least one source of metal cations is a metal salt formed from a metal cation and an anion, the metal cation being a cation of a metal selected from the group consisting of zinc, cadmium, mercury, and transition metals, and wherein the anion is selected from the group consisting of $F^-$, $Cl^-$, $Br^-$, $I^-$, $ClO^-$, $ClO_2^-$, $ClO_3^-$, $ClO_4^-$, $OH^-$, $NO_3^-$, $NO_2^-$, $SO_4^{2-}$, $SO_3^{2-}$, $PO_4^{3-}$, $CO_3^{2-}$, $CH_3CO_2^-$, $HCO_2^-$ and $CF_3SO_3^-$, $B_4O_7^{2-}$ and $PF_6^-$.

31. The method as defined in claim 30, further comprising the step of storing at least one gas within the IRMOF.

32. A method of systematically forming an isoreticular metal-organic framework (IRMOF), the method comprising the steps of:

dissolving at least one source of metal cation and at least one organic linking compound in a solvent to form a solution, wherein the metal cation is a cation of a metal chosen from at least one of beryllium, zinc, cadmium, mercury, any of the transition metals in the periodic table, scandium through copper, yttrium through silver, lanthanum through gold, and all known elements from actinium on, and wherein the at least one organic linking compound is a linear ditopic carboxylate having at least one phenyl group;

crystallizing the solution under predetermined conditions to form the IRMOF, wherein the predetermined conditions are at least one of; leaving the solution at room temperature; adding a diluted base to the solution to initiate the crystallization; diffusing a diluted base into the solution to initiate the crystallization; and transferring the solution to a closed vessel and heating to a predetermined temperature; and storing methane within the IRMOF;

wherein at least one of functionality, dimension, pore size and free volume of the IRMOF is substantially determined by the organic linking compound;

wherein the linear ditopic carboxylate is selected from the group consisting of;

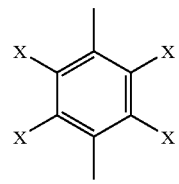

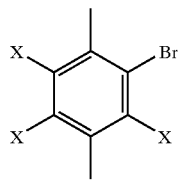

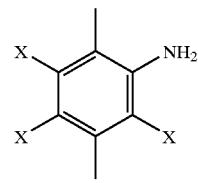

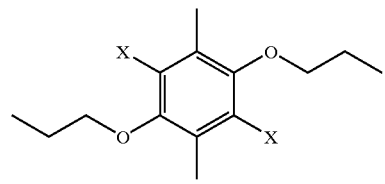

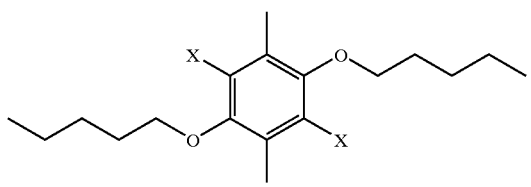

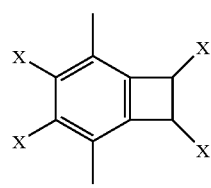

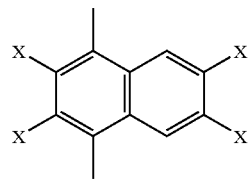

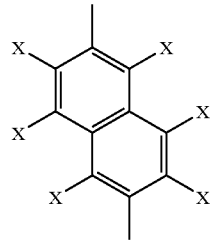

-continued

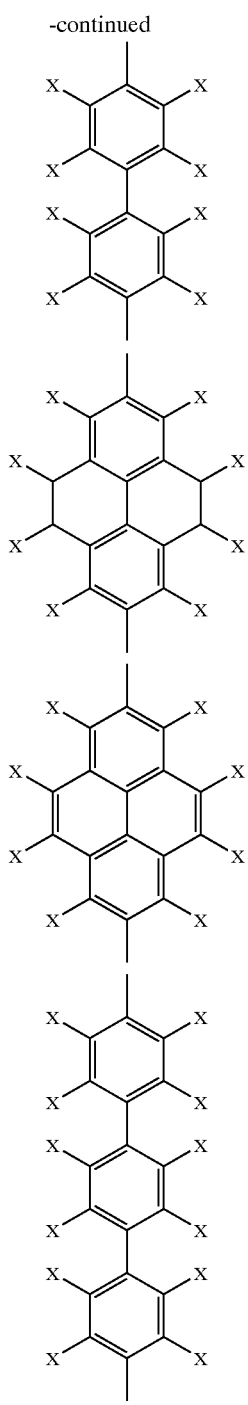

and wherein the functional group X is at least one of hydrogen, amines, halides, an R group comprising at least one of linear, substituted or cyclo alkanes, alkenes, alkynes, chains, and ether O—R, wherein R is at least one of linear, substituted or cyclo alkanes, alkenes, alkynes, chains, and mixtures thereof.

33. The method as defined in claim 32, wherein the methane storage capacity is about 155 cm³/cm³.

34. The method as defined in claim 33 wherein the density of the IRMOF is between about 1.0 g/cm³ and about 0.2 g/cm³.

35. The method as defined in claim 34 wherein the density of the IRMOF is between about 0.41 g/cm³ and about 0.21 g/cm³.

36. A systematically formed isoreticular metal-organic framework (IRMOF), consisting essentially of:
    at least one source of metal cations; and
    at least one organic linking compound comprising a linear diptopic carboxylate having at least one substituted phenyl group, wherein the at least one source of metal cations and the organic linking compound are dissolved in solution and crystallized under predetermined conditions to form a predetermined IRMOF;
    wherein at least one of functionality, dimension, pore size and free volume of the IRMOF is substantially determined by the organic linking compound.

37. The IRMOF as defined in claim 36 wherein the at least one source of metal cations is a metal salt formed from a metal cation and an anion, the metal cation being a cation of a metal selected from the group consisting of zinc, cadmium, mercury, and transition metals, and wherein the anion is selected from the group consisting of $F^-$, $Cl^-$, $Br^-$, $I^-$, $ClO^-$, $ClO_2^-$, $ClO_3^-$, $ClO_4^-$, $OH^-$, $NO_3^-$, $NO_2^-$, $SO_4^{2-}$, $SO_3^{2-}$, $PO_4^{3-}$, $CO_3^{2-}$, $CH_3CO_2^-$, $HCO_2^-$ and $CF_3SO_3^-$, $B_4O_7^{2-}$ and $PF_6^-$.

38. The IRMOF as defined in claim 36 wherein at least one functional group X is attached to the at least one substituted phenyl group.

39. The IRMOF as defined in claim 36 wherein the predetermined conditions are at least one of: leaving the solution at room temperature; adding a diluted base to the solution to initiate the crystallization; diffusing a diluted base into the solution to initiate the crystallization; and transferring the solution to a closed vessel and heating to a predetermined temperature.

40. The IRMOF as defined in claim 36 wherein the at least one source of metal cations is a plurality of secondary building units (SBUs).

41. The IRMOF as defined in claim 40 wherein each of the SBUs is a multi-metal nuclear carboxylate cluster.

42. The IRMOF as defined in claim 41 wherein the multi-metal nuclear carboxylate cluster is $M_4O(CO_2)_6$.

43. A systematically formed isoreticular metal-organic framework (IRMOF), consisting essentially of:
    at least one source of metal cations; and
    at least one organic linking compound, wherein the at least one source of metal cations and the organic linking compound are dissolved in solution and crystallized under predetermined conditions to form a predetermined IRMOF;
    wherein at least one of functionality, dimension, pore size and free volume of the IRMOF is substantially determined by the organic linking compound;
    wherein the at least one organic linking compound is a linear ditopic carboxylate having at least one substituted phenyl group,
    and wherein the linear ditopic carboxylate is selected from the group consisting of:

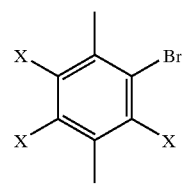

-continued

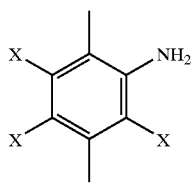

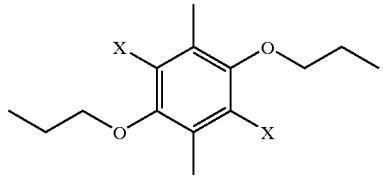

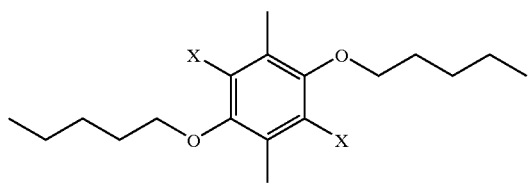

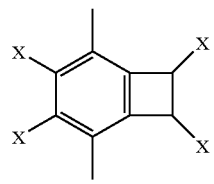

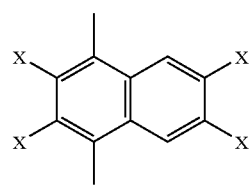

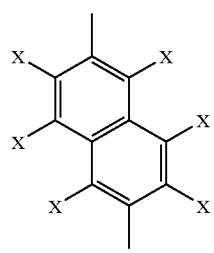

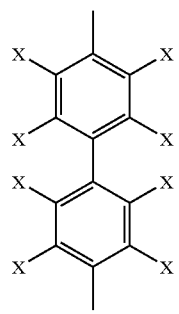

-continued

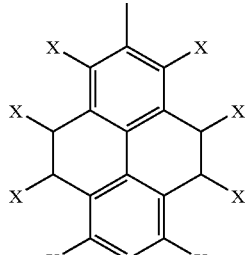

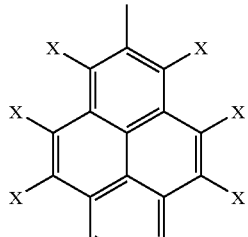

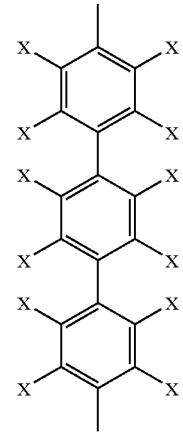

wherein the functional group X is at least one of hydrogen, amines, halides, an R group comprising at least one of linear, substituted or cyclo alkanes, alkenes, alkynes, chains, and ether O—R, wherein R is at least one of linear, substituted or cyclo alkanes, alkenes, alkynes, chains, and mixtures thereof.

44. The IRMOF as defined in claim 43 wherein X comprises at least one of primary, secondary or tertiary amines; aromatic amines, pyridine, pyrimidine like 5 or 6 membered rings; halides including substituted —RX; alcohols: ROH; thiols: RSH; sulfonates —R—$SO_3$; nitro groups —R($NO_2^-$); phosphates —R—$PO_2$; epoxides; aldehydes (RCOH); ketones (RCOR); esters $RCO_2R$; carboxylic acids; cycloalkenes; cycloalkynes; silyls derivatives; boranes derivatives; ferrocenes, other metallocenes, and mixtures thereof.

45. A systematically formed isoreticular metal-organic framework (IRMOF), consisting essentially of:
at least one source of metal cations; and
at least one organic linking compound comprising a linear ditopic carboxylate having at least one substituted phenyl group, wherein the at least one source of metal cations and the organic linking compound are dissolved in solution and crystallized under predetermined conditions to form a predetermined IRMOF;

wherein at least one of functionality, dimension, pore size and free volume of the IRMOF is substantially determined by the organic linking compound, and wherein the metal cation is a cation of a metal chosen from at least one of beryllium, zinc, cadmium, mercury, any of the transition metals in the periodic table, scandium through copper, yttrium through silver, lanthanum through gold, and all known elements from actinium on.

46. A systematically formed isoreticular metal-organic framework (IRMOF), consisting essentially of:

at least one source of metal cations; and at least one organic linking compound comprising a linear ditopic carboxylate having at least one substituted phenyl group, wherein the at least one source of metal cations and the organic linking compound are dissolved in solution and crystallized under predetermined conditions to form a predetermined IRMOF;

wherein at least one of functionality, dimension, pore size and free volume of the IRMOF is substantially determined by the organic linking compound;

and wherein the IRMOF is adapted to store at least one gas.

47. A systematically formed isoreticular metal-organic framework (IRMOF), consisting essentially of:

least one source of metal cations; and at least one organic linking compound, wherein the at least one source of metal cations and the organic linking compound are dissolved in solution and crystallized under predetermined conditions to form a predetermined IRMOF;

wherein at least one of functionality, dimension, pore size and free volume of the IRMOF is substantially determined by the organic linking compound;

and wherein the IRMOF is adapted to store methane.

48. The IRMOF as defined in claim 47 wherein the methane storage capacity is about 155 cm$^3$/cm$^3$.

49. A systematically formed isoreticular metal-organic framework (IRMOF), consisting essentially of;

at least one source of metal cations; and at least one organic linking compound comprising a linear diptopic carboxylate having at least one substituted phenyl group, wherein the at least one source of metal cations and the organic linking compound are dissolved in solution and crystallized under predetermined conditions to form a predetermined IRMOF;

wherein at least one of functionality, dimension, pore size and free volume of the IRMOF is substantially determined by the organic linking compound;

and wherein the density of the IRMOF is between about 1.0 g/cm$^3$ and about 0.2 g/cm$^3$.

50. A systematically formed isoreticular metal-organic framework (IRMOF), consisting essentialiy of;

at least one source of metal cations; and at least one organic linking compound, wherein the at least one source of metal cations and the organic linking compound are dissolved in solution and crystallized under predetermined conditions to form a predetermined IRMOF;

wherein at least one functionality, dimension, pore size and free volume of the IRMOF is substantially deterimned by the organic linking compound;

and wherein the density of the IRMOF is between about 0.41 g/cm$^3$ and about 0.21 g/cm$^3$.

51. A systematically formed isoreticular metal-organic framework (IRMOF), consisting essentially of:

at least one source of metal cations, wherein the metal cation is a cation of a metal chosen from at least one of beryllium, zinc, cadmium, mercury, any of the transition metals in the periodic table, scandium through copper, yttrium through silver, lanthanum through gold, and all known elements from actinium on; and at least one organic linking compound, wherein the at least one organic linking compound is a linear ditopic carboxylate having at least one substituted phenyl group, wherein the at least one source of metal cations and the organic linking compound are dissolved in solution and crystallized under predetermined conditions to form a predetermined IRMOF;

wherein the predetermined conditions are at least one of: leaving the solution at room temperature; adding a diluted base to the solution to initiate the crystallization; diffusing a diluted base into the solution to initiate the crystallization; and transferring the solution to a closed vessel and heating to a predetermined temperature;

and wherein at least one of functionality, dimension, pore size and free volume of the IRMOF is substantially determined by the organic linking compound.

52. The IRMOF as defined in claim 51 wherein the linear ditopic carboxylate is selected from the group consisting of:

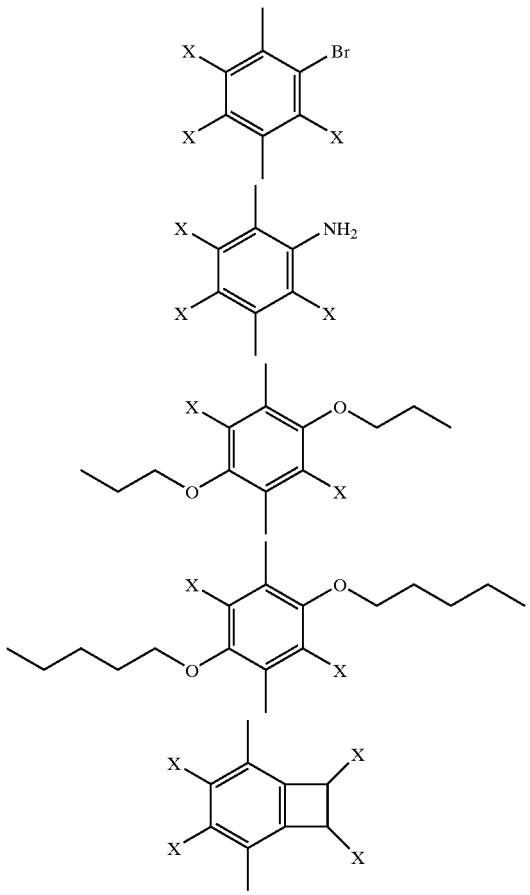

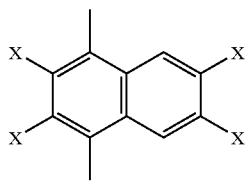

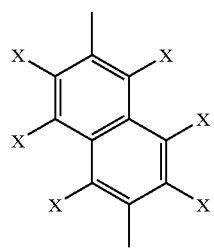

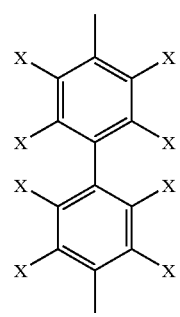

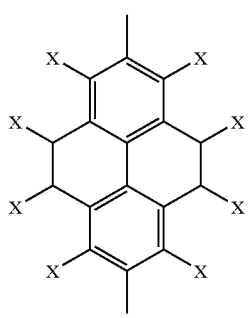

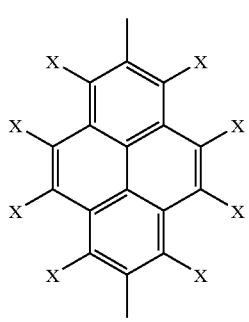

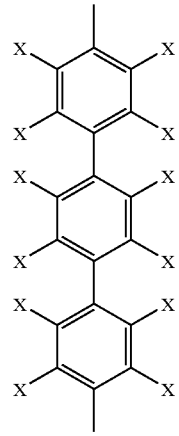

wherein the functional group X is at least one of hydrogen, armines, halides, an R group selected from at least one of linear, substituted or cyclo alkanes, alkenes, alkynes, chains, and ether O—R, wherein R is at least one of linear, substituted or cyclo alkanes, alkenes, alkynes, chains, and mixtures thereof.

53. The IRMOF as defined in claim 52 wherein the at least one source of metal cations is a plurality of secondary building units (SBUs), and wherein each of the SBUs is a multi-metal nuclear carboxylate cluster.

54. The IRMOF as defined in claim 53 wherein the multi-metal nuclear carboxylate cluster is $M_4O(CO_2)_6$.

55. The IRMOF as defined in claim 54 wherein X comprises at least one of primary, secondary or tertiary amines; aromatic amines, pyridine, pyrimidine like 5 or 6 membered rings; halides including substituted —RX; alcohols: ROH; thiols: RSH; sulfonates —R—$SO_3$; nitro groups —R($NO_2^-$); phosphates —R—$PO_2^-$; epoxides; aldehydes (RCOH); ketones (RCOR); esters $RCO_2R$; carboxylic acids; cycloalkenes; cycloalkynes; silyls derivatives; boranes derivatives; ferrocenes, other metallocenes, and mixtures thereof.

56. The IRMOF as defined in claim 55 wherein the at least one source of metal cations is a metal salt formed from a metal cation and an anion, the metal cation being a cation of a metal selected from the group consisting of zinc, cadmium, mercury, and transition metals, and wherein the anion is selected from the group consisting of $F^-$, $Cl^-$, $Br^-$, $I^-$, $ClO^-$, $ClO_2^-$, $ClO_3^-$, $ClO_4^-$, $OH^-$, $NO_3^-$, $NO_2^-$, $SO_4^{2-}$, $SO_3^{2-}$, $PO_4^{3-}$, $CO_3^{2-}$, $CH_3CO_2^-$, $HCO_2^-$ and $CF_3SO_3^-$, $B_4O_7^{2-}$ and $PF_6^-$.

57. The IRMOF as defined in claim 56 wherein the IRMOF is adapted to store at least one gas.

58. The IRMOF as defined in claim 57 wherein the at least one gas is methane.

59. The IRMOF as defined in claim 58, wherein the methane storage capacity is about 155 cm³/cm³.

60. The IRMOF as defined in claim 59 wherein the density of the IRMOF is between about 1.0 g/cm³ and about 0.2 g/cm³.

61. The IRMOF as defined in claim 60 wherein the density of the IRMOF is between about 0.41 g/cm³ and about 0.21 g/cm³.

62. A systematically formed isoreticular metal-organic framework (IRMOF), consisting essentially of:
- a plurality of secondary building units (SBUs), each of the plurality of SBUs comprising an $M_4O(CO_2)_6$ cluster; and
- a compound linking adjacent SBUs, the linking compound comprising a linear ditopic carboxylate having at least one phenyl group and at least one functional group X attached to the at least one phenyl group;
- wherein the IRMOF has a substantially permanent porosity and is substantially stable;
- wherein the functional group X is at least one of hydrogen, amines, halides, an R group selected from at least one of linear, substituted or cyclo alkanes, alkenes, alkynes, chains, and ether O—R, wherein R is at least one of linear, substituted or cyclo alkanes, alkenes, alkynes, chains, and mixtures thereof;
- wherein at least one of functionality, dimension, pore size and free volume of the IRMOF is substantially determined by the linking compound; and
- wherein M in the SBU is a metal cation of a metal chosen from at least one of beryllium, cadmium, mercury, any of the transition metals in the periodic table, scandium through copper, yttrium through silver, lanthanum through gold, and all known elements from actinium on.

\* \* \* \* \*

UNITED STATES PATENT AND TRADEMARK OFFICE
CERTIFICATE OF CORRECTION

PATENT NO. : 6,930,193 B2
DATED : August 16, 2005
INVENTOR(S) : Omar M. Yaghi et al.

It is certified that error appears in the above-identified patent and that said Letters Patent is hereby corrected as shown below:

Column 28,
Line 16, after "I⁻," insert -- ClO⁻. --.

Column 41,
Line 65, after "one" insert -- of --.

Column 44,
Line 23, delete "armines" and insert -- amines --.

Signed and Sealed this

Eighth Day of November, 2005

JON W. DUDAS
*Director of the United States Patent and Trademark Office*